US012605507B2

(12) United States Patent
Zoda et al.

(10) Patent No.: US 12,605,507 B2
(45) Date of Patent: Apr. 21, 2026

(54) CASSETTE, MEDICINE INJECTION DEVICE, AND MEDICINE INJECTION SYSTEM

(71) Applicant: PHC Holdings Corporation, Tokyo (JP)

(72) Inventors: Mitsuaki Zoda, Ehime (JP); Kazumasa Okamura, Ehime (JP); Kenichi Yano, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 945 days.

(21) Appl. No.: 17/794,151

(22) PCT Filed: Jan. 14, 2021

(86) PCT No.: PCT/JP2021/001095
§ 371 (c)(1),
(2) Date: Jul. 20, 2022

(87) PCT Pub. No.: WO2021/149591
PCT Pub. Date: Jul. 29, 2021

(65) Prior Publication Data
US 2023/0074484 A1    Mar. 9, 2023

(30) Foreign Application Priority Data

Jan. 23, 2020    (JP) ................................. 2020-009455

(51) Int. Cl.
*A61M 5/28* (2006.01)
*A61M 5/315* (2006.01)
(Continued)

(52) U.S. Cl.
CPC ........ *A61M 5/281* (2013.01); *A61M 5/31576* (2013.01); *A61M 5/14566* (2013.01);
(Continued)

(58) Field of Classification Search
CPC ........ A61M 5/2422; A61M 2005/2433; A61M 2005/2411; A61M 2005/2407;
(Continued)

(56) References Cited

U.S. PATENT DOCUMENTS

| | | | | |
|---|---|---|---|---|
| 2004/0108339 A1* | 6/2004 | Hansen | .................. | A61M 5/24 |
| | | | | 222/326 |
| 2014/0052075 A1* | 2/2014 | Schneider | ......... | A61M 5/31525 |
| | | | | 604/207 |

(Continued)

FOREIGN PATENT DOCUMENTS

| | | | | |
|---|---|---|---|---|
| JP | 2014-516634 A | 7/2014 | | |
| WO | WO-2012032411 A2 * | 3/2012 | ............. | A61M 5/20 |
| WO | 2016/052117 A1 | 4/2016 | | |

OTHER PUBLICATIONS

International Search Report issued on Feb. 16, 2021 in International Patent Application No. PCT/JP2021/001095, with English translation.

*Primary Examiner* — Emily L Schmidt
*Assistant Examiner* — Martin A Radomski
(74) *Attorney, Agent, or Firm* — Rimon P.C.

(57) ABSTRACT

A cassette including: a cartridge holder including a first end, a second end having a holder opening, and a holder columnar space located between the first end and the second end and capable of accommodating a drug cartridge, drug cartridge including: a cylinder including a first end at which an injection needle is insertable/extractable, a second end at which a cylinder opening is located, and a cylinder columnar space located between the first end and the second end; a drug placed in the cylinder columnar space; and a gasket being placed in the cylinder columnar space; a cassette cap capable of opening and closing the holder opening, the cassette cap including a first end having a cap opening that is opposed to the holder opening, a second end having a
(Continued)

piston insertion opening, and a cap columnar space located between the first end and the second end.

23 Claims, 26 Drawing Sheets

(51) Int. Cl.
  *A61M 5/145*          (2006.01)
  *A61M 5/24*           (2006.01)
(52) U.S. Cl.
  CPC ................ *A61M 2005/2411* (2013.01); *A61M 2005/2477* (2013.01); *A61M 2005/2496* (2013.01)
(58) Field of Classification Search
  CPC .. A61M 2005/2488; A61M 2005/2496; A61M 2005/2477; A61M 2005/3143; A61M 2005/2418; A61M 5/14546; A61M 2005/14553; A61M 5/1456; A61M 5/14566; A61M 5/31558
  USPC ........................................................ 604/187
  See application file for complete search history.

(56)                References Cited

U.S. PATENT DOCUMENTS

| 2015/0011949 | A1* | 1/2015 | Soerensen | ........... A61M 5/3158 |
| | | | | 604/235 |
| 2015/0045729 | A1 | 2/2015 | Denzer et al. | |
| 2015/0073350 | A1* | 3/2015 | Einwachter | ............. A61M 5/24 |
| | | | | 604/187 |
| 2016/0296701 | A1* | 10/2016 | Blancke | .............. A61M 5/3155 |
| 2017/0224921 | A1* | 8/2017 | Takabatake | ............. A61M 5/20 |
| 2018/0339107 | A1* | 11/2018 | Murakami | .............. A61M 5/20 |
| 2019/0388621 | A1* | 12/2019 | Dahmani | .......... A61M 5/31546 |

* cited by examiner

120

130f

130

130t2

130t1

110

130m

130k

110

110g

111

111g

11

13

126g2

126f

126g1

126h1

130h

130g

130b

126h2

126r

130e

126g2

126g1

126f

110

111

130g

130h

130

①

DRUG INJECTING OPERATION — S8

EXTRACT NEEDLE (REMOVE FROM SKIN) — S9

ATTACH/DETACH NEEDLE — S10

NO REMAINING AMOUNT OF DRUG? — S11

NO

YES

CANCEL CASSETTE LOCK & PISTON BACK TO ORIGIN — S12

SHUTDOWN PROCESS — S13

EJECT CASSETTE — S14

POWER OFF — S15

END

200'

CASSETTE, MEDICINE INJECTION DEVICE, AND MEDICINE INJECTION SYSTEM

CROSS-REFERENCE OF RELATED APPLICATIONS

This application is the U.S. National Phase under 35 U.S.C. § 371 of International Patent Application No. PCT/JP2021/001095, filed on Jan. 14, 2021, which in turn claims the benefit of Japanese Patent Application No. 2020-009455, filed on Jan. 23, 2020, the entire disclosures of which Applications are incorporated by reference herein.

TECHNICAL FIELD

The present application relates to a cassette for accommodating a medical drug cartridge, a drug injection device, and a drug injection system.

BACKGROUND ART

Patients suffering from particular diseases in some cases need to receive an injection of a drug such as insulin, growth hormone, or the like, a plurality of times a day. In order for the patients to inject such a drug by themselves, various drug injection devices as are disclosed in Patent Document 1 and the like have been put to practical use.

CITATION LIST

Patent Literature

[Patent Document 1] Japanese National Phase PCT Laid-Open Publication No. 2014-516634

SUMMARY OF INVENTION

Technical Problem

Depending on the specifications or the prescription, a drug cartridge may contain an amount of drug to be separately injected over a plurality of times. The present application provides a cassette, a drug injection device, and a drug injection system which support such drug cartridges and which permit appropriate management.

Solution to Problem

A cassette to be loaded to a drug injection device according to an embodiment of the present disclosure, the cassette comprising: a cartridge holder including a first end at which an injection needle is attachable/detachable, a second end having a holder opening, and a holder columnar space being located between the first end and the second end and capable of accommodating a drug cartridge, wherein the drug cartridge includes: a cylinder including a first end at which the injection needle is insertable/extractable, a second end at which a cylinder opening is located, and a cylinder columnar space located between the first end and the second end; a drug placed in the cylinder columnar space; and a gasket being placed in the cylinder columnar space and capable of moving along a longitudinal direction of the cylinder columnar space; a cassette cap being supported in the neighborhood of the second end of the cartridge holder so as to be capable of opening and closing the holder opening, the cassette cap including a first end having a cap opening that is opposed to the holder opening, a second end having a piston insertion opening, and a cap columnar space located between the first end and the second end. In an open state, the cassette cap allows the drug cartridge to be movable into and out of the holder columnar space of the cartridge holder, and, in a closed state, the cassette cap closes the holder opening to disallow the drug cartridge to be removed while allowing the gasket of the drug cartridge inserted into the holder columnar space to be exposed in the piston insertion opening; and a locking mechanism being located in the cap columnar space of the cassette cap and at least including a rotation lock unit that is supported so as to be capable of pivoting around an axis of the cap columnar space, wherein, the rotation lock unit has a shape that engages with a piston of the drug injection device for moving the gasket of the drug cartridge; and, while the drug cartridge is inserted in the cartridge holder and the cassette cap is in a closed state, the rotation lock unit pivots between a lock position for disallowing the cassette cap to open and an unlock position for allowing the cassette cap to open.

Advantageous Effects of Invention

According to the present disclosure, a drug injection device that permits appropriate management is provided.

being in the unlock position; and the right side shows a state where the piston is insertable in the rotation lock unit being in the lock position.

Figure 17A:
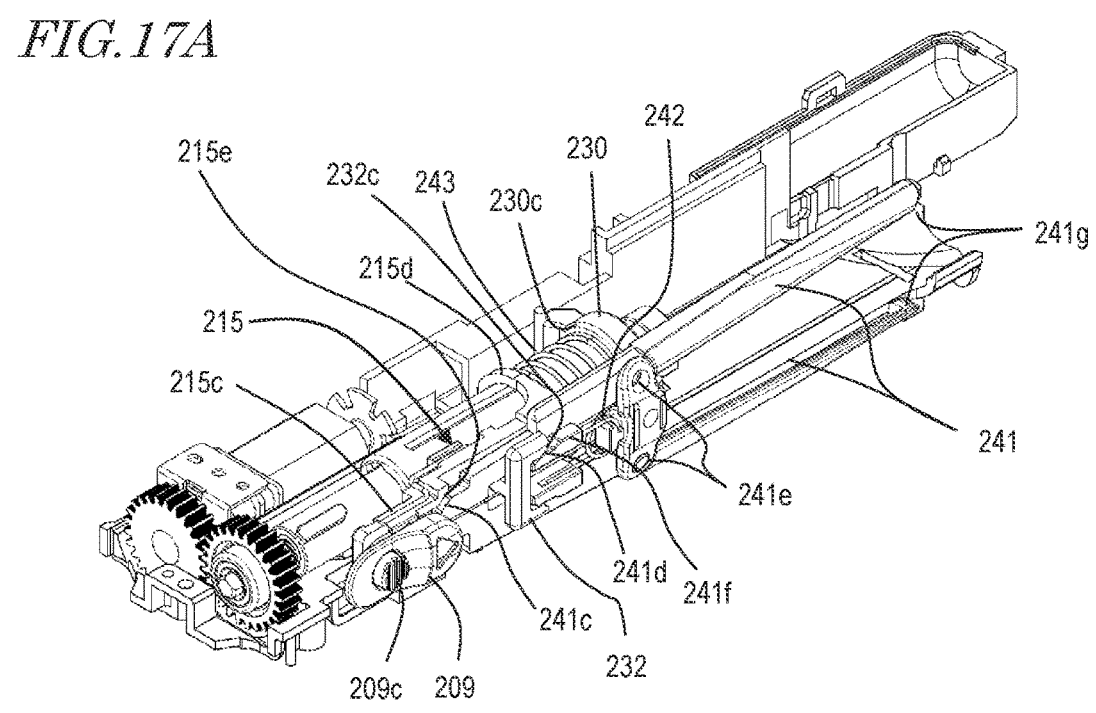

FIG. 17A is a perspective view describing a locking operation when inserting the cassette.

Figure 17B:
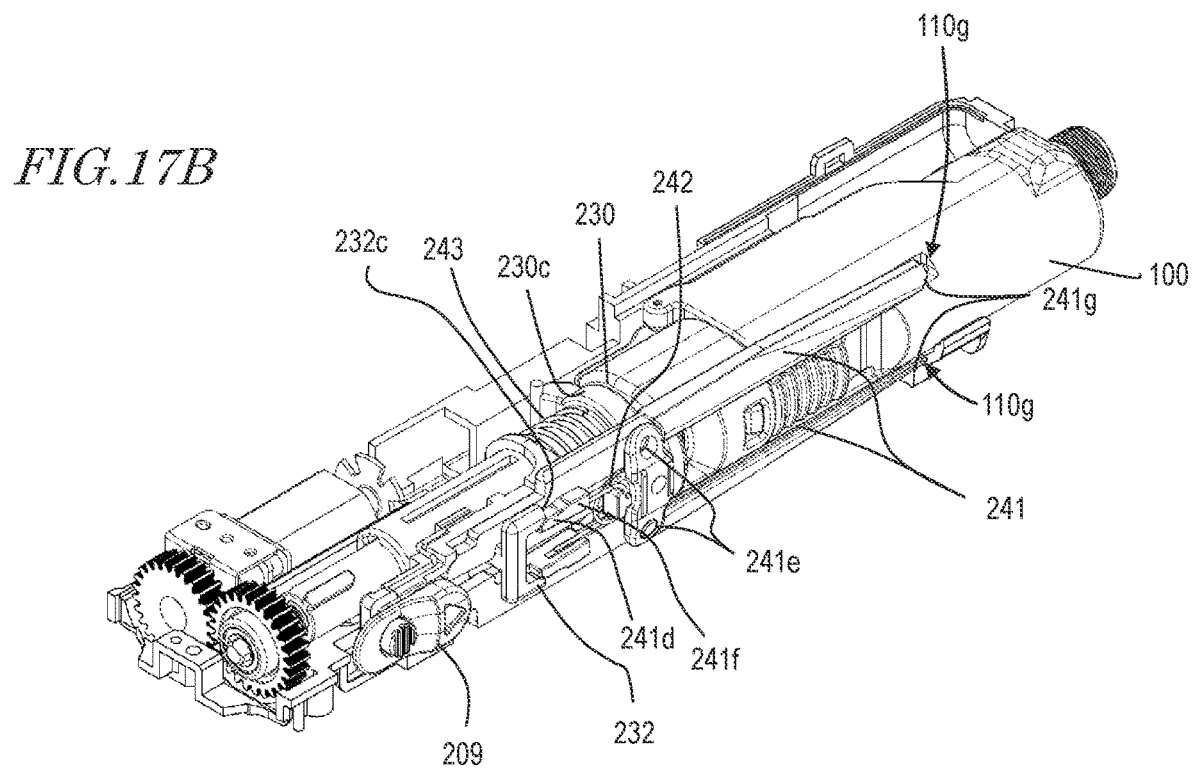

FIG. 17B is a perspective view describing a locking operation when inserting the cassette.

Figure 18A:
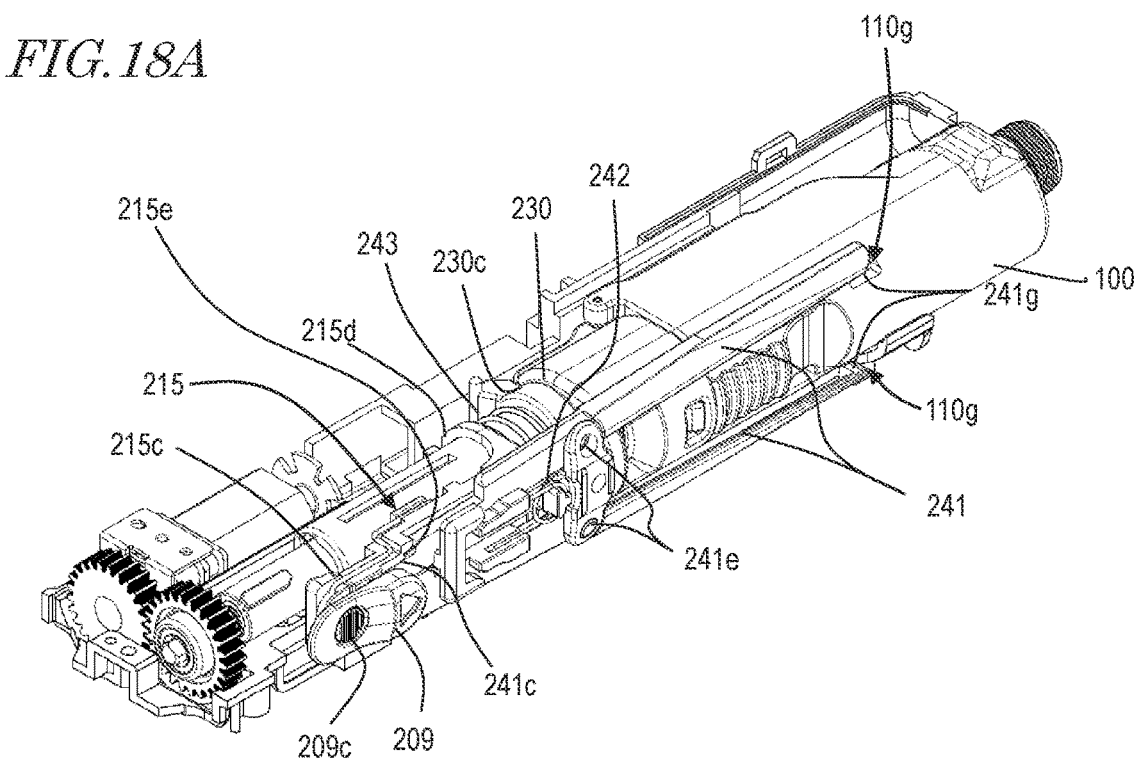

FIG. 18A is a perspective view describing an unlocking operation when ejecting the cassette.

Figure 18B:
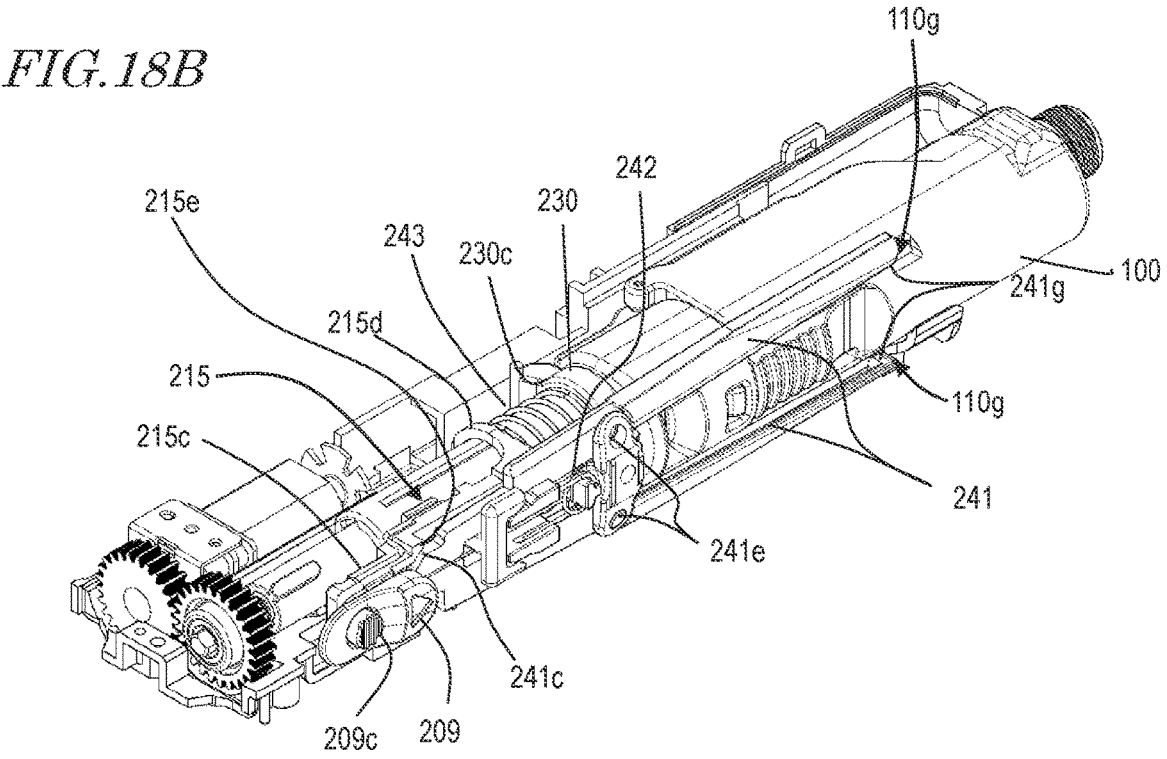

FIG. 18B is a perspective view describing an unlocking operation when ejecting the cassette.

Figure 19A:
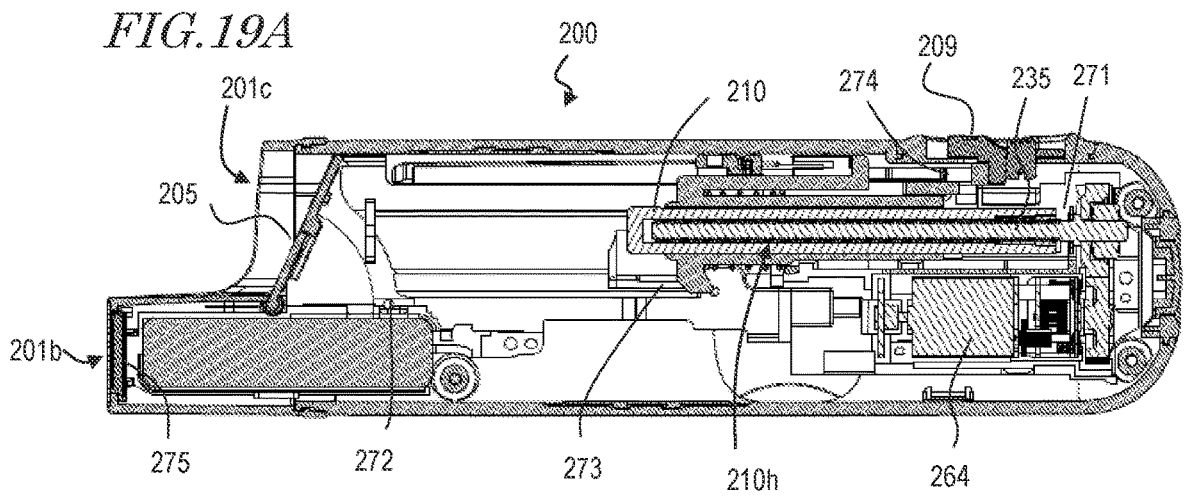

FIG. 19A is a cross-sectional view of the drug injection device.

Figure 19B:
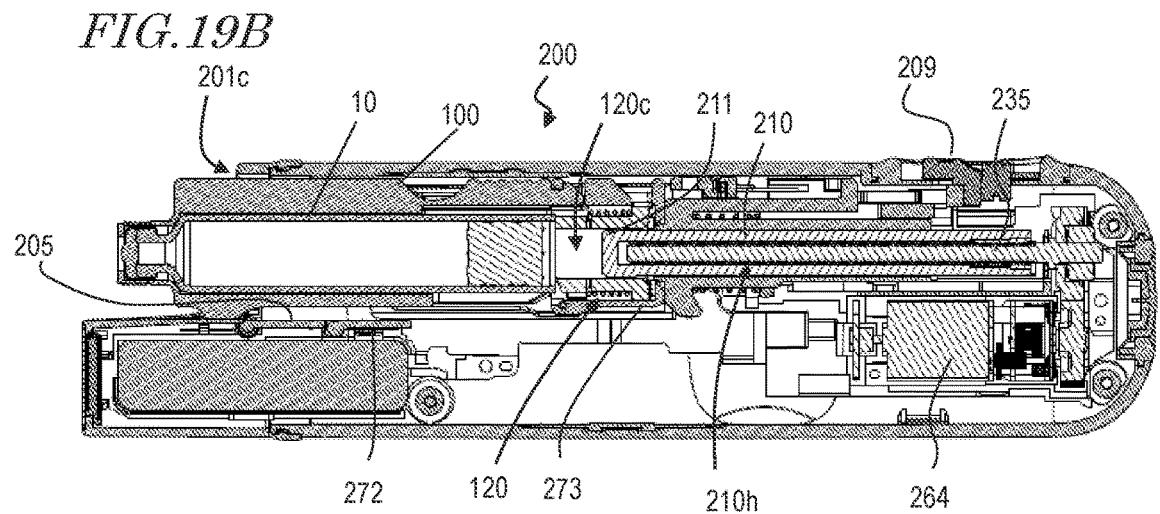

FIG. 19B is a cross-sectional view of the drug injection device.

Figure 19C:
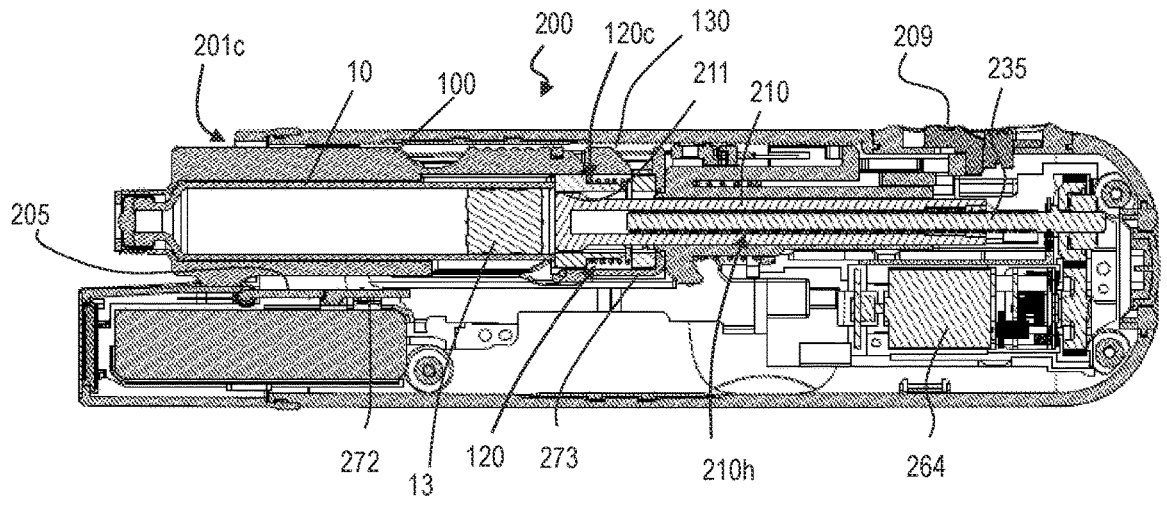

FIG. 19C is a cross-sectional view of the drug injection device.

Figure 19D:
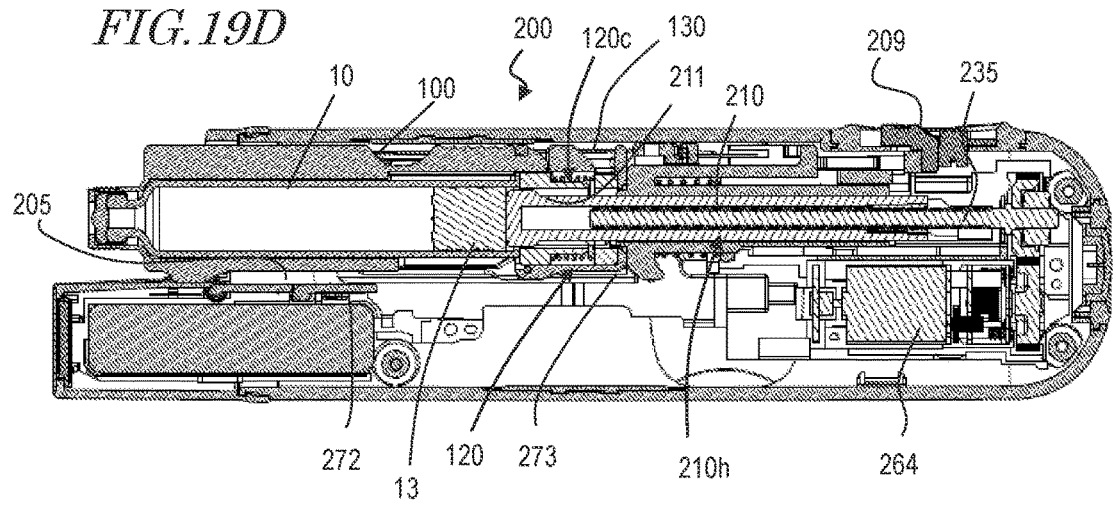

FIG. 19D is a cross-sectional view of the drug injection device.

Figure 19E:
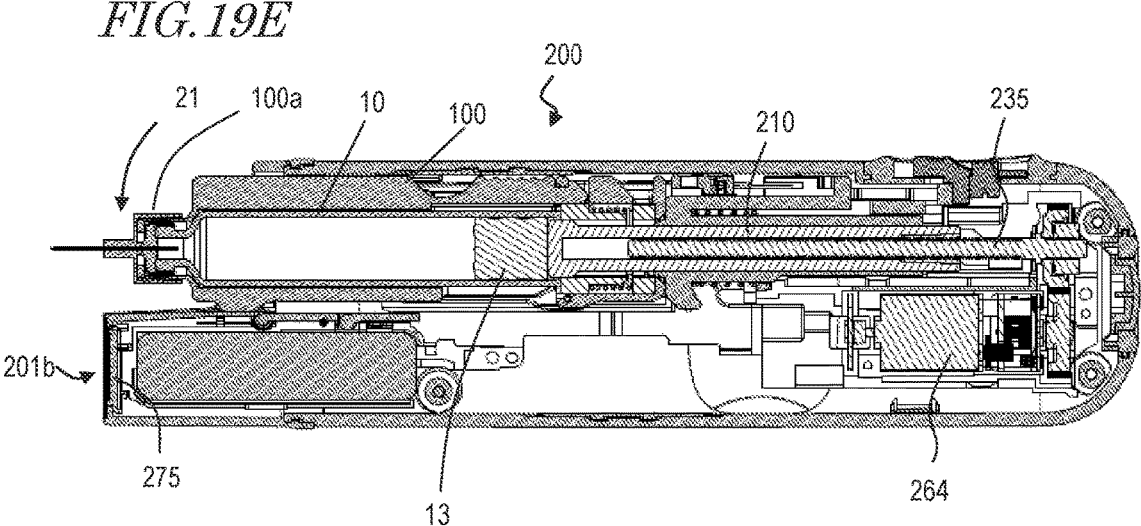

FIG. 19E is a cross-sectional view of the drug injection device.

Figure 19F:
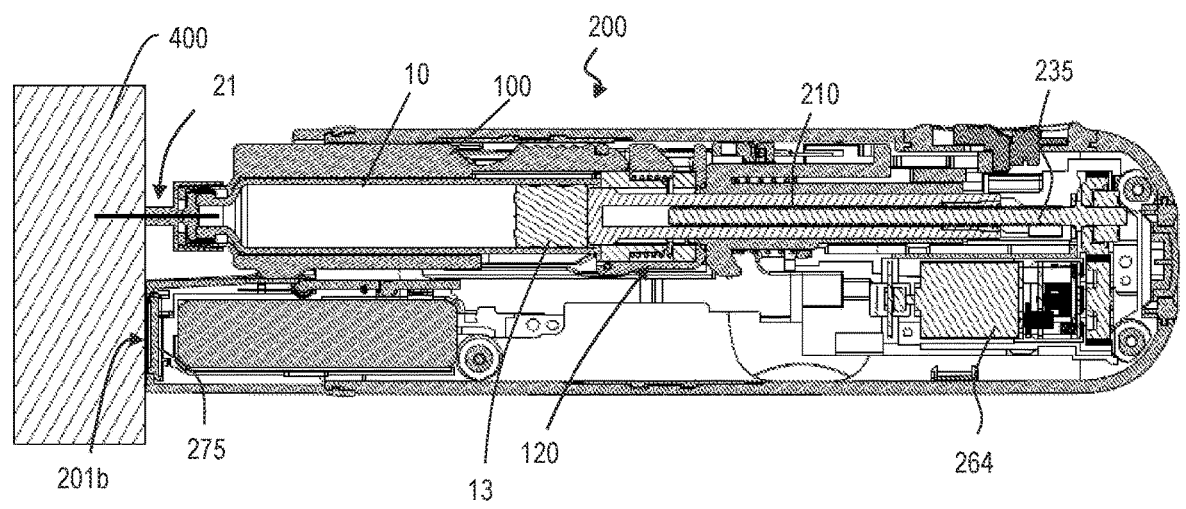

FIG. 19F is a cross-sectional view of the drug injection device.

Figure 19G:
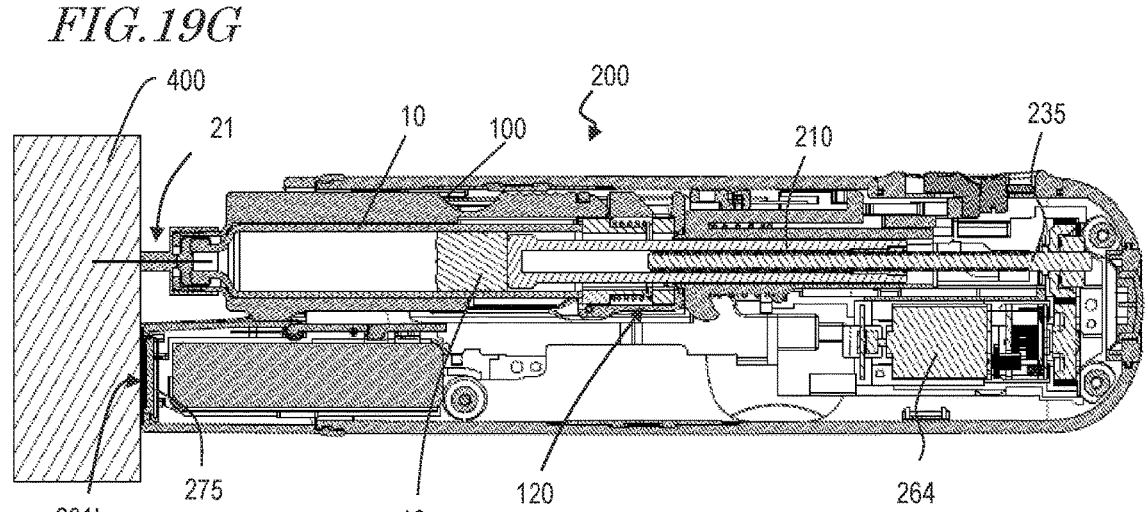

FIG. 19G is a cross-sectional view of the drug injection device.

Figure 19H:
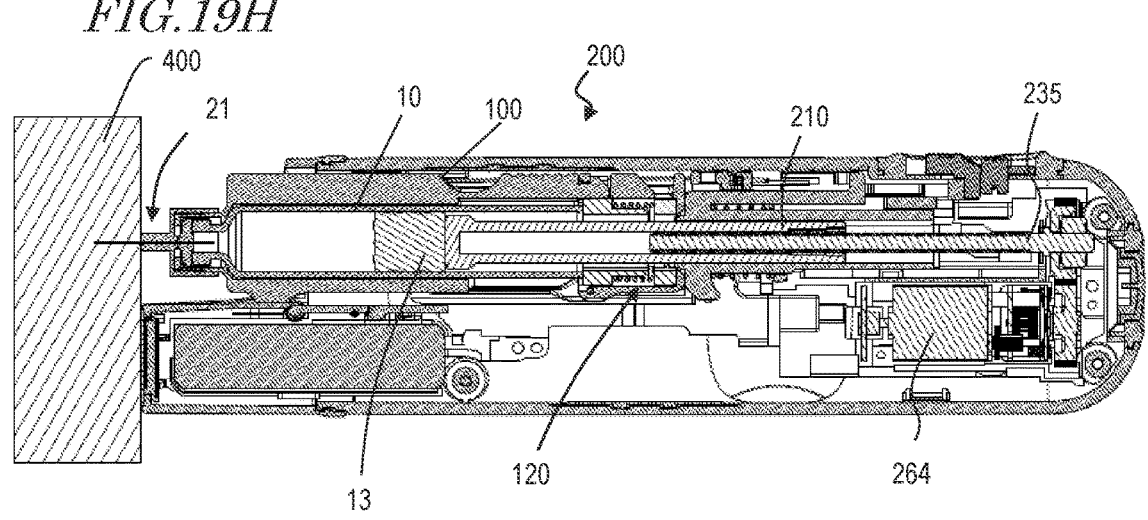

FIG. 19H is a cross-sectional view of the drug injection device.

Figure 19I:
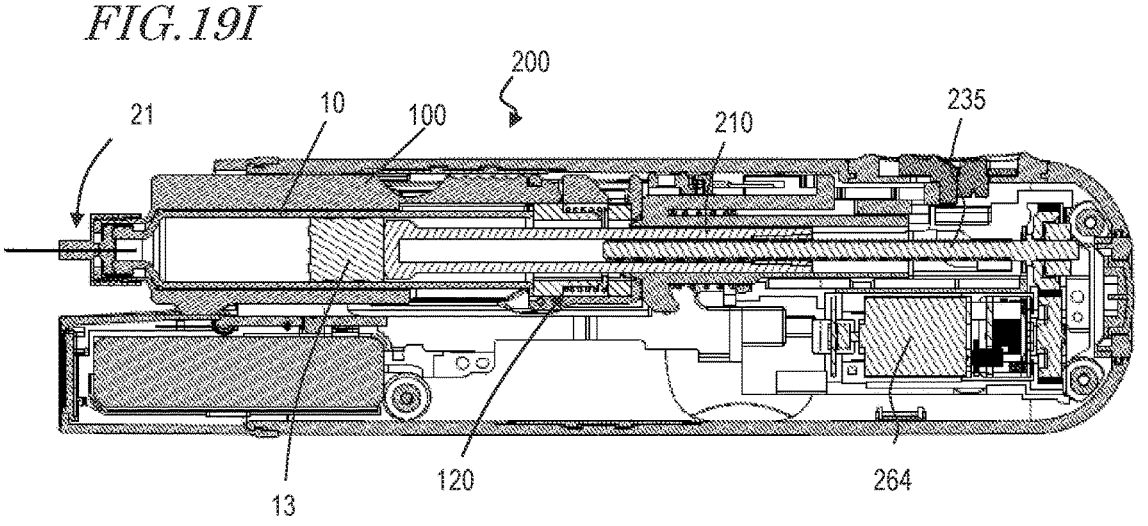

FIG. 19I is a cross-sectional view of the drug injection device.

Figure 19J:
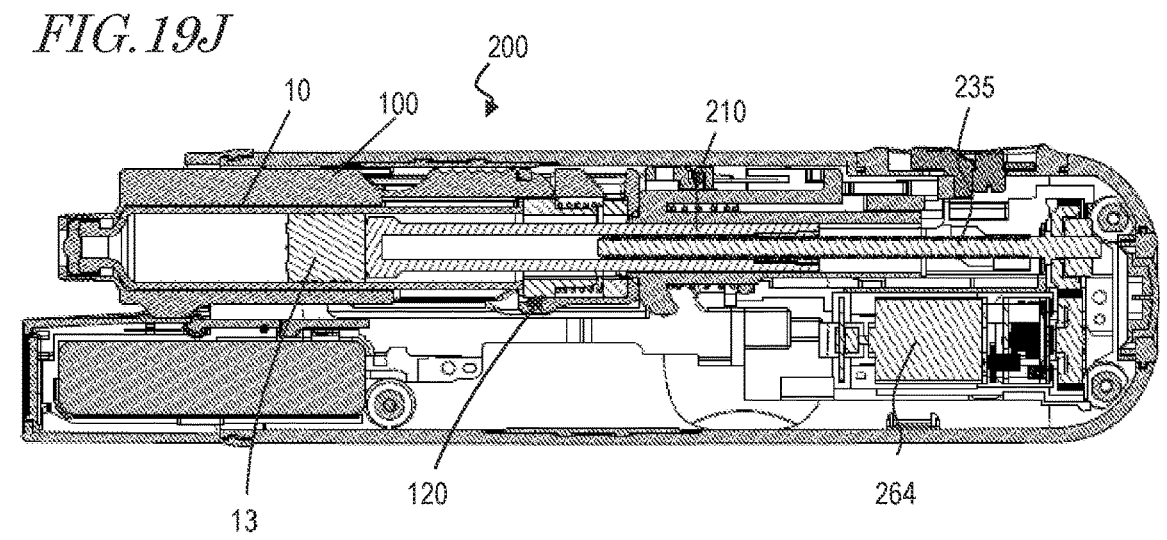

FIG. 19J is a cross-sectional view of the drug injection device.

Figure 19K:
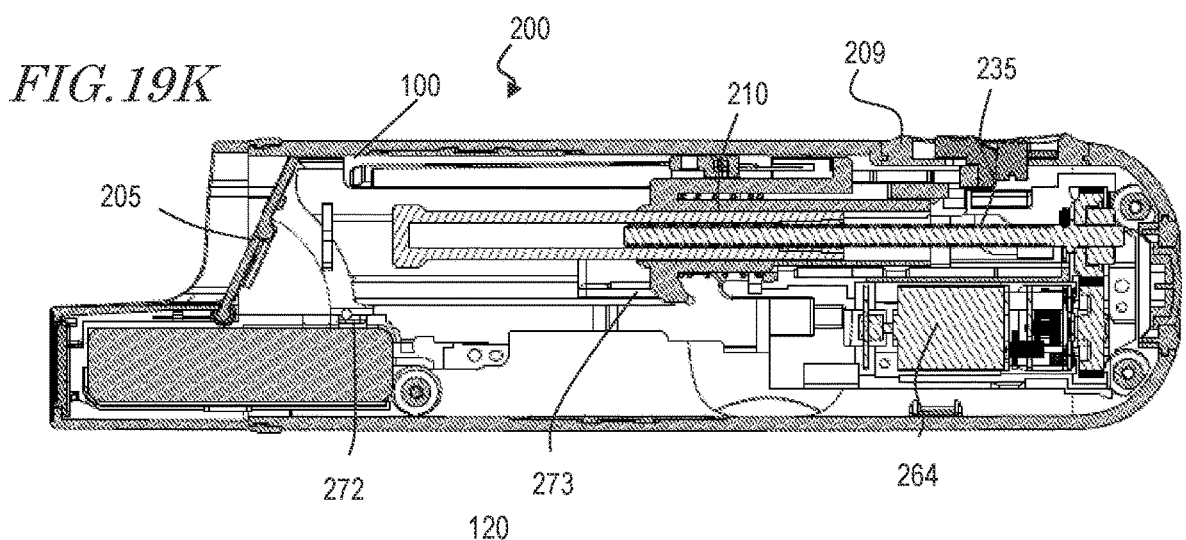

FIG. 19K is a cross-sectional view of the drug injection device.

Figure 19L:
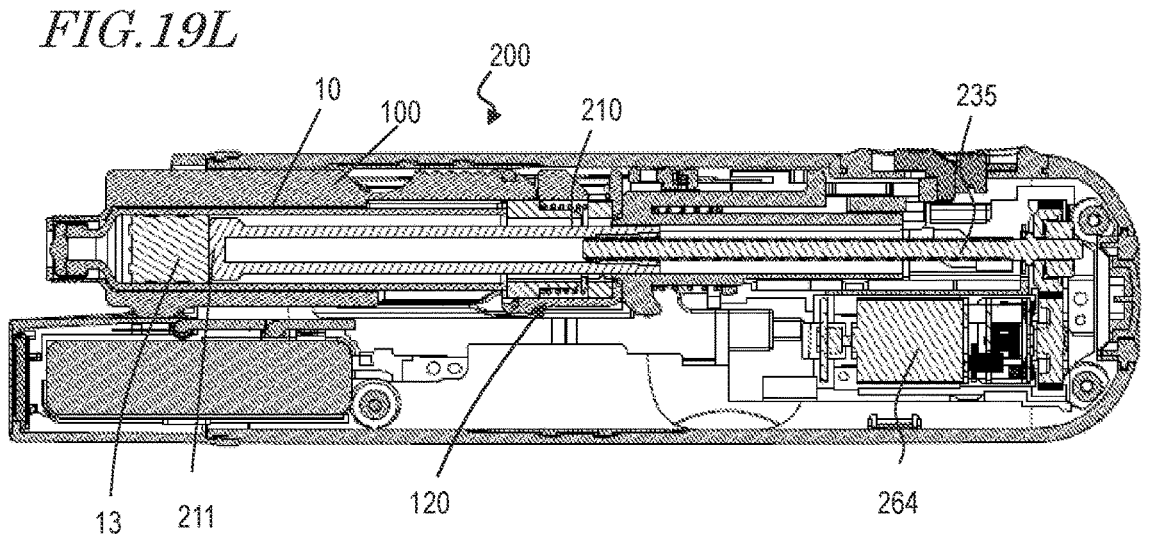

FIG. 19L is a cross-sectional view of the drug injection device.

Figure 19M:
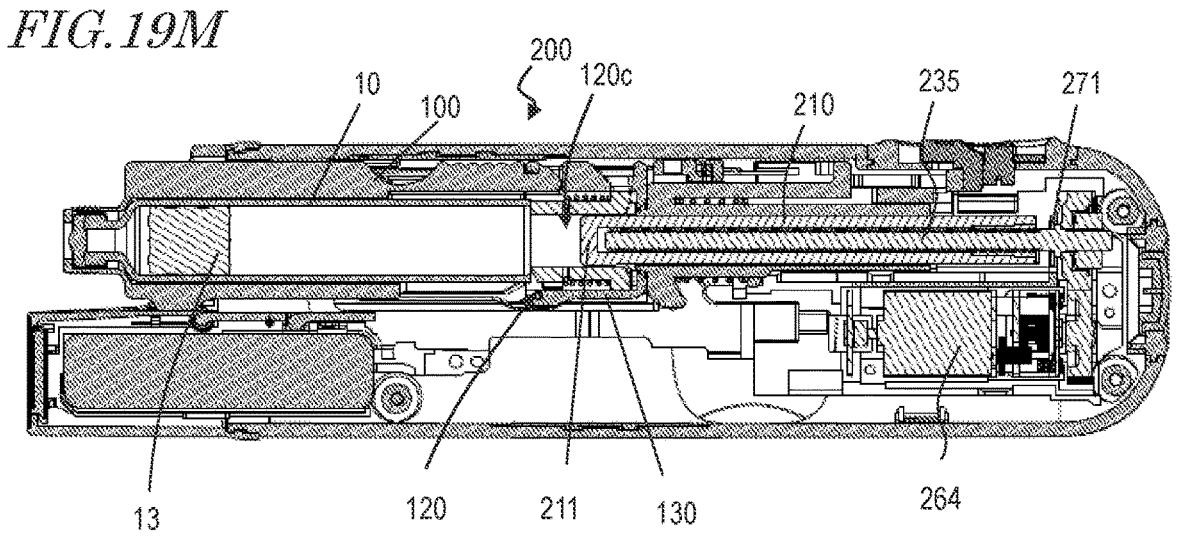

FIG. 19M is a cross-sectional view of the drug injection device.

Figure 20A:
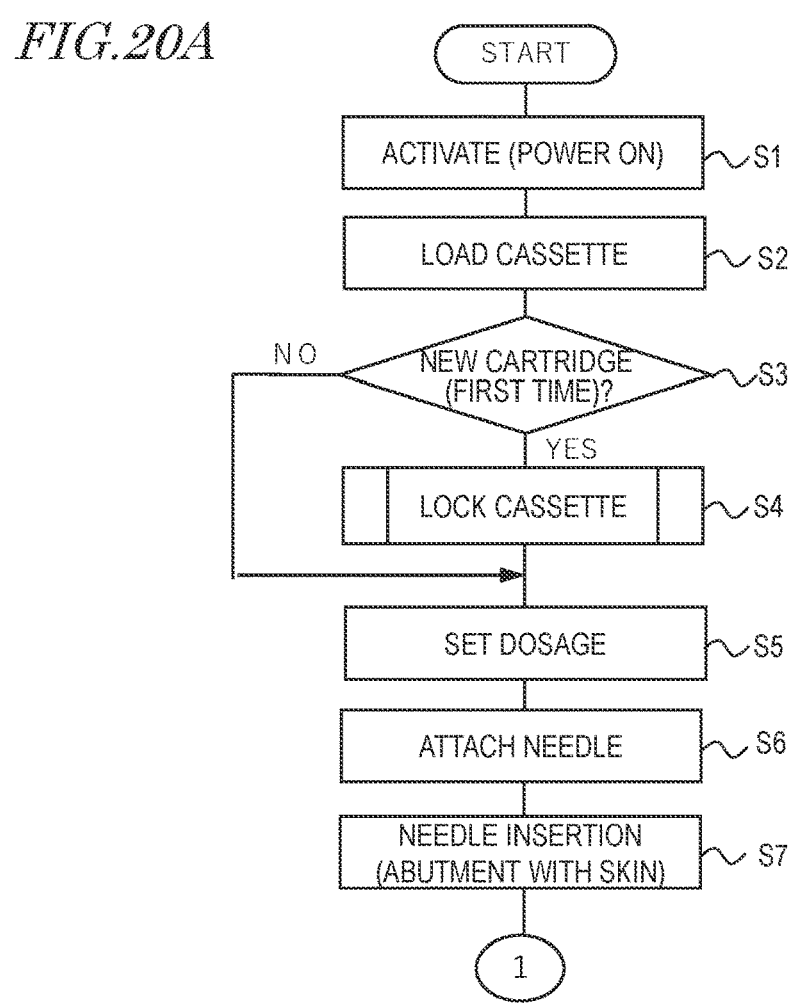

FIG. 20A is a flowchart describing procedures for manipulating the drug injection system.

Figure 20B:
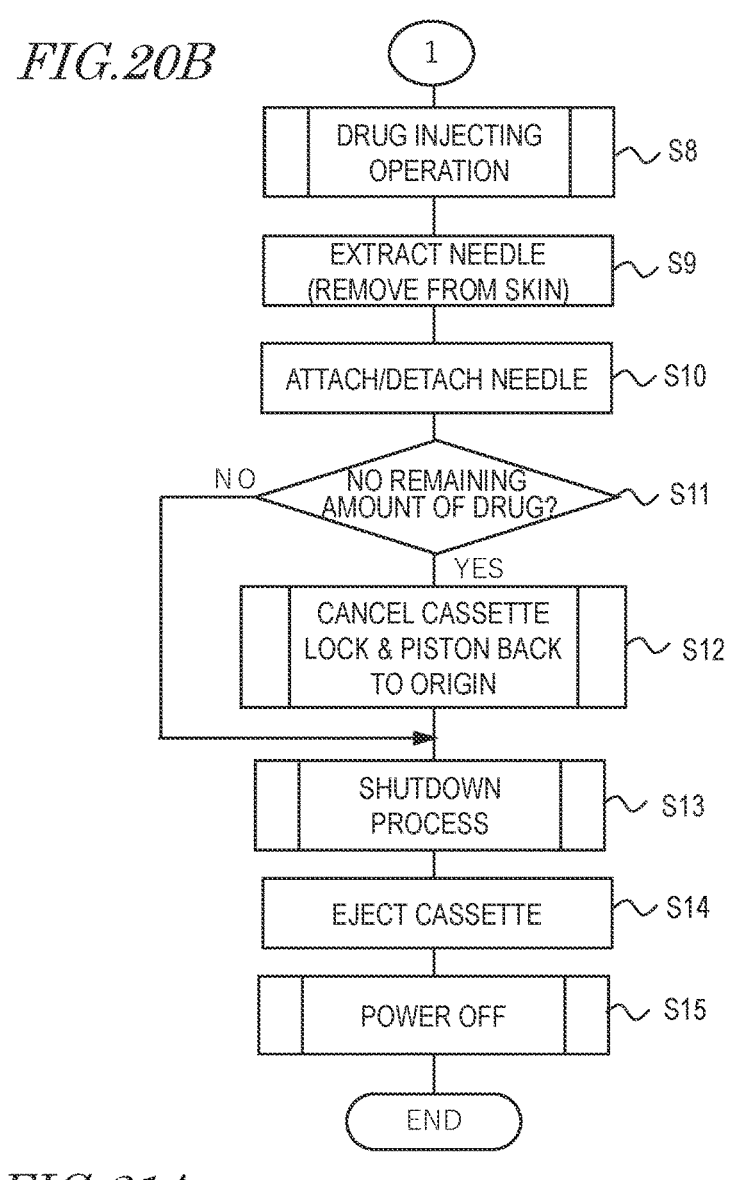

FIG. 20B is a flowchart describing procedures for manipulating the drug injection system.

Figure 21A:
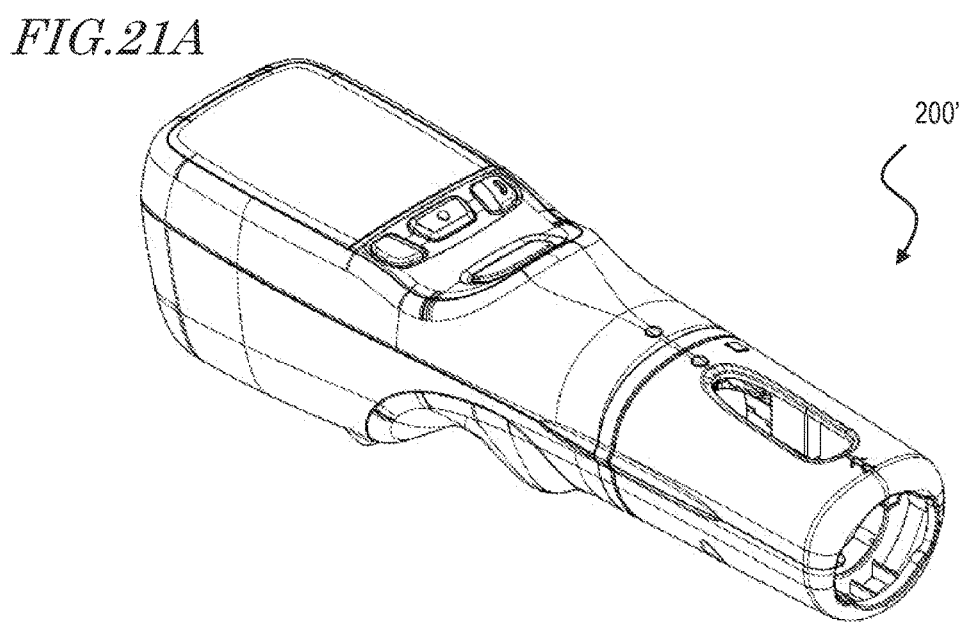

FIG. 21A is a perspective view showing the appearance of a full-automatic type drug injection device.

Figure 21B:
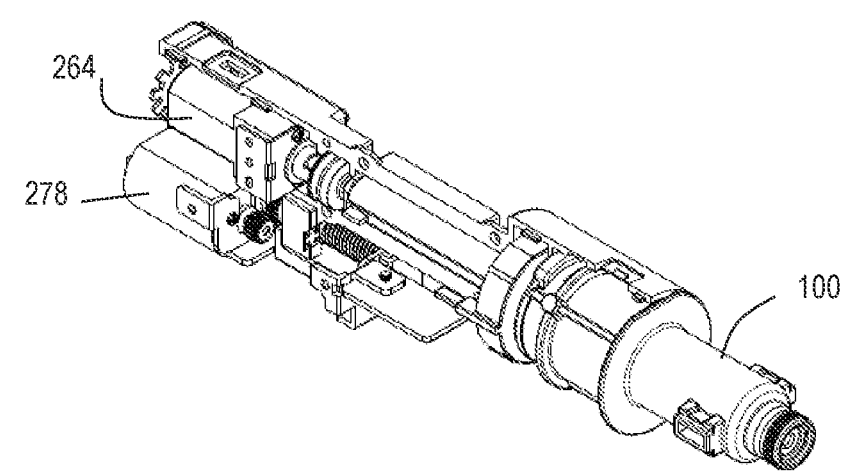

FIG. 21B is a perspective view showing the configuration of main portions of a full-automatic type drug injection device, from which the case has been removed.

Figure 21C:
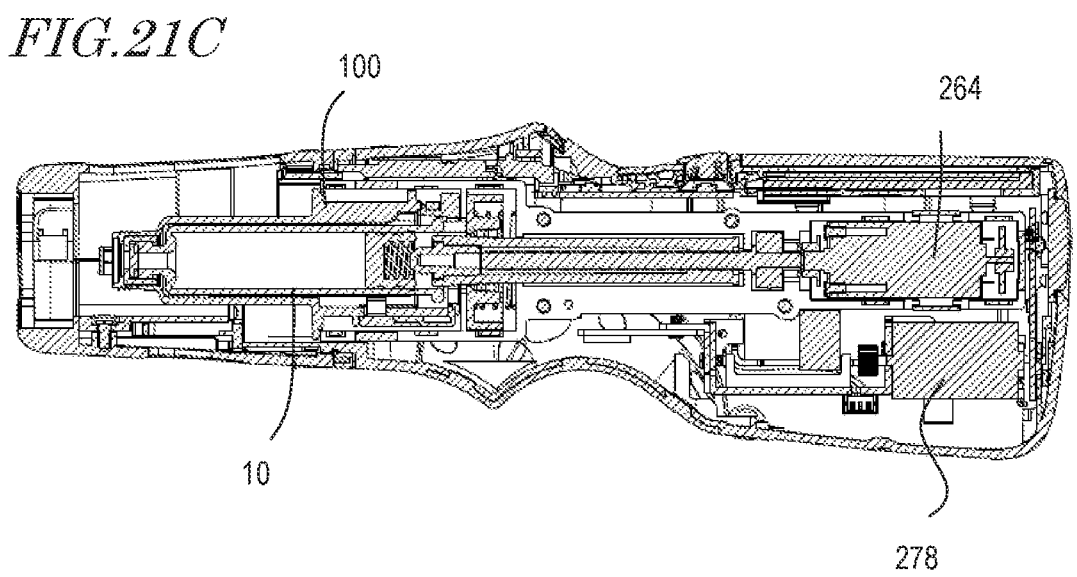

FIG. 21C is a cross-sectional view of a full-automatic type drug injection device.

Figure 22:
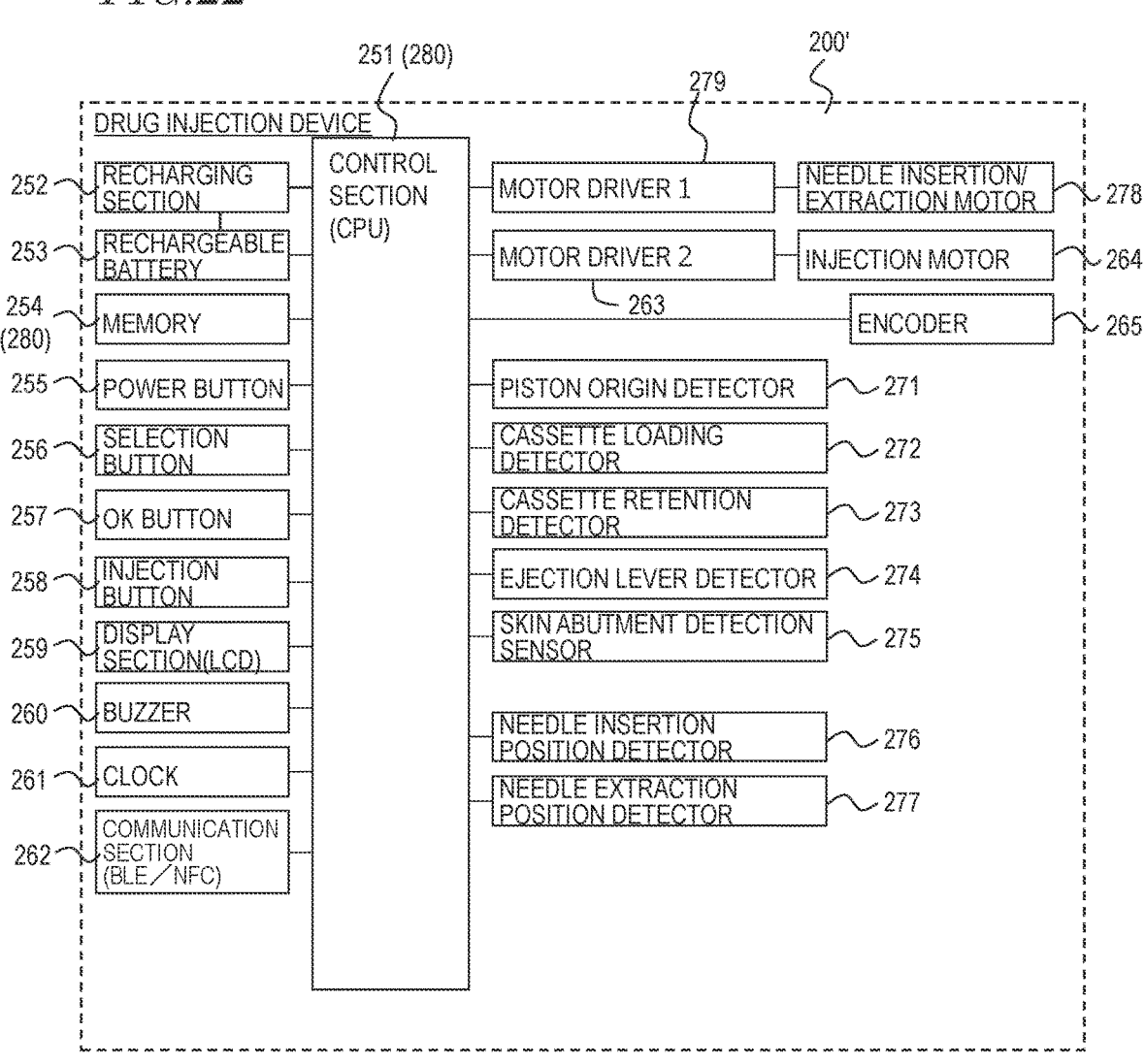

FIG. 22 is a block diagram showing an example configuration of the electric circuitry of the drug injection device shown in FIG. 21A, FIG. 21B, and FIG. 21C

Figure 23A:
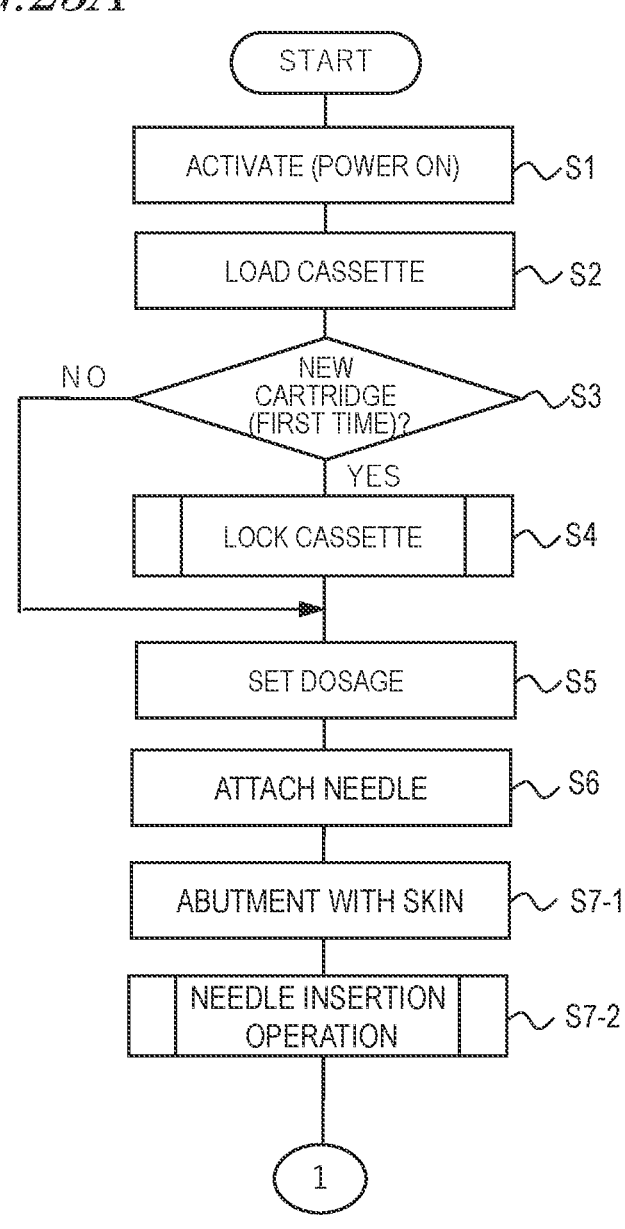

FIG. 23A is a flowchart describing procedures for manipulating the drug injection system described in FIG. 21A, FIG. 21B, and FIG. 21C.

Figure 23B:
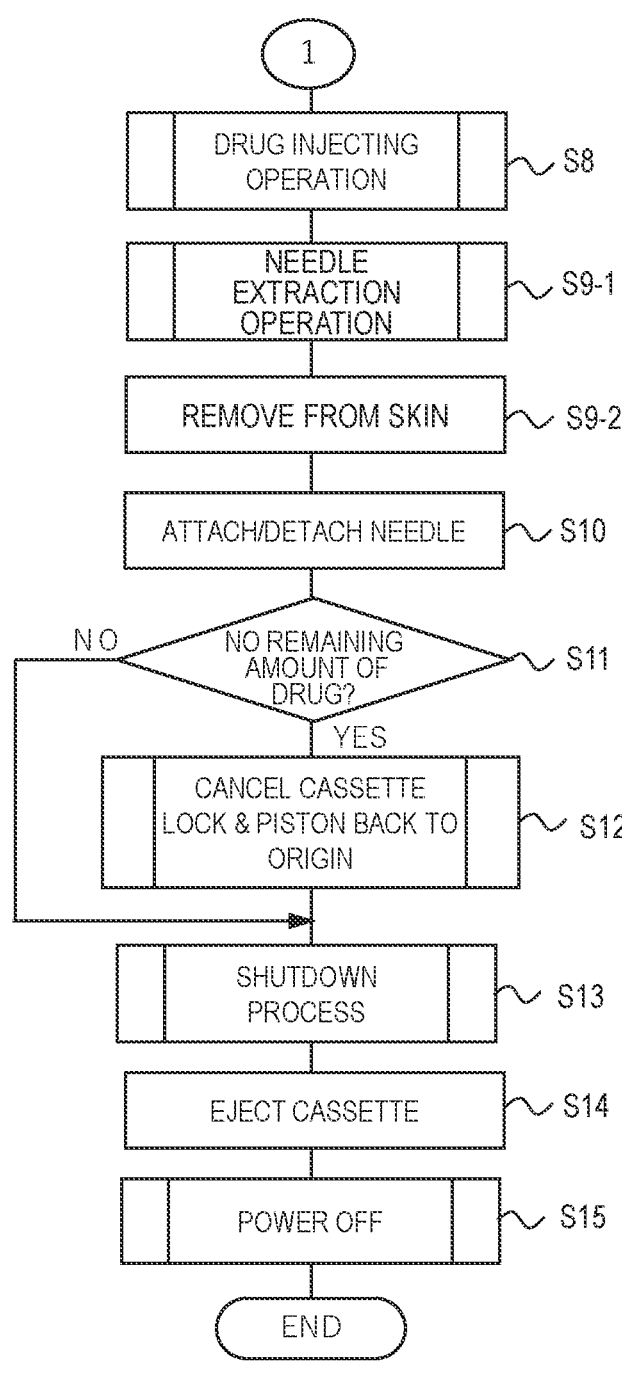

FIG. 23B is a flowchart describing procedures for manipulating the drug injection system described in FIG. 21A, FIG. 21B, and FIG. 21C.

DESCRIPTION OF EMBODIMENTS

In the case where a drug cartridge contains an amount of drug that would correspond to a plurality of shots, if the cassette is configured in such a manner that an unfinished drug cartridge (i.e., with some drug left therein) can be removed therefrom by the user, the removed unfinished drug cartridge may be inadvertently thrown away or lost, or the user may use a new drug cartridge while forgetting about the unfinished drug cartridge, for example. In the case where the drug injection device stores the remaining amount in the unfinished drug cartridge and keeps the piston at a position that is adapted to the remaining amount in the drug cartridge, exchanging the drug cartridge may result in a situation where the position of the piston and the amount of remaining drug in the drug cartridge may not properly correspond, such that the drug injection device cannot properly inject the drug. For example, if an unfinished drug cartridge is removed from the cassette, and a new unused drug cartridge is inserted in the cassette, the cassette being loaded (inserted) into the drug injection device may cause a gasket of the drug cartridge to be pressed until allowing the drug to be discharged, because the piston of the drug injection device has not been retracted.

On the other hand, the possibility of the drug cartridge being exchanged may be taken into consideration and the drug injection device may be configured so that the amount of remaining drug in the drug cartridge that has been inserted in the cassette or the gasket position is detected in controlling the piston. In this case, however, preparations for the injection are not complete until the piston is retracted prior to loading the cassette into the drug injection device, the position of the gasket of the drug cartridge in the loaded cassette is detected, and the piston is moved forward to the detected position. In other words, it takes time before the drug injection device becomes usable.

In view of such problems, the inventors of the present application have arrived at a cassette, a drug injection device, and a drug injection system which permit appropriate management of a drug cartridge. In outline, cartridges, drug injection devices, and drug injection systems according to the present disclosure may be as follows.

A cassette to be loaded to a drug injection device, the cassette comprising:

a cartridge holder including a first end at which an injection needle is attachable/detachable, a second end having a holder opening, and a holder columnar space being located between the first end and the second end and capable of accommodating a drug cartridge, wherein the drug cartridge includes: a cylinder including a first end at which the injection needle is insertable/extractable, a second end at which a cylinder opening is located, and a cylinder columnar space located between the first end and the second end; a drug placed in the cylinder columnar space; and a gasket being placed in the cylinder columnar space and capable of moving along a longitudinal direction of the cylinder columnar space;

a cassette cap being supported in the neighborhood of the second end of the cartridge holder so as to be capable of opening and closing the holder opening, the cassette cap including a first end having a cap opening that is opposed to the holder opening, a second end having a piston insertion opening, and a cap columnar space located between the first end and the second end, wherein, in an open state, the cassette cap allows the drug cartridge to be movable into and out of the holder columnar space of the cartridge holder, and, in a closed state, the cassette cap closes the holder opening to disallow the drug cartridge to be removed while allowing the gasket of the drug cartridge inserted into the holder columnar space to be exposed in the piston insertion opening; and a locking mechanism being located in the cap columnar space of the cassette cap and at least including a rotation lock unit that is supported so as to be capable of pivoting around an axis of the cap columnar space, wherein, the rotation lock unit has a shape that engages with a piston of the drug injection device for moving the gasket of the drug cartridge; and, while the drug cartridge is inserted in the cartridge holder and the cassette cap is in a closed state, the rotation lock unit pivots between a lock position for disallowing the cassette cap to open and an unlock position for allowing the cassette cap to open.

[Item 2]

The cassette of Item 1, wherein the rotation lock unit includes a unit throughhole having a cross-sectional shape that corresponds to a cross-sectional shape of a leading end portion of the piston perpendicular to an axis of piston; and, as the leading end portion of the piston is inserted from outside into the unit throughhole of the rotation lock unit and the piston rotates around an axis, the rotation lock unit pivots within the cassette cap.

[Item 3]

The cassette of Item 2, wherein a projected image of the unit throughhole of the rotation lock unit as projected on a plane perpendicular to an axis thereof differs between when the rotation lock unit is in the lock position and when the rotation lock unit is in the unlock position.

[Item 4]

The cassette of Item 3, wherein the rotation lock unit is unpivotable when the drug cartridge is not inserted in the cartridge holder and the cassette cap is in a closed state.

[Item 5]

The cassette of any of Items 2 to 4, wherein, the locking mechanism further includes:

a cassette button provided on the cartridge holder so as to be capable of being pressed; and a pair of engaging portions respectively provided on the cassette button and on the cassette cap, the engaging portions being capable of engaging with each other, wherein, when the rotation lock unit is in the unlock position, the cassette button is pressable so that the pair of engaging portions are disengaged from each other while the cassette button is pressed; and, when the rotation lock unit is in the lock position, the cassette button is unpressable and the pair of engaging portions are engaged with each other.

[Item 6]

The cassette of any of Items 2 to 5, further comprising an alarming section to inform that the rotation lock unit is in the lock position and/or the unlock position.

[Item 7]

The cassette of Item 6, wherein, the alarming section includes an alarming hole located on a side surface of the cassette cap and a colored region provided on a side surface of the rotation lock unit;

when the rotation lock unit is in the unlock position, the colored region is located outside the alarming hole; and, when the rotation lock unit is in the lock position, the colored region is located in the alarming hole.

[Item 8]

The cassette of Item 5, wherein, the rotation lock unit includes a cassette lock-ring, a cartridge stopper, and a spring disposed between the cassette lock-ring and the cartridge stopper;

the cassette lock-ring and the cartridge stopper compose the unit throughhole in a unitary manner, and are capable of rotating in the cap columnar space in a unitary manner, and, in the cap columnar space of the cassette cap, the cartridge stopper is urged toward the first end of the cassette cap and the cassette lock-ring is urged toward the second end of the cassette cap by the spring.

[Item 9]

The cassette of Item 8, wherein, the cassette cap includes a cap bump protruding into the cap opening;

the cartridge stopper includes an abutting surface to abut with the second end of the drug cartridge inserted in the cartridge holder while the cassette cap is closed, and a stopper bump located outside of the abutting surface; and, when the drug cartridge is not loaded in the cartridge holder and the cassette cap is closed, the stopper bump abuts with the cap bump to restrict pivoting of the rotation lock unit, and, when the drug cartridge is loaded in the cartridge holder and the cassette cap is closed, abutment between the second end of the drug cartridge and the abutting surface of the cartridge stopper causes the cartridge stopper to move backward toward the second end of the cassette cap, causes the stopper bump to become spaced apart from the cap bump, and enables the rotation lock unit to pivot.

[Item 10]

The cassette of Item 9, wherein, the cartridge stopper includes a first side surface subportion and a second side surface subportion;

in a plane perpendicular to the axis of the piston, a shortest distance between the second side surface subportion and the axis of the piston is shorter than a shortest distance between the first side surface subportion and the axis of the piston;

when the rotation lock unit is in the lock position, abutment between the first side surface subportion and the cassette button keeps the cassette button unpressable; and, when the rotation lock unit is in the unlock position, the cassette button is pressable until the cassette button abuts with the second side surface subportion.

[Item 11]

The cassette of Item 9 or 10, wherein, the cassette lock-ring and the cartridge stopper each have a ring portion;

the abutting surface and the stopper bump of the cartridge stopper are located on the ring portion;

one of the cassette lock-ring and the cartridge stopper includes at least one cutout extending in parallel to an axis of the rotation lock unit and a side surface of a barrel shape that is connected to the ring portion, and the other includes at least one protrusion connected to the ring portion, the at least one protrusion having a shape extending in parallel to the axis of the rotation lock unit and matching the at least one cutout; and, when the at least one protrusion is inserted in the at least one cutout, the cassette lock-ring and the cartridge stopper are capable of moving with respect to each other along the axial direction so that the respective ring portions thereof come closer or become farther apart.

[Item 12]

The cassette of Item 11, wherein, the ring portion of the cassette lock-ring includes a first ring engaging portion and a second ring engaging portion that are located on a surface opposed to an inner surface of the second end of the cassette cap;

on the inner surface of the second end of the cassette cap, the cassette cap includes a cap engaging portion that is capable of selectively engaging with the first ring engaging portion or the second ring engaging portion;

when the rotation lock unit is in the unlock position, the cap engaging portion engages with the first ring engaging portion; and when the rotation lock unit is in the lock position, the cap engaging portion engages with the second ring engaging portion.

[Item 13]

The cassette of any of Items 2 to 12, wherein a cross section of the unit throughhole has an I shape.

[Item 14]

The cassette of any of Items 2 to 13, wherein, the lock position and the unlock position of the rotation lock unit make an angle $\alpha$ around the axis of the cap columnar space in a plane perpendicular to the axis of the cap columnar space; and a cross section of the unit throughhole has a rotation symmetry other than $(360/\alpha)$-fold symmetric.

[Item 15]

A drug injection device comprising:

a case including a case opening and a cassette space to accommodate at least a portion of the cassette of any of Items 1 to 14;

a piston having an axis and capable of moving forward or backward along a direction parallel to the axis and rotating around the axis, wherein, when moving forward, the piston is capable of abutting with the gasket of the drug cartridge accommodated in the cassette that is placed in the cassette space and pushing in the gasket;

a piston driving mechanism to drive the piston in a direction of moving forward or backward and to rotate the piston around the axis; and a control device to control the piston driving mechanism, wherein, as the piston driving mechanism rotates the piston around the axis thereof, the piston causes the rotation lock unit of the cassette to pivot between the lock position and the unlock position.

[Item 16]

The drug injection device of Item 15, wherein the piston includes the leading end portion and a main body connected to the leading end portion, an outer edge of a projected shape of the main body as projected on a plane perpendicular to the axis of the piston is locate inward of an outer edge of a projected shape of the leading end portion.

[Item 17]

The drug injection device of Item 15 or 16, wherein, the piston driving mechanism includes:

a driving bump; and a first guide including a helical groove into which the driving bump is inserted, and a second guide including a linear groove into which the driving bump is inserted; and the driving bump or the first guide and second guide is/are located on a side surface of the piston.

[Item 18]

The drug injection device of Item 16, wherein, the driving bump is located on the side surface of the piston; and the second guide is located between the first guide and the cassette space.

[Item 19]

The drug injection device of Item 18, further comprising a piston guide having a hole into which at least a portion of the piston is insertable, wherein, the second guide is located on an inner side surface of the hole of the piston guide; and the first guide is located on the case.

[Item 20]

The drug injection device of Item 17, wherein, the piston driving mechanism further includes:

an injection motor to be driven under the control of the control device;

a drive rod having an external thread formed on a side surface, the drive rod being axially rotated by the injection motor; and an internal thread meshing with the external thread of the drive rod and being provided on the axis of the piston, wherein, as the drive rod rotates while the internal thread of the piston is meshed with the external thread of the drive rod, the piston is driven in the direction of moving forward or backward.

[Item 21]

The drug injection device of Item 20, wherein, as the drive rod rotates while the driving bump is inserted in the helical groove of the first guide, the piston causes the rotation lock unit of the cassette to pivot between the lock position and the unlock position.

[Item 22]

The drug injection device of Item 21, wherein, while the driving bump is inserted in the linear groove of the second guide, the piston does not rotate, and the rotation lock unit of the drug cartridge is maintained in the lock position.

[Item 23]

The drug injection device of any of Items 15 to 22, wherein the leading end portion of the piston has an I-cut shape.

[Item 24]

The drug injection device of any of Items 15 to 23, wherein, the control device stores a used amount or a number of administered doses of a drug, and, when the used amount or the number of administered doses is zero:

before a drug injecting operation, the control device controls the piston driving mechanism to move the piston in the direction of moving forward, and to rotate the piston so that the rotation lock unit of the cassette pivots from the unlock position to the lock position;

based on an instruction from an operator, the control device controls the piston driving mechanism to move the piston in the direction of moving forward but without rotating, to cause the gasket of the drug cartridge to move and allow the drug to be discharged from the injection needle; and, after discharging of the drug, the control device updates and stores the used amount or the number of administered doses of the drug, and ends operation without moving the piston in the direction of moving backward.

[Item 25]

The drug injection device of any of Items 15 to 23, wherein, the control device stores a used amount or a number of administered doses of a drug, and, when the used amount or the number of administered doses is not zero:

based on an instruction from an operator, the control device controls the piston driving mechanism to move the piston in the direction of moving forward but without rotating, to cause the gasket to move and allow the drug to be discharged from the injection needle;

after discharging of the drug, the control device updates and stores the used amount or the number of administered doses of the drug, and, when a remaining amount of the drug as calculated based on the updated used amount or number of administered doses of the drug is equal to or greater than a predetermined value, the control device ends operation without moving the piston in the direction of moving backward; and, when the remaining amount of the drug as calculated based on the updated used amount or number of administered doses of the drug is less than the predetermined value, the control device controls the piston driving mechanism to move the piston in the backward direction, and to rotate the piston so that the rotation lock unit of the cassette pivots from the lock position to the unlock position, and to move the piston to an initial position, and ends operation.

[Item 26]

A drug injection system comprising:

the cassette of any of Items 2 to 14; and the drug injection device of any of Items 15 to 25.

Examples of a cartridge, a drug injection device, and a drug injection system according to the present invention embodiment will now be described in detail with reference to the drawings. The drug injection system and the like to be described below are example embodiments, which are not limited to the configurations shown below, but permit various modifications. In the figures to be referred to in the following description, any reference sign that is not mentioned in the description may be omitted for the sake of simplicity.

(Configuration of the Drug Injection System)

[Outline of the Drug Injection System]

Figure 1A:
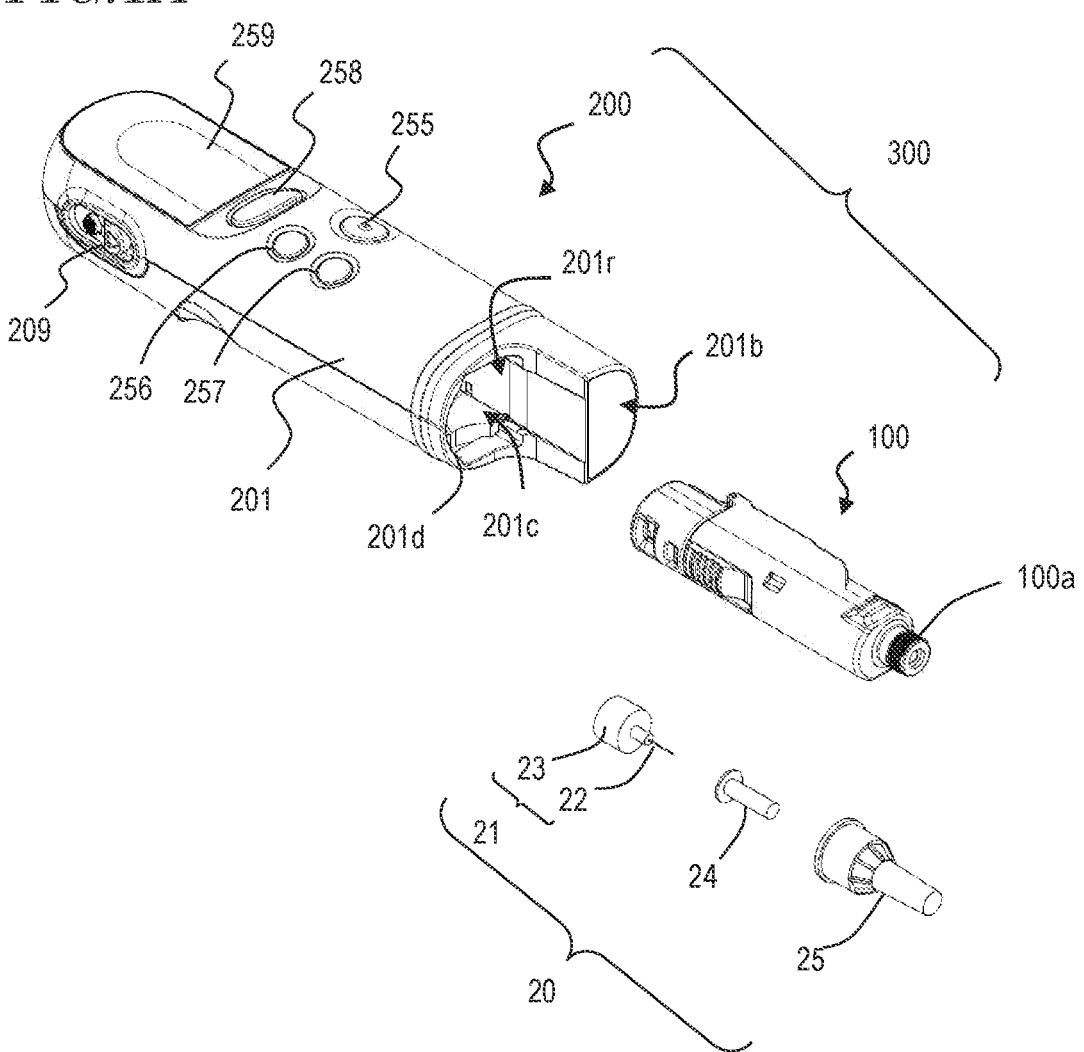
FIG. 1A is a perspective view showing the appearance of a drug injection system including a cassette and a drug injection device according to the present disclosure.
Figure 1B:
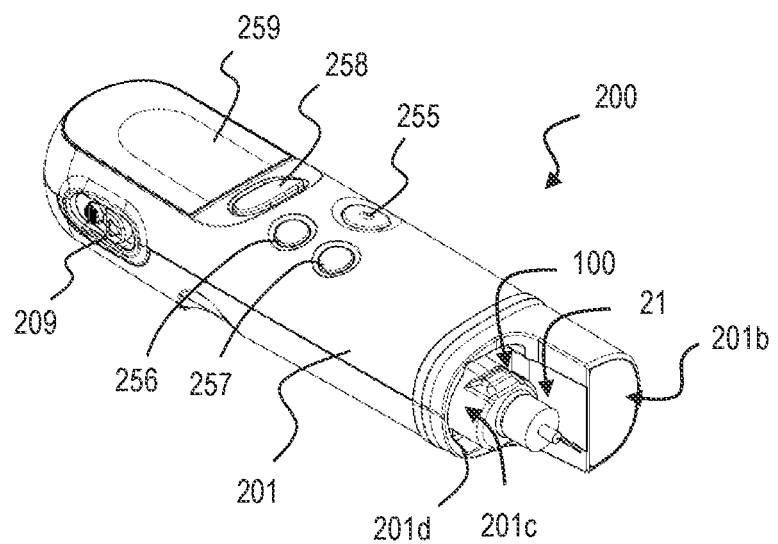
FIG. 1B is a perspective view of the drug injection device 200 to which the cassette has been loaded.
Figures 2, 3A:
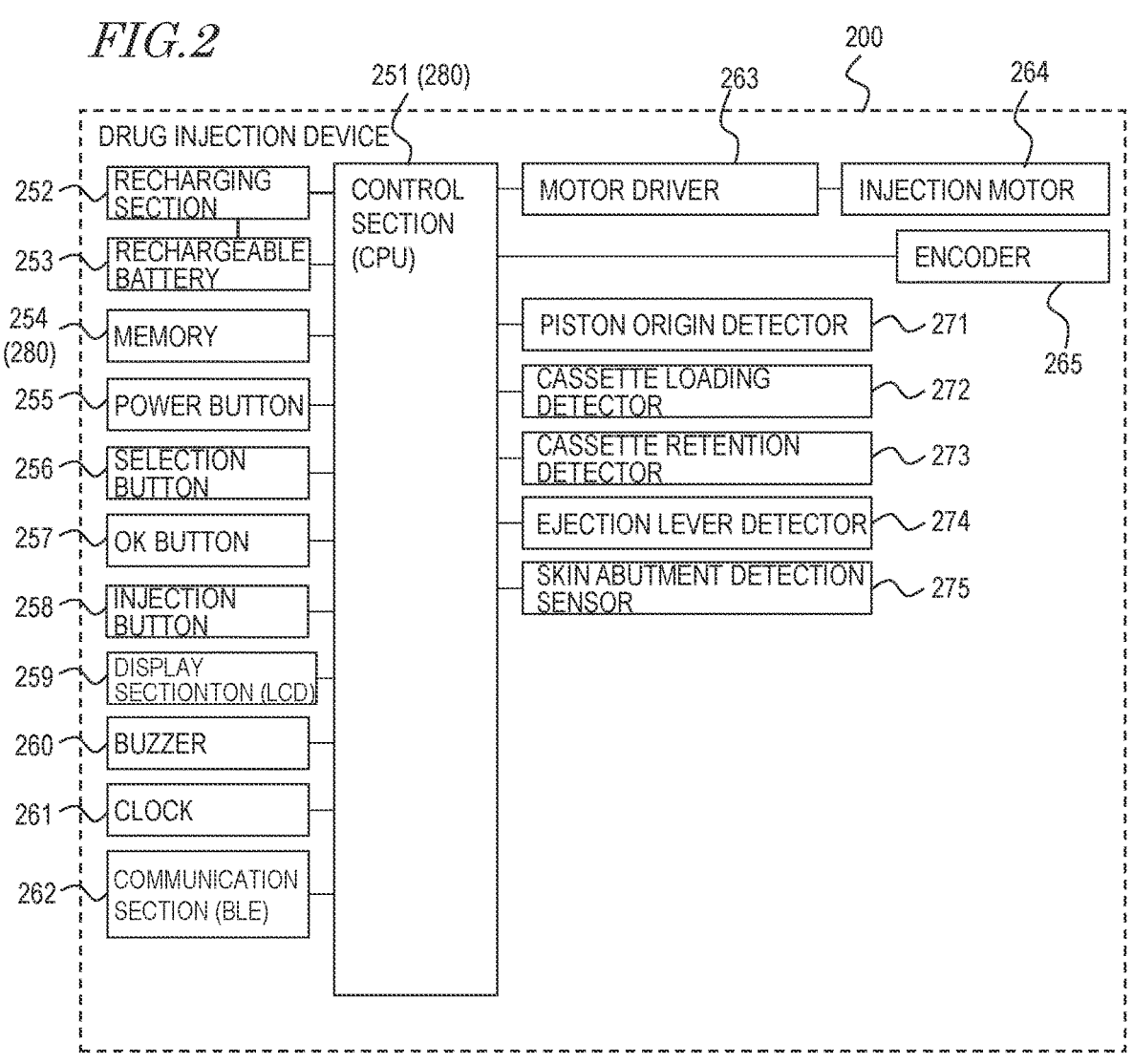
FIG. 2 is a block diagram showing an example configuration of electric circuitry of the drug injection device.
FIG. 3A is a perspective view showing the cassette accommodating a drug cartridge.

FIG. 1A is a perspective view showing the appearance of a drug injection system 300 including a cassette 100 and a drug injection device 200; and FIG. 1B is a perspective view of the drug injection device 200, to which the cassette 100 has been loaded. FIG. 2 is a block diagram showing an example configuration of electric circuitry of the drug injection device 200.

The drug injection device 200 includes an outer housing 201. The outer housing 201 may have a barrel shape with a thickness that allows an operator to grip it with one hand, for example, and has a recess 201r at one end of the longitudinal direction of the outer housing 201. The outer housing 201 has a skin abutment surface 201b at a position adjacent to the recess 201r. At the bottom of the recess 201r, a case opening 201d is located through which the cassette 100 is insertable, such that a cassette space 201c being located in the outer housing 201 and capable of accommodating at least a portion of the cassette 100 connects to the case opening 201d. In the present embodiment, the barrel shape of the outer housing 201 is composed of two essentially flat surfaces and two side faces interconnecting the two flat surfaces, having a cross section (perpendicular to the longitudinal direction) which is an oblong circular shape. However, the shape of the outer housing 201 is not limited thereto, and may have a cylindrical shape or a prismatic shape.

The cassette 100 has a holder columnar space 110c in which a drug cartridge 10 can be accommodated. The drug cartridge 10 is not shown in FIG. 1A and FIG. 1B because it is accommodated in the holder columnar space 110c. The cassette 100 has a first end 100a to/from which an injection needle 21 can be attached or detached. The injection needle 21 is disposable, and may be treated separately, e.g., as a needle unit 20, from the cassette 100 when not in use.

The needle unit 20 includes the injection needle 21, a needle cap 24, and a needle case 25. The injection needle 21 includes a needle 22 and an interconnecting section 23 which supports the needle 22, the interconnecting section 23 being detachably mounted to the first end 100a of the cassette 100. The needle cap 24 has a barrel shape covering the needle 22, such that the needle case 25 accommodates the injection needle 21 while the needle 22 is covered by the needle cap 24.

In the present specification, regarding the cassette 100 or the drug injection device 200 having the cassette 100 loaded thereto, any movement of a component element in the direction of the injection needle 21 will be referred to as moving "forward" and any movement in the opposite direction as moving "backward".

On the surface of the outer housing 201, the drug injection device 200 has a power button 255, a selection button 256, an OK button 257, an injection button 258, an ejection lever 209, and a display section 259. When using the drug injection system 300, the power button 255 is pressed to activate the drug injection device 200, in response to which the display section 259 displays a procedure for manipulating the drug injection device 200, information on the drug in the drug cartridge 10 within the loaded cassette 100, injection history, and the like.

The cassette 100 is loaded to the drug injection device 200. While remaining in the needle unit 20, the interconnecting section 23 of the injection needle 21 is mounted to the first end 100a, and then the needle case 25 and the needle cap 24 are removed. In this state, the needle 22 is exposed, such that the tip end of the needle 22 protrudes from the skin abutment surface 201b of the outer housing 201. After the selection button 256 and the OK button 257 are pressed as appropriate to determine the operation of the drug injection device 200, a drug injecting operation is performed. The drug injection device 200 according to the present embodiment is a semi-automatic type, such that needle insertion and needle extraction are performed manually, i.e., by the operator. Accordingly, as the operator presses the drug injection device 200 against and in contact with the skin, the injection needle 21 become inserted into the skin to a predetermined depth. Then, as the injection button 258 is pressed, a predetermined amount of drug is injected from the drug cartridge 10.

After drug injection is completed, the operator releases the drug injection device 200 from the skin, and the injection needle 21 becomes pulled out of the skin. Thereafter, the ejection lever 209 is manipulated so as to eject the cassette 100 from the drug injection device 200.

As shown in FIG. 2, the drug injection device 200 includes: a control section 251 including an arithmetic unit such as a CPU; a rechargeable battery 253 as a power source; a recharging section 252 for recharging the rechargeable battery 253; a memory 254 storing a computer program, data, etc.; and a clock 261. The control section 251 and the memory 254 constitute a control device 280, such that the control section 251 reads a program that is stored in memory 254 and controls the component elements shown in FIG. 2 in accordance with the procedures in the computer program. The procedures in the computer program will be illustrated in the following description and flowcharts given in the attached drawings. The drug injection device 200 may further include a buzzer 260 to alarm the operator with sounds.

The drug injection device 200 further includes an injection motor driver 263, an injection motor 264, and an encoder 265. The injection motor driver 263, the injection motor 264, and the encoder 265 constitute parts of a piston driving mechanism, as will be described below.

In addition to the above, the drug injection device 200 includes various detectors to detect the statuses of various elements of the drug injection device 200. Specifically, the drug injection device 200 includes a piston origin detector 271, a cassette loading detector 272, a cassette retention detector 273, an ejection lever detector 274, and a skin abutment detection sensor 275.

The drug injection device 200 may further include a communication section 262. The communication section 262 may perform exchange of information with the exterior via infrared communication or wireless communication, etc., for example. Specifically, the communication section 262 may be a transmitter/receiver that utilizes a short-range wireless communication standard, e.g., BLE (Bluetooth Low Energy; Bluetooth is a registered trademark). For example, the operator may cause the time of using the drug injection device 200, the kind of drug, the injected amount, and the like to be stored to the memory 254 during use, and by using the communication section 262, transmit such information to an external device, e.g., a mobile device such as a smartphone or a tablet terminal, or a dedicated device for managing the drug injection device 200, at a predetermined timing.

[Structure of the Drug Cartridge 10 and the Cassette 100]

Figure 3B:
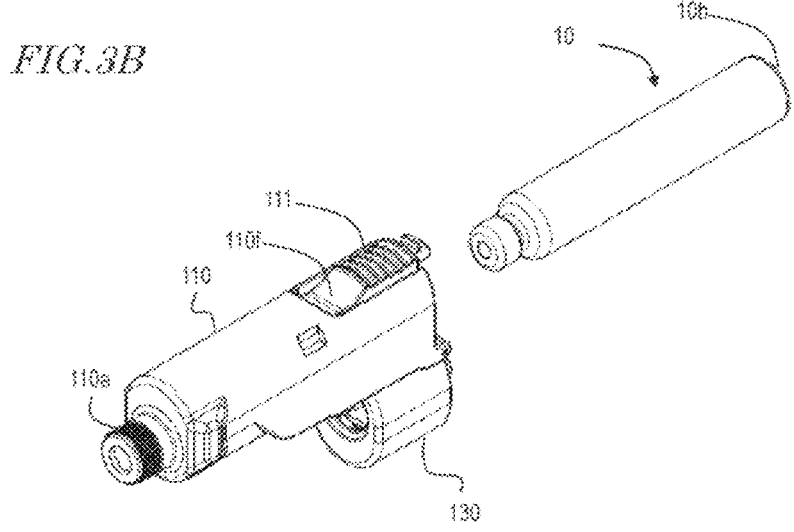
FIG. 3B is a perspective view showing a state where the drug cartridge has been removed from the cassette.
Figure 4A:
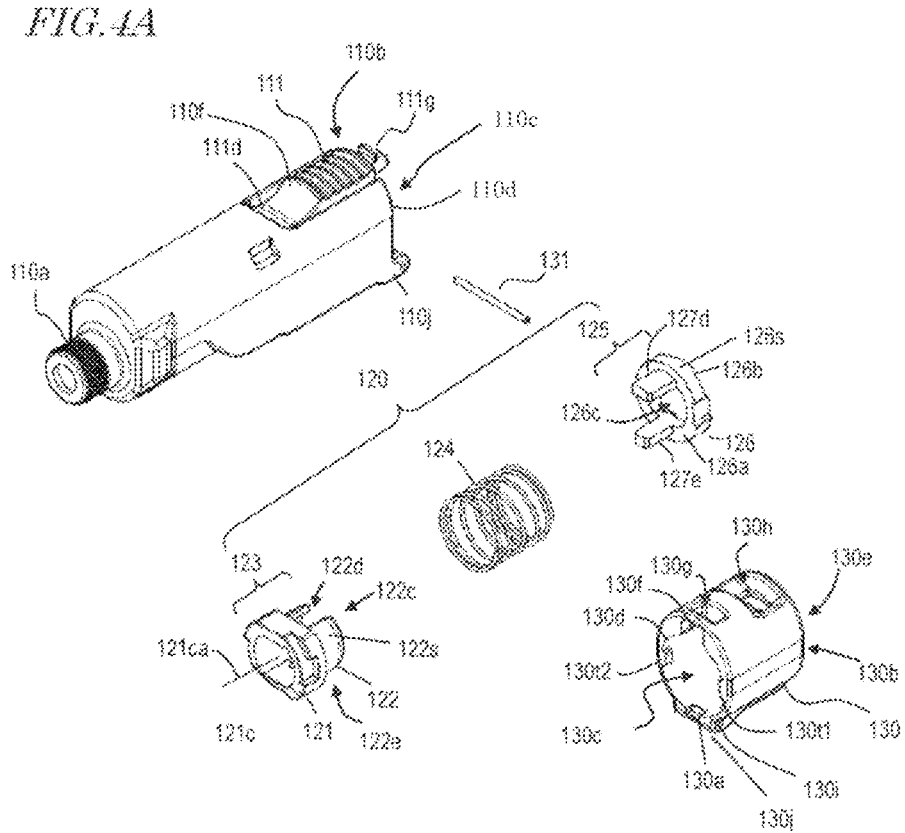
FIG. 4A is an exploded perspective view of the cassette.
Figures 4B, 4C, 5A:
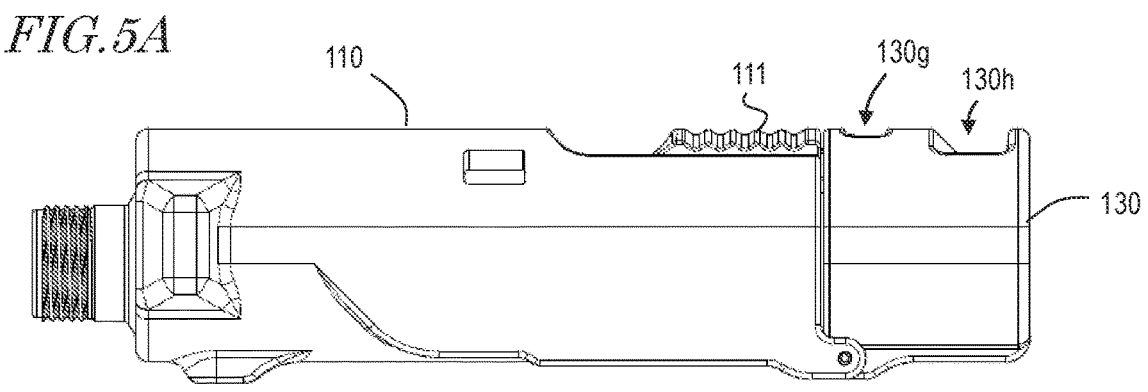
FIG. 4B is a unit-by-unit exploded perspective view of the cassette as viewed in one direction along the longitudinal direction.
FIG. 4C is a unit-by-unit exploded perspective view of the cassette as viewed in another direction along the longitudinal direction.
FIG. 5A is a side view of the cassette.

FIG. 3A is a perspective view showing the cassette 100 accommodating the drug cartridge 10; and FIG. 3B is a perspective view showing a state where the drug cartridge 10 has been removed from the cassette 100. FIG. 4A is an exploded perspective view of the cassette 100; and FIG. 4B and FIG. 4C are unit-by-unit exploded perspective views of the cassette 100 as viewed in two directions. FIG. 5A is a side view of the cassette 100; and FIG. 5B and FIG. 5C are cross-sectional views of the cassette 100.

<Drug Cartridge 10>

Figure 5B:
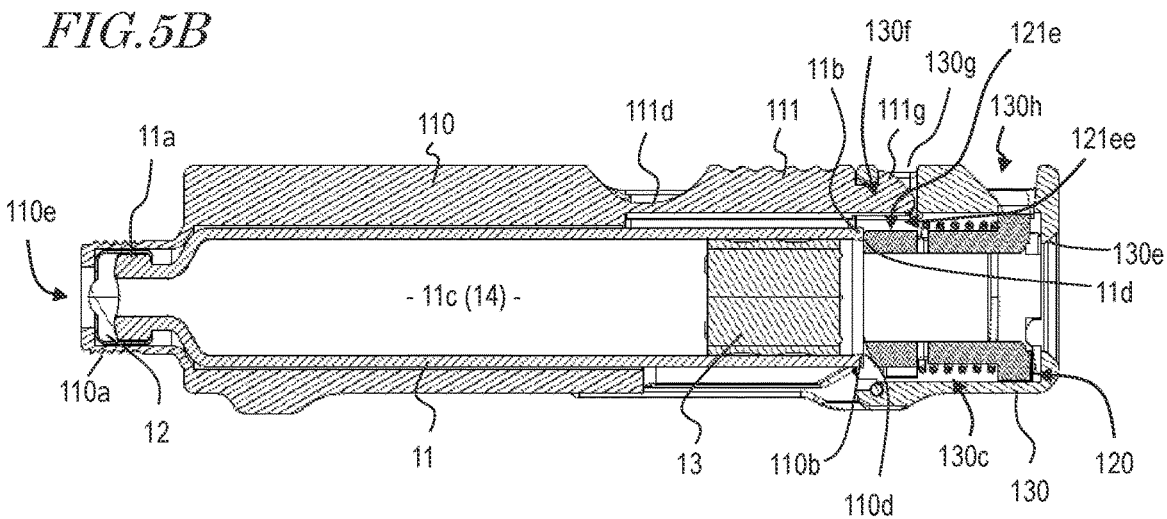
FIG. 5B is a cross-sectional view of the cassette.
Figure 5C:
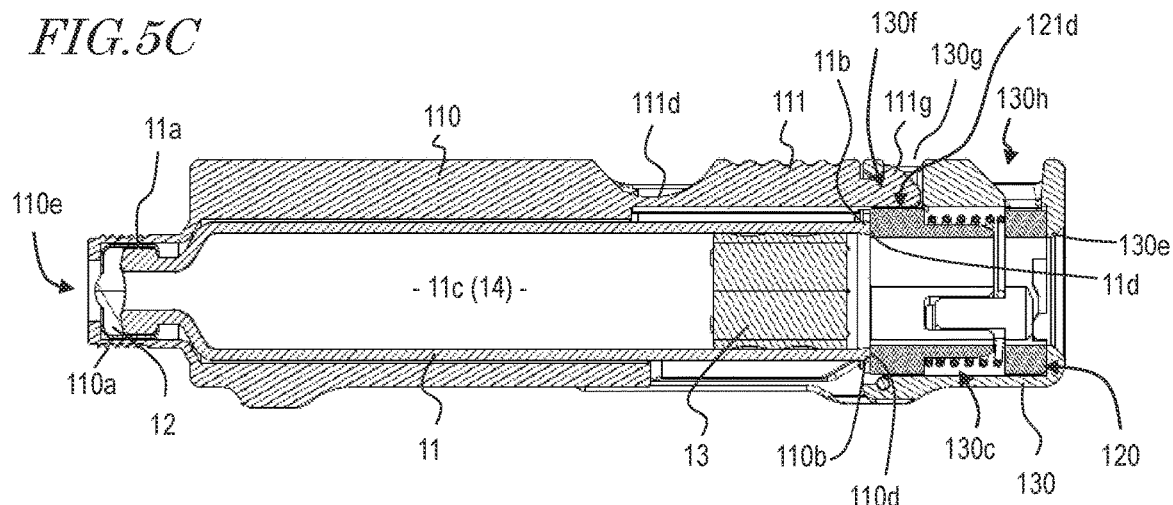
FIG. 5C is a cross-sectional view of the cassette.

As is shown in the cross sections of FIG. 5B and FIG. 5C, the drug cartridge 10 includes a cylinder 11 having a first end 11a and a second end 11b that are spaced apart along the longitudinal direction and a cylinder columnar space 11c that is located between the first end 11a and the second end 11b. The needle 22 of the injection needle 21 can be inserted to or extracted from the first end 11a. For example, the cylinder 11 has an outer shape which is thinner at the first end 11a so as to result in a smaller cross section (taken perpendicular to the longitudinal direction of the cylinder columnar space 11c) at the first end 11a, and a rubber cylinder cap 12 is used at the first end 11a to seal the opening of the cylinder columnar space 11c at the first end 11a side. At the second end 11b, the cylinder 11 has a cylinder opening 11d which is connected to the cylinder columnar space 11c.

The drug cartridge 10 further includes a gasket 13, which is inserted through the cylinder opening 11d into the cylinder columnar space 11c and is supported by the inner wall of the cylinder 11 so as to be capable of moving along the longitudinal direction.

The first end 11a and the second end 11b of the cylinder columnar space 11c are closed by the cylinder cap 12 and the gasket 13, and a drug 14 is sealed within the closed cylinder columnar space 11c.

<Cassette 100>

As shown in FIG. 4A, FIG. 4B, and FIG. 4C, the cassette 100 includes a cartridge holder 110, a rotation lock unit 120, and a cassette cap 130.

<<Cartridge Holder 110>>

The cartridge holder 110 accommodates the drug cartridge 10. The cartridge holder 110 includes a first end 110a at which the injection needle is attachable/detachable, a second end 110 having a holder opening 110d, and a holder columnar space 110c being located between the first end 110a and the second end 110b and capable of accommodating the drug cartridge 10. As shown in FIG. 5B and FIG. 5C, the cartridge holder 110 has an aperture 110e at the first end 110a, such that the cylinder cap 12 of the drug cartridge 10 accommodated in the holder columnar space 110c is exposed within the aperture 110e. The first end 110a is configured so that the injection needle 21 is attachable/detachable. For example, the cartridge holder 110 has an external thread on the side surface at the first end 110a, and an internal thread is provided on the inner side of the interconnecting section 23 of the injection needle 21.

When the interconnecting section 23 of the injection needle 21 is mounted to the first end 110a of the cartridge holder 110, the rear end of the needle 22 is inserted in the cylinder cap 12, so that the aperture of the needle 22 communicates with the cylinder columnar space 11c.

As shown in FIG. 4A, in the present embodiment, the cartridge holder 110 includes an opening 110f made in the side surface, and a cassette button 111 disposed in the opening 110f. At the first end 110a side of the longitudinal direction, the cassette button 111 is elastically connected by a connecting portion 111d to the side surface of the cartridge holder 110 located at the outer edge of the opening 110f. Moreover, the cartridge holder 110 includes an engaging portion 111g that is located at the second end 110b side of the longitudinal direction of the cassette button 111. In the present embodiment, the engaging portion 111g is a hook having a tab, the tab being oriented outward from an axis that is parallel to the longitudinal direction of the holder columnar space 110c. As the operator presses the cassette button 111, the engaging portion 111g is also pushed down. The cassette button 111 and the engaging portion 111g constitute parts of a locking mechanism to be described below.

At the second end 110b of the cartridge holder 110, a pair of holder supports 110j for supporting a shaft 131 are provided. On the side surface of the cartridge holder 110, a pair of lock recesses 110g are made (FIG. 4B).

<<Cassette Cap 130>>

The cassette cap 130 creates an open state or a closed state of the holder opening 110d of the cartridge holder 110. For this purpose, in the neighborhood of the second end 110b of the cartridge holder 110, the cassette cap 130 is supported so as to be capable of opening and closing the holder opening 110d. The cassette cap 130 includes a first end 130a having a cap opening 130d that is opposed to the holder opening 110d; a second end 130b having a piston insertion opening 130e; and a cap columnar space 130c located between the first end 130a and the second end 130b. As will be described below, the rotation lock unit 120 is accommodated in the cap columnar space 130c. A button space 130f lies adjacent to the cap columnar space 130c. While the cassette cap 130 keeps the holder opening 110d of the cartridge holder 110 closed, the engaging portion 111g of the cassette button 111 is located in the button space 130f.

The cassette cap 130 includes at least one cap bump protruding into the cap opening 130d. For example, in the present embodiment, the cassette cap 130 includes cap bumps 130t1 and 130t2. Within the cap opening 130d, the cap bump 130t1 and the cap bump 130t2 are located on opposite sides from each other across the center of cap opening 130d. In the present embodiment, in terms of their length along the peripheral direction fitting along the cap opening 130d, the cap bump 130t1 is longer than the cap bump 130t2.

When the cassette cap 130 is open, the holder opening 110d is not covered by the cassette cap 130, so that the drug cartridge 10 is movable into and out of the holder columnar space 110c of the cartridge holder 110. When the cassette cap 130 is closed, the holder opening 110d is covered by the cassette cap 130. Therefore, the drug cartridge 10 accommodated in the holder columnar space 110c cannot be removed from the cartridge holder 110. When the cassette cap 130 is closed, the gasket 13 of the drug cartridge 10 accommodated in the holder columnar space 110c is exposed in the piston insertion opening 130e.

The cassette cap 130 includes an alarming aperture 130h and an engaging portion 130g located on the side surface. With a colored region 126r of the rotation lock unit 120 described below, the alarming aperture 130h constitutes an alarming section to let the operator know whether the rotation lock unit 120 is in a lock position or an unlock position. The engaging portion 130g is shaped so as to be capable of engaging with the engaging portion 111g of the cassette button 111. In the present embodiment, the engaging portion 130g is an opening that is capable of engaging with the hook-shaped engaging portion 111g of the cassette button 111. When the engaging portion 111g of the cassette button 111 and the engaging portion 130g of the cassette cap 130 are engaged, the cassette cap 130 cannot open.

On the side surface of the cassette cap 130, a cap support 130j is provided having an aperture 130i into which the shaft 131 is inserted. The shaft 131 inserted in the aperture 130i is supported by the holder supports 110j of the cartridge holder 110 located at both ends of the aperture 130i. As a result, the cassette cap 130 is supported by the cartridge holder 110 so as to be capable of pivoting around the shaft 131 as an axis. On the inner surface of the second end 130b of the cassette cap 130, the cap engaging portion 130k of the cassette cap 130 is located (FIG. 4B).

<<Rotation Lock Unit 120>>

Figure 6A:
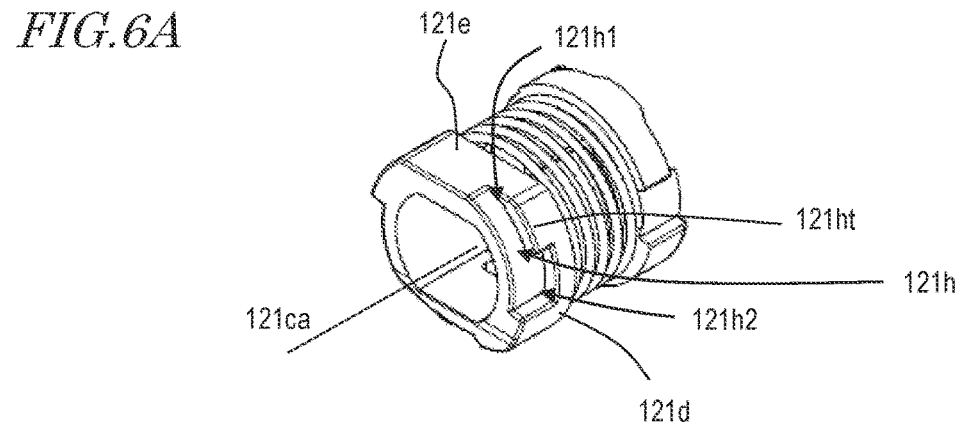
FIG. 6A is a perspective view of a rotation lock unit.
Figure 6B:
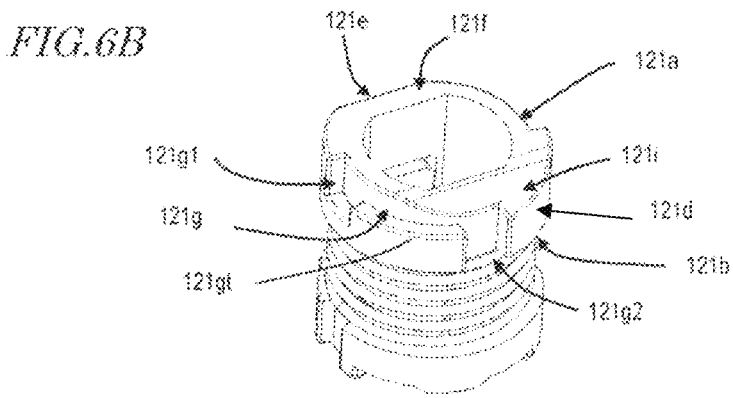
FIG. 6B is a perspective view of the rotation lock unit.

The rotation lock unit 120 is accommodated in the cassette cap 130, and constitutes a locking mechanism together with the cassette button 111 of the cartridge holder 110 and the engaging portion 130g of the cassette cap 130. The locking mechanism locks the cassette cap 130 so that the cassette cap 130 cannot be opened when the cassette cap 130 is in a closed state. The rotation lock unit 120 includes a cartridge stopper 123, a cassette lock-ring 125, and a spring 124 disposed between the cartridge stopper 123 and the cassette lock-ring 125. FIG. 6A and FIG. 6B are perspective views showing the rotation lock unit 120 as viewed from different angles.

The cartridge stopper 123 includes a ring portion 121 having a throughhole 121c. The ring portion 121 includes a first end 121a and a second end 121b. As shown in FIG. 6B, at the first end 121a, the cartridge stopper 123 includes: an abutting surface 121f which abuts with the second end 10b of the drug cartridge 10 inserted in the cartridge holder 110; and a sloped surface 121i. The abutting surface 121f is perpendicular to the axis 121ca of the throughhole 121c, whereas the sloped surface 121i is tilted toward the outer periphery from the axis 121ca. At the second end 121b of the ring portion 121, a cylindrical portion 122, described below, is connected. As will be described below, the throughhole 121c includes a columnar space that has a cross-sectional shape corresponding to a projected shape of the leading end portion of a piston 210 of the drug injection device 200 on a plane which is perpendicular to the axis of the piston 210.

The ring portion 121 of the cartridge stopper 123 includes a first side surface subportion 121d and a second side surface subportion 121e. In a plane perpendicular to the axis 121ca of the throughhole 121c, the shortest distance between the second side surface subportion 121e and the axis 121ca of the throughhole 121c is shorter than the shortest distance between the first side surface subportion 121d and the axis 121ca of the throughhole 121c. In the present embodiment, the ring portion 121 has a shape resulting from cutting a short barrel or a ring having a cross section (taken perpendicular to the axis 121ca of the throughhole 121c) with a circular outer shape horizontally with respect to the axis 121ca, such that the removed portion defines the second side surface subportion 121e and that the remaining side surface of the barrel or ring defines the first side surface subportion 121d. Therefore, in the present embodiment, the second side surface subportion 121e is a flat surface. However, so long as the axis 121ca and the first side surface subportion 121d and second side surface subportion 121e satisfy the aforementioned relationship, the shape of the ring portion 121 is not limited to this example, and the second side surface subportion 121e may be a curved surface.

The ring portion 121 includes grooves 121g and 121h in the first side surface subportion 121d. The groove 121g and the groove 121h are each in contact with the abutting surface 121f at the first end 121a; the abutting surface 121f has no side surface; and the groove 121g and the groove 121h each have an opening also on the abutting surface 121f. The groove 121g is further in contact with the sloped surface 121i, the groove 121g having an opening from the abutting surface over to the sloped surface 121i. The end 121h1 of the groove 121h is connected to the second side surface subportion 121e.

The width of the grooves 121g and 121h along the axis 121ca is locally narrower. Specifically, the groove 121h has a narrower width at the end 121h1 side, and a broader width at the end 121h2 side. Therefore, when the groove 121h is viewed from the abutting surface 121f (first end 121a), the stopper bump 121ht is located near the end 121h1 outside of the abutting surface 121f.

The groove 121g has a broader width at the end 121g1 and the end 121g2, and a narrower width in between. Therefore, when the groove 121g is viewed from the abutting surface 121f, the stopper bump 121gt is located outside of the abutting surface 121f and in between the end 121g1 and the end 121g2. At the end 121g2, the groove 121g preferably also has an opening in the second end 121b. Moreover, it is preferable that the end 121g2 of the groove 121g is located an on opposite side from the second side surface subportion 121e, across the axis 121ca.

As shown in FIG. 4A, the cartridge stopper 123 includes a cylindrical portion 122 that is connected to the second end 121b of the ring portion 121. The cylindrical portion 122 includes an internal space 122c, the internal space 122c being connected to the throughhole 121c of the ring portion 121. The cylindrical portion 122 includes a side surface 122s, the side surface 122s having at least one cutout that extends in parallel to the axis of the internal space 122c. In the present embodiment, the cylindrical portion 122 includes cutouts 122d and 122e. The cutout 122d and the cutout 122e are placed essentially symmetrical with respect to the axis of the cylindrical shape.

The cassette lock-ring 125 includes a ring portion 126 that has a throughhole 126c. As shown in FIG. 4C, the ring portion 126 includes a first end 126a and a second end 126b, and a surface 126f that is located at the second end 126b. The surface 126f is opposed to the inner surface of the second end 130b of the cassette cap 130. On the surface 126f of the cassette cap 130, a first ring engaging portion 126g1 and a second ring engaging portion 126g2 are provided. The cap engaging portion 130k of the cassette cap 130 selectively engages with one of the first ring engaging portion 126g1 and the second ring engaging portion 126g2 of the cassette lock-ring 125.

As shown in FIG. 4B, the cap engaging portion 130k is one of a recess or a bump to engage with a recess, for example, while the first ring engaging portion 126g1 or the second ring engaging portion 126g2 are the other of a recess or a bump to engage with a recess. The cap engaging portion 130k and the first ring engaging portion 126g1 or the second ring engaging portion 126g2 may engage with each other through a combination of shapes other than a combination of a recess and a bump. In the present embodiment, the first ring engaging portion 126g1 and the second ring engaging portion 126g2 are each formed in two regions between which the throughhole 126c is interposed.

A colored region 126r is provided on the side surface 126s of the ring portion 126. Also, a groove 126h1 and a groove 126h2 are provided on the side surface 126s. The groove 126h1 and the groove 126h2 each reach the first end 126a and the second end 126b, thus also having openings in the first end 126a and the second end 126b. In terms of their length along the peripheral direction of the side surface 126s, the groove 126h1 and the groove 126h2 respectively correspond to the lengths of the cap bumps 130t1 and 130t2 provided in the cap opening 130d of the cassette cap 130 along the peripheral direction. In other words, the length of the groove 126h1 along the peripheral direction is greater than the length of the groove 126h2 along the peripheral direction.

The cassette lock-ring 125 includes at least one protrusion that is connected to the first end 126a of the ring portion 126. In the present embodiment, the cassette lock-ring 125 includes protrusions 127d and 127e. The protrusions 127d and 127e have a flat strip shape, and are parallel to the axis of the throughhole 126c. The protrusions 127d and 127e have shapes corresponding to the cutouts 122d and 122e made in the side surface 122s of the cylindrical portion 122 of the cartridge stopper 123.

The spring 124 may be e.g. a coil spring, having an inner diameter that allows insertion of the cylindrical portion 122 of the cartridge stopper 123.

The rotation lock unit 120 is constructed by assembling the cartridge stopper 123, the spring 124, and the cassette lock-ring 125. Specifically, the spring 124 is inserted into the cylindrical portion 122 of the cartridge stopper 123, and the protrusions 127d and 127e of the cassette lock-ring 125 are inserted in the cutouts 122d and 122e made in the side surface 122s of the cylindrical portion 122 of the cartridge stopper 123. As a result, the ring portion 121 of the cartridge stopper 123 and the ring portion 126 of the cassette lock-ring 125 are urged in mutually opposite directions by the spring 124. In the rotation lock unit 120, the throughhole 121c of the cassette lock-ring 125, the internal space 122c of the cylindrical portion 122, and the throughhole 126c of the ring portion 126 of the cassette lock-ring 125 compose, in a unitary manner, one unit throughhole 120c. The unit throughhole 120c has a cross-sectional shape that corresponds to a cross-sectional shape of a leading end portion 211 of the piston 210 (provided in the drug injection device 200) perpendicular to the axis of the piston 210. In other words, in a plane perpendicular to the axis of the unit throughhole 120c, the rotation lock unit 120 has an opening corresponding to a cross-sectional shape perpendicular to the axis of the piston 210. As shown in FIG. 6A, FIG. 6B, etc., in the present embodiment, the unit throughhole 120c has an I-cut shape resulting from cutting a geometric cylinder at two planes that are parallel to its axis. In other words, the unit throughhole 120c has a cross section with a shape resulting from removing two parallel arcs from a circle. This is because, as will be described below, the leading end portion 211 of the piston 210 has an I-cut shape. However, the shape of the unit throughhole 120c is not limited thereto, and the unit throughhole 120c may have other shapes as will be described below.

Figure 7:
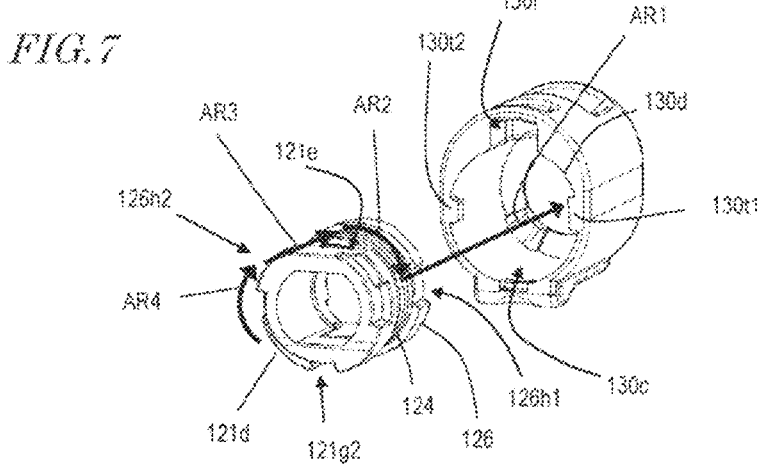
FIG. 7 is a perspective view describing a procedure of accommodating the rotation lock unit in a cassette cap.

The rotation lock unit 120 is retained in the cap columnar space 130c of the cassette cap 130. As described above, after the cartridge stopper 123, the spring 124, and the cassette lock-ring 125 are assembled to compose the rotation lock unit 120, as shown in FIG. 7, the rotation lock unit 120 is inserted into the cap columnar space 130c through the cap opening 130d, with the cassette lock-ring 125 first. At this time, the cap bumps 130t1 and 130t2d located in the cap opening 130d of the cassette cap 130 are aligned with the grooves 126h1 and 126h2 of the ring portion 126 of the cassette lock-ring 125, whereby the cap bumps 130t1 and 130t2 are allowed to be inserted in the grooves 126h1 and 126h2, and the ring portion 126 of the cassette lock-ring 125 is able to pass through the cap opening 130d (arrow AR1).

Along the peripheral direction of the cap opening 130d, the cap bump 130t1 is longer than the cap bump 130t2, and the groove 126h1 and the groove 126h2 have shapes corresponding to the cap bump 130t1 and the cap bump 130t2. Therefore, the cap bump 130t1 is longer than the groove 126h2, so that the cap bump 130t1 cannot be inserted in the groove 126h2. In other words, it is impossible to insert the rotation lock unit 120 into the cap columnar space 130c of the cassette cap 130 while aligning the cap bumps 130t1 and 130t2 respectively with the grooves 126h2 and 126h1. This prevents the rotation lock unit 120 from being placed in the cap columnar space 130c of the cassette cap 130 in the wrong direction.

Once the spring 124 reaches the cap opening 130d, the rotation lock unit 120 is rotated, and the cap bumps 130t1 and 130t2 are aligned with the second side surface subportion 121e of the ring portion 121 of the cartridge stopper 123 and the end 121g2 of the groove 121g. For example, in the example shown in FIG. 7, it is rotated by about 90° in the right direction (arrow AR2). As a result of this, the cap bumps 130t1 and 130t2 respectively pass along the second side surface subportion 121e and the end 121g2 of the groove 121g, whereby the rotation lock unit 120 moves into the cap columnar space 130c (arrow AR3). Thereafter, the rotation lock unit 120 is rotated in the opposite direction so that the second side surface subportion 121e becomes opposed to the button space 130f of the cassette cap 130. For example, it is rotated by about 90° in the left direction (arrow AR4). As a result of this, the cap bumps 130t1 and 130t2 are placed in the grooves 121g and 121h of the ring portion 121 of the cartridge stopper 123. In this state, the urging force of the spring 124 urges the cartridge stopper 123 and the cassette lock-ring 125 respectively toward the first end 130a and the second end 130b. Because the cap bumps 130t1 and 130t2 abuts with the side surfaces of the grooves 121g and 121h of the ring portion 121, the cartridge stopper 123 is prevented from jumping out of the cap columnar space 130c owing to the urging force of the spring 124.

<Operation 1 of the Cassette 100>

Figure 8A:
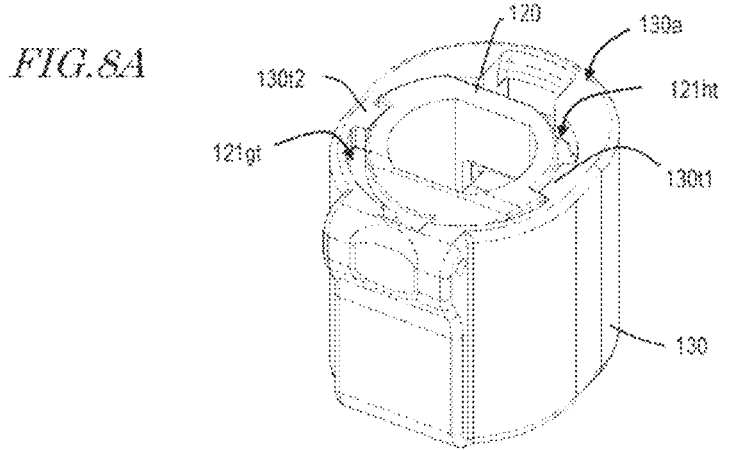
FIG. 8A is a perspective view showing a state of the rotation lock unit in the cassette cap in the case where the cassette cap is open or in the case where the cassette cap is closed without the drug cartridge being inserted in a cartridge holder.
Figure 8B:
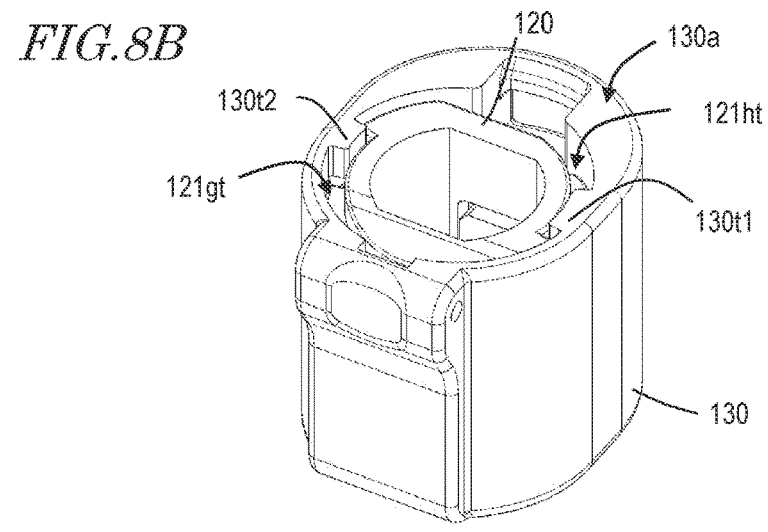
FIG. 8B is a perspective view showing a state of the rotation lock unit in the cassette cap in the case where the cassette cap is closed while the drug cartridge is accommodated in the cartridge holder.

In a state where the drug cartridge 10 is not accommodated in the cassette 100, preferably the locking mechanism should be unable to lock the cassette cap 130. This can be implemented by ensuring that the rotation lock unit 120 is unpivotable in the state where the drug cartridge 10 is not accommodated in the cassette 100, for example. FIG. 8A is a perspective view showing a state of the rotation lock unit 120 in the cassette cap 130 in the case where the cassette cap 130 is open or in the case where the cassette cap 130 is closed without the drug cartridge 10 being inserted in the cartridge holder 110; FIG. 8B is a perspective view showing a state of the rotation lock unit 120 in the cassette cap 130 in the case where the cassette cap 130 is closed while the drug cartridge 10 is accommodated in the cartridge holder 110; and FIG. 8C is a perspective view showing the positions of the rotation lock unit 120 in the states shown in FIG. 8A and FIG. 8B in comparison.

Figure 8C:
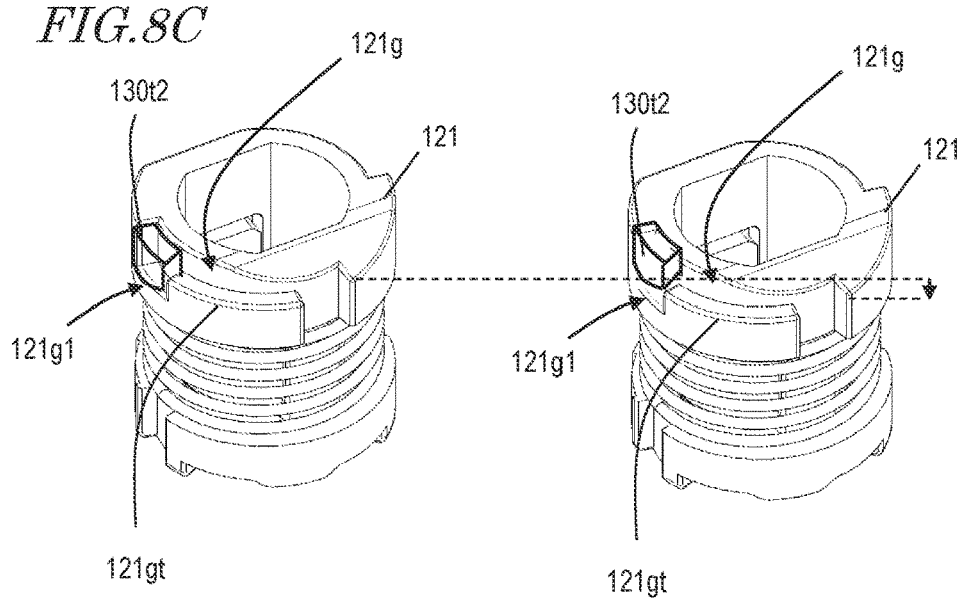
FIG. 8C is a perspective view showing the positions of the rotation lock unit in the states shown in FIG. 8A and FIG. 8B in comparison.

As shown in FIG. 8A and FIG. 8C, in the case where the cassette cap 130 is open or in the case where the cassette cap 130 is closed without the drug cartridge 10 being inserted in the cartridge holder 110, as described above, the urging force of the spring 124 urges the cartridge stopper 123 toward the first end 130a. Therefore, at the end 121g1 of the groove 121g, the cap bump 130t2 abuts with the side surface of the groove 121g of the ring portion 121 at the second end 121b side. Similarly, at the end 121h1 of the groove 121h (FIG. 6A), the cap bump 130t1 abuts with the side surface of the groove 121h of the ring portion 121 at the second end 121b side. This prevents the cartridge stopper 123 from jumping out from the cap columnar space 130c owing to the urging force of the spring 124.

At this time, if one tries to rotate the rotation lock unit 120, as shown on the left side of FIG. 8C, the cap bump 130t2 will abut with the stopper bump 121gt. Similarly, the cap bump 130t1 will abut with the stopper bump 121ht (FIG. 8A, FIG. 8B). In this state, the rotation lock unit 120 is unpivotable.

On the other hand, as will be described below, if the cassette cap 130 is closed with the drug cartridge 10 being inserted in the cartridge holder 110, the rear end of the drug cartridge 10 enters into the cassette cap 130, thus pushing in the cartridge stopper 123 against the urging force of the spring 124. Consequently, as shown in FIG. 8B, the cartridge stopper 123 moves backward.

At this time, since the sloped surface 121i of the cartridge stopper 123 of the cassette cap 130 is tilted toward the outer periphery, the rear end of the drug cartridge 10 abuts with the sloped surface 121i of the cartridge stopper 123 while the cassette cap 130 is situated closer to the holder opening 110d than if the first end 121a of the ring portion 121 were composed only of the abutting surface 121f. Therefore, the direction of the force that the sloped surface 121i of the cassette cap 130 receives from the rear end of the drug cartridge 10 makes a reduced angle with the axis 121ca, i.e., the moving direction of the cartridge stopper 123, thereby allowing the cartridge stopper 123 to smoothly move backward.

As a result, as shown on the right side of FIG. 8C, the cartridge stopper 123 moves backward relative to the cap bump 130t2, and the cap bump 130t2 becomes spaced apart from the stopper bump 121gt. Similarly, the cap bump 130t1 becomes spaced apart from the stopper bump 121ht. This enables the rotation lock unit 120 to pivot. With such structure of the rotation lock unit 120, when the drug cartridge 10 is not loaded in the cassette 100, the rotation lock unit 120 cannot pivot and thus the cassette cap 130 cannot lock.

<Operation 2 of the Cassette 100>

Figure 9A:
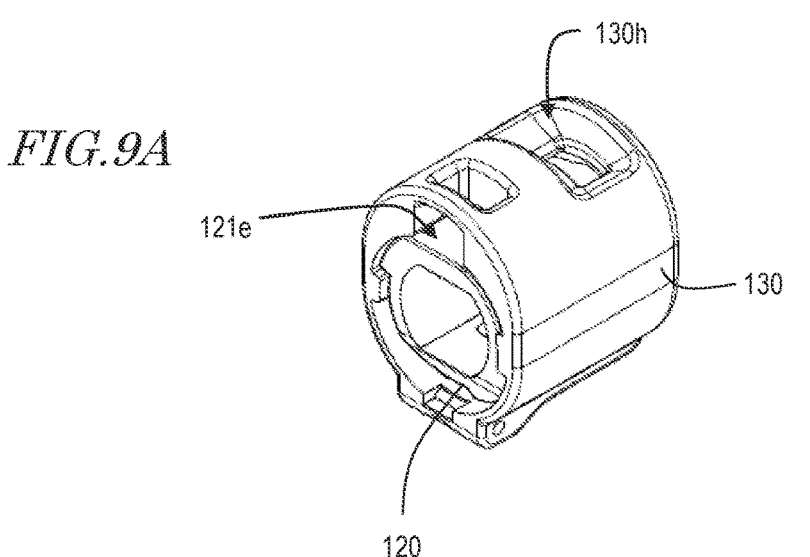
FIG. 9A is a perspective view of the cassette cap accommodating the rotation lock unit in an unlocked state.
Figures 9B, 10A, 10B, 10C:
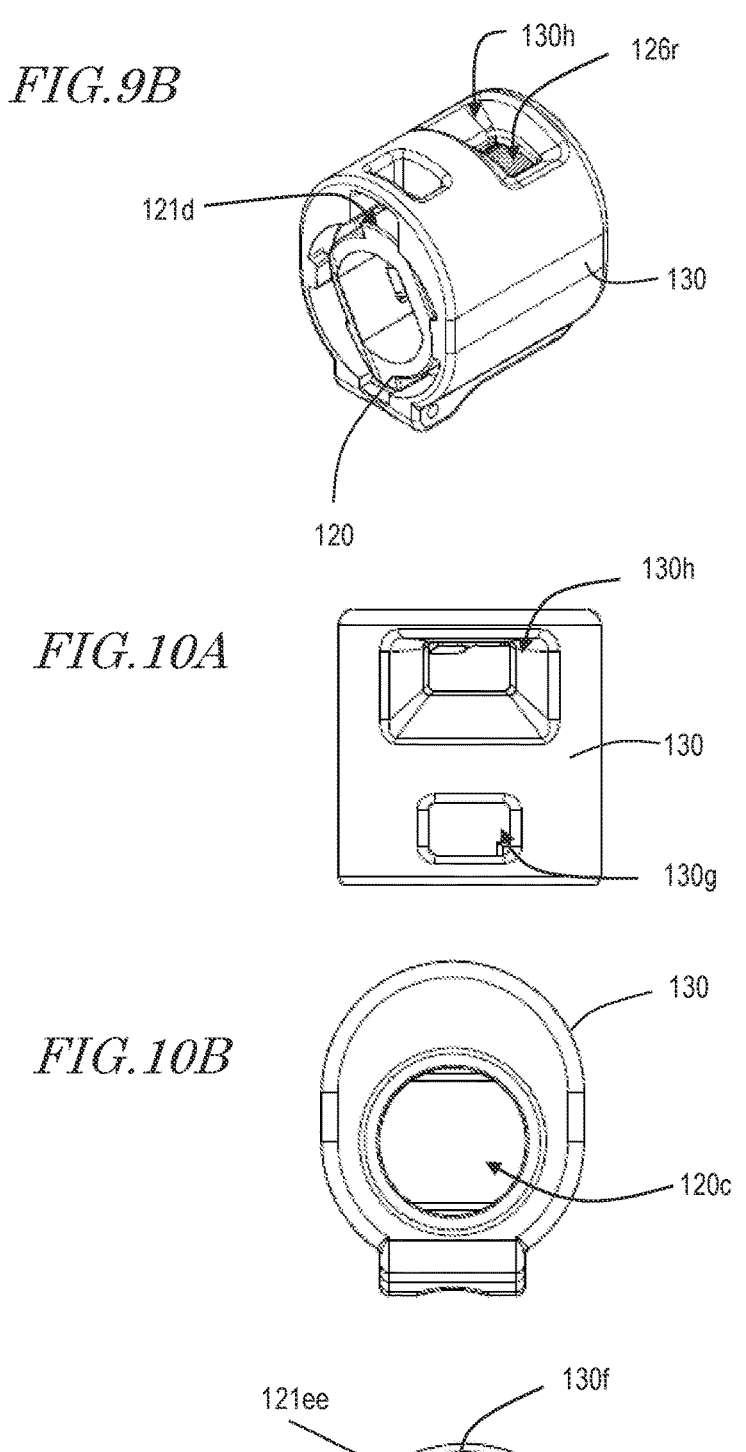
FIG. 9B is a perspective view of the cassette cap accommodating the rotation lock unit in a locked state.
FIG. 10A is a top view of the cassette cap in the unlocked state.
FIG. 10B is a side view of the cassette cap in the unlocked state as viewed from the first end.
FIG. 10C is side view of the cassette cap in the unlocked state as viewed from the second end.
Figure 11A:
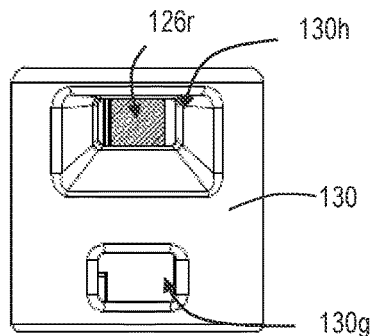
FIG. 11A is a top view of the cassette cap in the locked state.
Figure 11B:
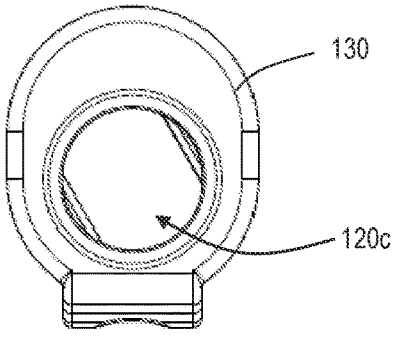
FIG. 11B is a side view of the cassette cap in the locked state as viewed from the first end.
Figure 11C:
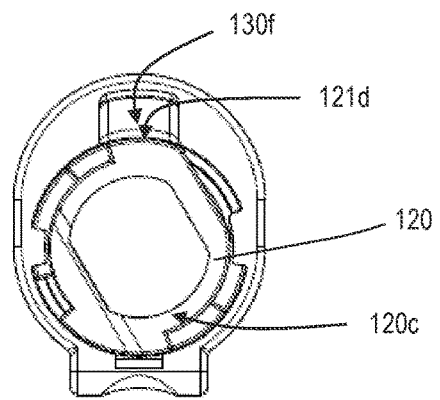
FIG. 11C is a side view of the cassette cap in the locked state as viewed from the second end.

Next, a locking operation of the cassette cap 130 in the cassette 100 will be described. FIG. 9A and FIG. 9B are perspective views of the cassette cap 130 accommodating the rotation lock unit 120 in an unlocked state and a locked state, respectively. FIG. 10A, FIG. 10B, and FIG. 10C are a top view, and side views as viewed from first end 130a and the second end 130b, of the cassette cap 130 in the unlocked state. FIG. 11A, FIG. 11B, and FIG. 11C are a top view, and side views as viewed from first end 130a and the second end 130b, of the cassette cap 130 in the locked state.

As shown in FIG. 5B and FIG. 5C, when the drug cartridge 10 is inserted in the holder columnar space 110c of the cartridge holder 110, the second end 11b of the cylinder 11 of the drug cartridge 10 protrudes from the holder opening 110d. If the cassette cap 130 is closed in this state, the rear end of the cylinder 11 of the drug cartridge 10 enters into the cassette cap 130, thus pushing in the cartridge stopper 123 against the urging force of the spring 124. Consequently, as shown in FIG. 9A, the cartridge stopper 123 moves backward.

The engaging portion 111g of the cassette button 111 is inserted into the button space 130f, which is adjacent to the cap columnar space 130c of the cassette cap 130, and the engaging portion 111g of the cassette button 111 engages with the engaging portion 130g of the cassette cap 130. Specifically, the hook shape of the engaging portion 111g engages with the opening of the engaging portion 130g. As a result, the cassette cap 130 keeps the holder opening 110d of the cartridge holder 110 closed.

In this state, the rotation lock unit 120 is placed in the unlock position. As shown in FIG. 10A, a region of the rotation lock unit other than the colored region 126r is located in the alarming aperture 130h. This allows the operator to recognize that the cassette cap 130 is not locked. Moreover, as shown in FIG. 10C, the second side surface subportion 121e of the cartridge stopper 123 is opposed to the button space 130f of the cassette cap 130. Since the shortest distance between the second side surface subportion 121e and the axis is shorter than the shortest distance between the first side surface subportion 121d and the axis, a space 121ee is created between the second side surface subportion 121e and the button space 130f. As shown in FIG. 10B and FIG. 10C, the unit throughhole 120c of the rotation lock unit 120 is oriented in a direction such that two flat planes exist along the horizontal direction, for example.

In this state, if the cassette button 111 is pressed, the engaging portion 111g of the cassette button 111 enters into the space 121ee, and further lowers until abutting with the second side surface subportion 121e, thereby releasing the engagement between the engaging portion 111g of the cassette button 111 and the engaging portion 130g of the cassette cap 130. At this time, since the cylinder 11 of the drug cartridge 10 abuts with the cartridge stopper 123, the cassette cap 130 is urged by the urging force of the spring 124 in the direction of opening the cassette cap 130, and the cassette cap 130 pivots around the shaft 131 as an axis so that the cassette cap 130 opens.

While the drug cartridge 10 is inserted in the cartridge holder 110 and the cassette cap 130 is closed, as described above, the cartridge stopper 123 is pushed by the drug cartridge 10 to move backward, so that the rotation lock unit 120 is capable of pivoting.

The drug injection device 200 includes the piston 210, which includes a leading end portion having a cross-sectional shape that corresponds to the cross-sectional shape of the unit throughhole 120c, and when the cassette 100 in the aforementioned state is loaded to the drug injection device 200, the piston 210 moves forward in order to release the drug in the drug cartridge 10. At this time, the piston 210 is inserted in the unit throughhole 120c of the rotation lock unit 120 as it moves forward while rotating, such that the leading end portion of the piston 210 moves forward while rotating in the unit throughhole 120c. Since the unit throughhole 120c and the leading end portion of the piston 210 have corresponding cross-sectional shapes, rotation of the piston 210 causes rotation of the rotation lock unit 120. As shown in FIG. 11B and FIG. 11C, for example, the piston 210 rotates by about 60° as viewed from the leading end, while moving forward in the unit throughhole 120c. As a result, the rotation lock unit 120 rotates clockwise by 60°, whereby the rotation lock unit 120 is placed in the lock position.

The lock position and the unlock position of the rotation lock unit 120 make an angle α around the axis of the cap columnar space, in a plane perpendicular to the axis of the cap columnar space. For example, a is 60° as described above. The angle α may be set to any arbitrary value. For example, α is not less than 30° and not more than 120°.

The unit throughhole 120c of the rotation lock unit 120 preferably has a cross section with a rotationally symmetrical shape other than a (360/α)-fold symmetric diagram, or have a cross section with a non-rotationally symmetrical shape.

With rotation of the rotation lock unit 120, as shown in FIG. 11C, the first side surface subportion 121d of the cartridge stopper 123 is now opposed to the button space 130f of the cassette cap 130. In this state, no extra space exists between the button space 130f and the first side surface subportion 121d; therefore, as shown in FIG. 5C, even if the cassette button 111 is pressed, abutment occurs between the engaging portion 111g and the first side surface subportion 121d so as not to allow the cassette button 111 to lower, i.e., the cassette button 111 cannot be pressed. Therefore, the engaging portion 111g of the cassette button 111 and the engaging portion 130g of the cassette cap 130 cannot be disengaged. In other words, the operator cannot open the cassette cap 130 by pressing the cassette button 111. Thus, even if the operator inadvertently presses the cassette button 111, the operator cannot open the cassette cap 130, whereby the drug cartridge 10 is prevented from being removed.

As shown in FIG. 4B and FIG. 4C, when the rotation lock unit 120 is in the unlock position, the surface 126f of the cassette lock-ring 125 is urged toward the inner surface 130m of the second end 130b of the cassette cap 130, and the first ring engaging portion 126g1 of the surface 126f engages with the cap engaging portion 130k of the inner surface 130m. Therefore, even if the cassette 100 is subjected to external vibrations or the like in this state, the rotation lock unit 120 is kept from rotating. Similarly, when the rotation lock unit 120 is in the lock position, the surface 126f of the cassette lock-ring 125 is urged toward the inner surface 130m of the second end 130b of the cassette cap 130, and the second ring engaging portion 126g2 of the surface 126f engages with the cap engaging portion 130k of the cassette cap 130 on the inner surface 130m. Therefore, even if the cassette 100 is subjected to external vibrations or the like in this state, the rotation lock unit 120 is kept from rotating.

Moreover, as can be seen from a comparison between FIGS. 10B and 10C and FIGS. 11B and 11C, projected images (shape and the orientation of the shape) of the unit throughhole 120c of the rotation lock unit 120 as projected on a plane perpendicular to its axis, of the case where the rotation lock unit 120 is in the lock position and of the case where the rotation lock unit 120 is in the unlock position, do not completely overlap but differ. This is because the unit throughhole 120c has a cross section with a rotationally symmetrical shape other than $(360/\alpha)$-fold symmetric.

In accordance with the cassette 100 and the drug injection device 200 according to the present embodiment, because the drug cartridge 10 contains an amount of drug that would correspond to a plurality of shots, it is possible for an unfinished cassette 100 (i.e., with some drug left therein) to be removed from the drug injection device 200. At this time, as will be described below, the drug injection device does not retract the piston 210, so that injection can be performed without taking time in the next instance the unfinished cassette is loaded to the drug injection device. Moreover, at this time, any cassette 100 that fails to have a drug cartridge accommodated therein or has an unused drug cartridge 10 accommodate therein cannot be properly loaded to the drug injection device 200. The reason is that, in any such cassette 100, the rotation lock unit 120 is in the unlock position and the orientation of the cross-sectional shape of the unit throughhole 120c differs from that in the lock position, so that the piston 210 cannot be inserted in the unit throughhole 120c of the cassette cap 130.

Thus, with the cassette 100 according to the present embodiment, provision of the rotation lock unit 120 enables locking of the cassette cap 130 of the cassette 100 having the drug cartridge 10 loaded thereto. This makes it less likely for the operator to inadvertently remove the drug cartridge 10 by pressing the cassette button 111. Moreover, when the cassette cap 130 is locked, the alarming section can inform the operator of the locked state, thus allowing the operator to recognize that in the current state it is inappropriate to remove the drug cartridge 10, for proper understanding of the device manipulations.

[Structure of the Drug Injection Device 200]

Figure 12A:
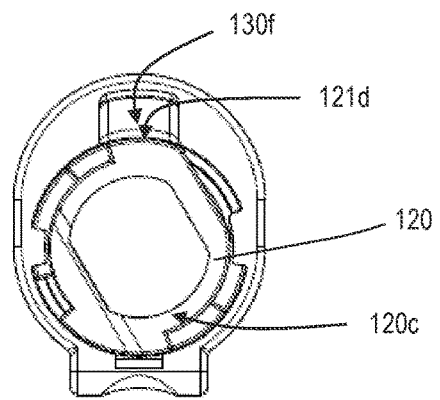
FIG. 12A is a perspective view of the drug injection device with the case removed, in a state where the cassette is not loaded.
Figures 12B, 13:
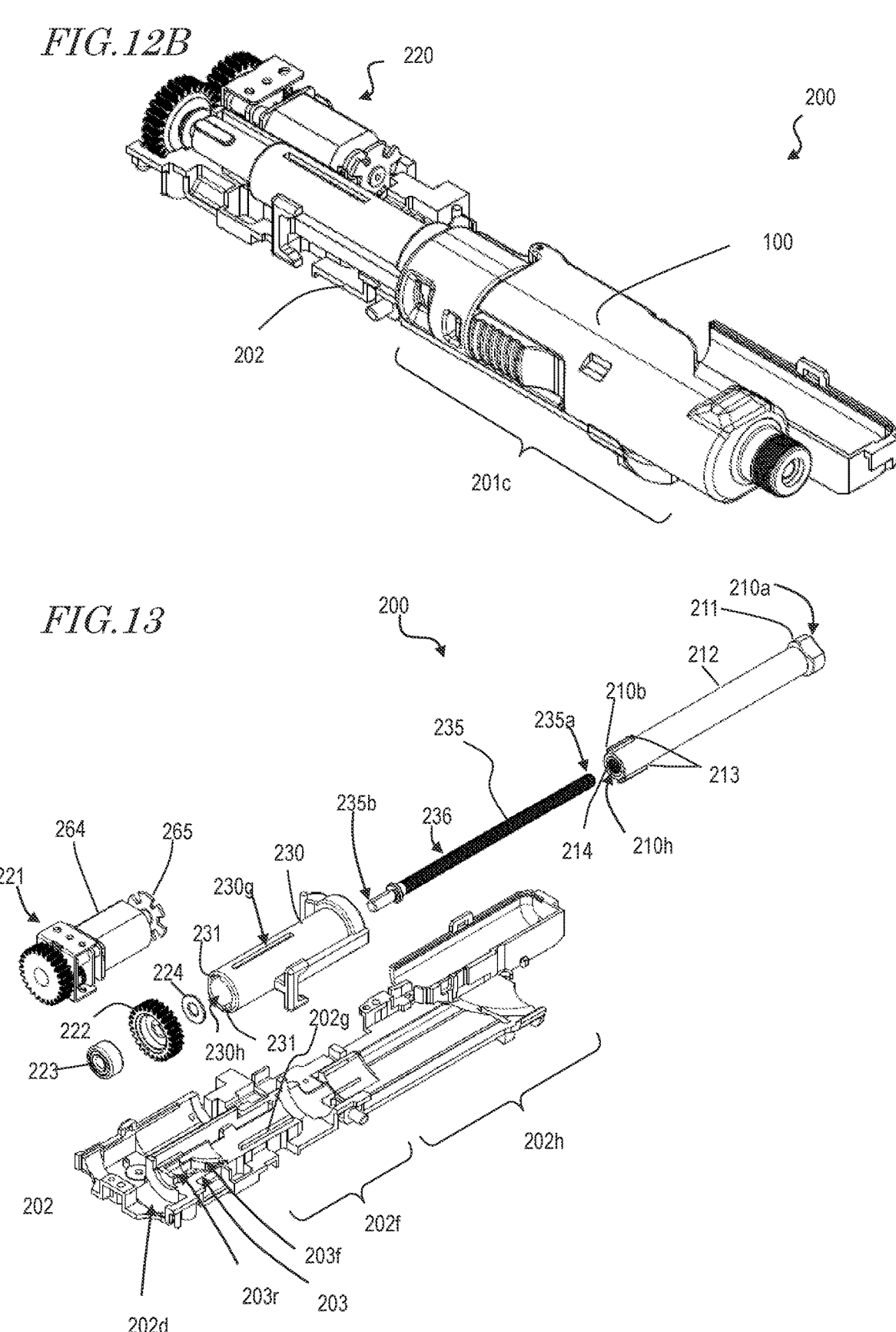
FIG. 12B is a perspective view of the drug injection device with the case removed, in a state where the cassette has been loaded.
FIG. 13 is an exploded perspective view of the drug injection device 200 with the case removed.

FIG. 12A and FIG. 12B are perspective views of the drug injection device 200 with the outer housing 201 removed. FIG. 12A shows a state where the cassette 100 is not loaded, whereas FIG. 12B shows a state where the cassette 100 has been loaded. FIG. 13 is an exploded perspective view of the drug injection device 200 with the outer housing 201 removed. FIGS. 14A to 14D and FIGS. 15A to 15E are perspective views illustrating forward movement and rotation of the piston 210.

In addition to the aforementioned outer housing 201 and control device 280, the drug injection device 200 includes the piston 210 and a piston driving mechanism 220. In the present embodiment, the drug injection device 200 further includes an inner housing 202 that supports the piston driving mechanism 220. As a whole, the outer housing 201 and the inner housing 202 constitute a housing for drug injection device 200.

In the drug injection device 200, in a state where the cassette 100 is accommodated in the cassette space 201c, the piston 210 is able to move forward and backward along the axial direction of the drug cartridge 10 loaded in the cassette 100, and to axially rotate. As the piston 210 moves forward, abuts with the gasket 13 of the drug cartridge 10, and pushes in the gasket 13, the drug 14 can be discharged from the injection needle 21. When the piston 210 axially rotates while moving forward as described above, the rotation lock unit 120 of the cassette cap 130 is pivoted between the lock position and the unlock position, whereby the cassette cap 130 is locked or unlocked.

The piston driving mechanism 220 drives the piston 210 in a direction of moving forward or moving backward, and also axially rotates the piston 210.

[Piston 210]

The piston 210 includes the leading end portion 211 and a main body 212 that is connected to the leading end portion. The leading end portion 211 is located near the first end 210a. In the present embodiment, the leading end portion 211 has an I-cut shape resulting from cutting a geometric cylinder at two parallel planes extending along the axis. FIG. 16A is a front view of the piston 210 as viewed from the first end 210a, in which: the left side shows a state where the piston 210 is in the initial position and is insertable in the rotation lock unit 120 (of the cassette 100 loaded in the drug injection device 200) being in the unlock position; and the right side shows a state where the piston 210 is insertable in the rotation lock unit 120 being in the lock position.

As shown in FIG. 16A, the outer edge of a projected shape of the main body 212 on a plane perpendicular to the axis is located inward of the outer edge of a projected shape of the leading end portion 211. Therefore, if the leading end portion 211 is insertable in the unit throughhole 120c of the cassette 100 loaded in the drug injection device 200 in either the unlock position or the lock position, the main body can also pass through the unit throughhole 120c, and therefore, as the piston 210 moves forward, it abuts with the gasket 13 of the drug cartridge 10 being accommodated in the cassette 100, thus moving forward the gasket 13.

In the case where a cross sectional shape of the leading end portion 211 of the piston 210 that permits insertion into the rotation lock unit 120 in the unlock position as shown on the left side of FIG. 16A differs in orientation from a cross-sectional shape of the leading end portion 211 of the piston 210 that permits insertion into the rotation lock unit 120 in the lock position as shown on the right side, it is possible to selectively load either a cassette 100 whose rotation lock unit 120 is in the lock position or a cassette 100 whose rotation lock unit 120 is in the unlock position. In other words, as described above, when an unfinished cassette is removed from the drug injection device, any cassette 100 that fails to have a drug cartridge accommodated therein or has an unused drug cartridge 10 accommodate therein can no longer be properly loaded to the drug injection device 200.

As can be seen from a comparison between FIGS. 10B and 10C and FIGS. 11B and 11C, projected images (shape and the orientation of the shape) of the unit throughhole 120c of the rotation lock unit 120 as projected on a plane perpendicular to its axis, of the case where the rotation lock unit 120 is in the lock position and of the case where the rotation lock unit 120 is in the unlock position, do not completely overlap but differ (do not match). This is because the unit throughhole 120c has a cross section with a rotationally symmetrical shape other than $(360/\alpha)$-fold symmetric, or a non-rotationally symmetrical shape.

For this purpose, similarly to the cross section of the unit throughhole 120c, given that the angle between lock position and the unlock position of the rotation lock unit 120 of the cassette 100 is a, it is preferable that the leading end portion of the piston 210 has a cross section with a rotationally symmetrical shape other than $(360/\alpha)$-fold symmetric, or that the leading end portion of the piston 210 has a cross-sectional shape which is not rotationally symmetric. For example, when the angle $\alpha$ is 60°, the leading end portion 211 of the piston 210 may have a cross-sectional shape that is any rotationally symmetrical shape other than $6(360/60)$-fold symmetric.

For example, as shown on the left side of FIG. 16B, when the leading end portion 211 has a square cross-sectional shape, the leading end portion 211 has a cross section with a 4-fold symmetrical shape. Therefore, as shown on the right side of FIG. 16B, a cross section of the leading end portion 211 of the case where the piston 210 is axially rotated by 60° has a different orientation from that of the shape before rotation. As shown in FIG. 16C, when the leading end portion 211 has a D-cut shape, the leading end portion 211 has a cross-sectional shape which is not rotationally symmetric. Therefore, as shown on the right side of FIG. 16B, a cross section of the leading end portion 211 of the case where the piston 210 is axially rotated by 60° has a different orientation from that of the shape before rotation; even when the piston 210 is rotated by any other rotation angle, the cross section will have a different orientation from that of the cross section before rotation.

On the other hand, as shown on the left side of FIG. 16D, when the leading end portion 211 has a cross-sectional shape that is a regular hexagon, the cross section of the leading end portion 211 has a 6-fold symmetrical shape. Therefore, as shown on the right side of FIG. 16D, the cross section of the leading end portion 211 in the case where the piston 210 is axially rotated by 60° has the same orientation as that of the shape before rotation. Therefore, in this case, both of a cassette 100 whose rotation lock unit 120 is in the lock position and a cassette 100 whose rotation lock unit 120 is in the unlock position are loadable to the drug injection device. This does not permit distinction between the lock position and the unlock position of the rotation lock unit 120.

The piston 210 includes driving bumps 213 located on the side surface of the main body 212. The driving bumps 213 engage with a first guide 203 and second guides 231 provided in the piston driving mechanism 220 as will be described below, thus causing the piston 210 to axially rotate or restrict rotation in accordance with the shapes of the first guide 203 and the second guides 231. The driving bumps 213 and the first guide 203 and second guides 231 may be such that, for example, one of them is located on the side surface of the piston 210 while the other is located on the inner housing 202. In the present embodiment, the driving bumps 213 are ribs provided on the side surface of the piston 210, the ribs being ridge-shaped bumps extending in parallel to the axis of the piston 210. More specifically, the piston 210 includes two driving bumps 213 that are provided near the second end 210b of the side surface of the main body.

The main body 212 of the piston 210 is provided with an internal thread 214 that is located on the inner side of a hole 210h extending along the axis of the piston 210.

[Piston Driving Mechanism 220]

The piston driving mechanism 220 includes the injection motor 264, a gearbox 221, a drive gear 222, a drive rod 235, and a piston guide 230. The injection motor 264, the gearbox 221, the drive gear 222, and the piston guide 230 are supported on the inner housing 202. A lower half of the inner housing 202 is shown in FIG. 13 and the like, while an upper half not shown also has a similar shape.

The injection motor 264 rotates forward or backward under the control of the control device 280. As used herein, rotating forward means rotating in the direction of causing the piston 210 to move forward, whereas rotating backward means rotating in the direction of causing the piston 210 to move backward.

On the shaft of the injection motor 264, the encoder 265 is mounted as an amount-of-rotation detector, the encoder 265 detecting the amount of rotation (number of revolutions) of the injection motor 264.

The gearbox 221 includes at least one gear mounted on the shaft of the injection motor 264. The gearbox 221 may include two or more gears in order to reduce the rotational speed of the injection motor 264.

The drive gear 222 meshes with the gear(s) in the gearbox 221, and is rotatably supported on the inner housing 202 via a bearing 223. A hole is made in the shaft of the drive gear 222, to which one end of the drive rod 235 is inserted and fitted.

The drive rod 235 has the shape of a rod, with an external thread 236 formed on its side surface. The external thread 236 has its thread height, shape, thread pitch, etc., configured so as to mesh with the internal thread 214 provided on the piston 210.

The piston guide 230 has a hole 230h into which the piston 210 is inserted. The second guides 231 are provided on the inner side surface of the hole 230h. The second guides 231 engage with the driving bumps 213 of the piston 210, thereby guiding the piston 210 so as to move forward or move backward without axially rotating.

The length of the piston guide 230 along the axial direction is shorter than the length of the main body 212 of the piston 210 so that, in an initial state where the piston 210 has moved farthest backward, the driving bumps 213 of the piston 210 have moved farther backward from the rear end of the piston guide 230. Therefore, in the initial state, the aforementioned second guides 231 and driving bumps 213 are not engaged, and the piston 210 is able to axially rotate relative to the piston guide 230.

In the present embodiment, the second guides 231 are linear grooves extending in parallel to the axis of the hole 230h, and the ribs which are the driving bumps 213 provided on the side surface of the piston 210 are inserted therein. The piston guide 230 includes two second guides 231 correspondingly to the two driving bumps 213 on the piston 210. The piston guide 230 has a groove 230g in its side surface.

The inner housing 202 includes a gear region 202d, the first guide 203, a piston guide region 202f, a cassette region 202h, and a ridge-shaped bump 202g. The drive gear 222 is placed in the gear region 202d. The cassette region 202h is a region defining the cassette space 201c.

The piston guide region 202f includes the bump 202g, and the piston guide 230 is placed in the piston guide region 202f in such a manner that the bump 202g is inserted in the groove 230g of the piston guide 230. Because the bump 202g is inserted in the groove 230g, the piston guide 230 is kept from being forced to rotate along with the piston 210 when it is driven.

Moreover, as will be described below, an urging force from a spring may be utilized for enhanced manipulation ease when loading the cassette 100 to the drug injection device 200 and in ejecting the cassette 100 from the drug injection device 200. In this case, it is preferable that the length of the bump 202g along the axial direction is smaller than that of the groove 230g of the piston guide 230 so that the piston guide 230 is capable of moving along the axial direction within the piston guide region 202f.

The first guide 203 engages or abuts with the driving bumps 213 of the piston 210, and guides the piston 210 so as to move forward or backward while allowing the piston 210 to rotate. In the present embodiment, the first guide 203 is a recess having a helical surface 203f and a helical surface 203r which are respectively located near the leading end and the rear end, such that the ribs which are the driving bumps 213 can be inserted therein. The angle by which the helical surface 203*f* and the helical surface 203*r* are twisted is essentially equal to the angle α, which is the rotation angle between the lock position and the unlock position. The positions of the end portions (front ends) of the helical surface 203*f* and the helical surface 203*r* at the leading end are essentially identical to those of the end portions of the second guides 231 (of the piston guide 230 placed in the piston guide region 202*f*) at the rear end. Moreover, because of the piston guide 230 being placed in the piston guide region 202*f*, the second guides 231 are located between the first guide 203 and the cassette space 201*c*.

[Driving of the Piston 210 by the Piston Driving Mechanism 220]

With reference to FIGS. 14A to 14D and FIGS. 15A to 15E, driving of the piston 210 by the piston driving mechanism 220 will be described.

Figure 14A:
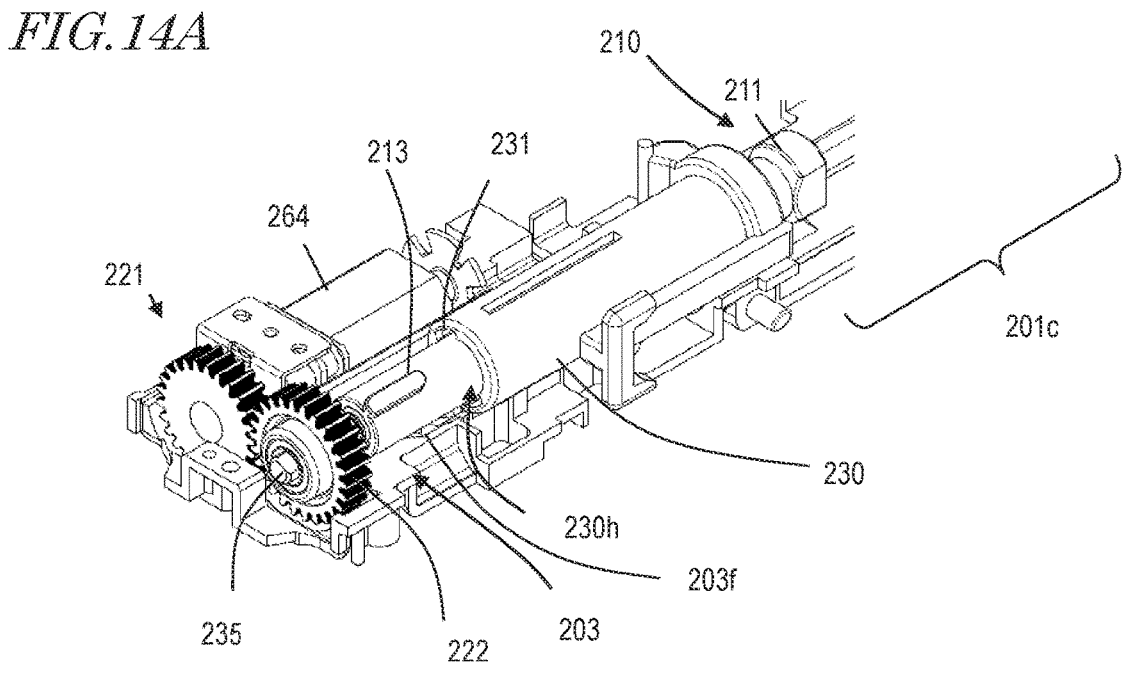
FIG. 14A is a perspective view illustrating forward movement and rotation of the piston.
Figure 14B:
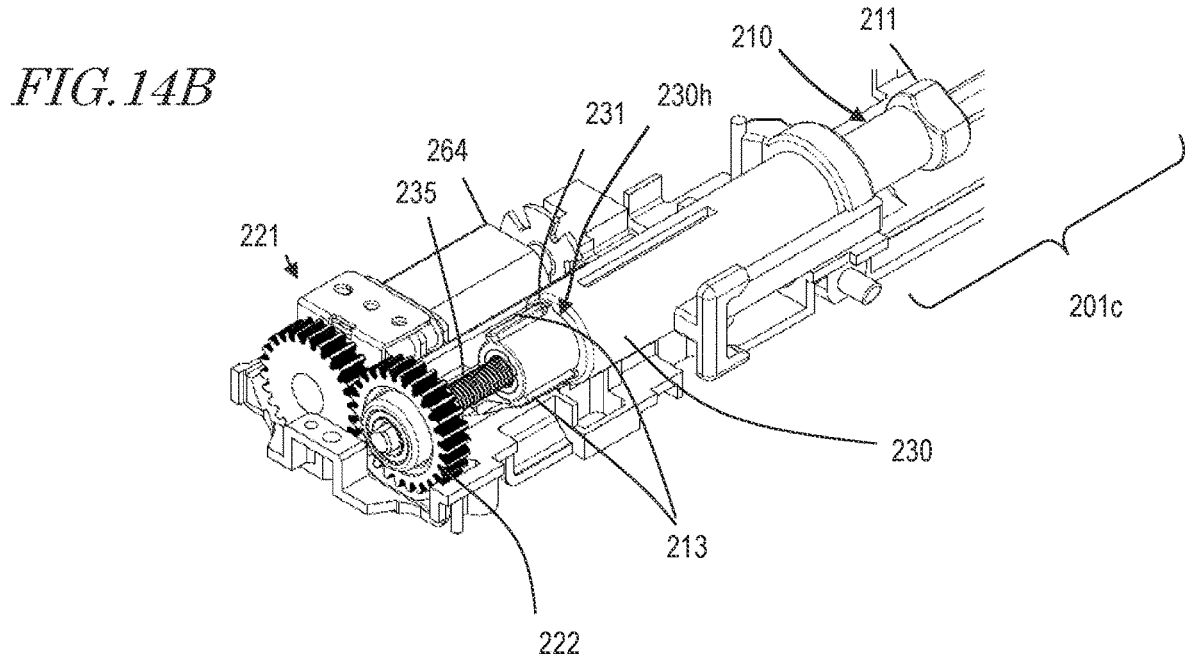
FIG. 14B is a perspective view illustrating forward movement and rotation of the piston.
Figures 14C, 14D, 15A:
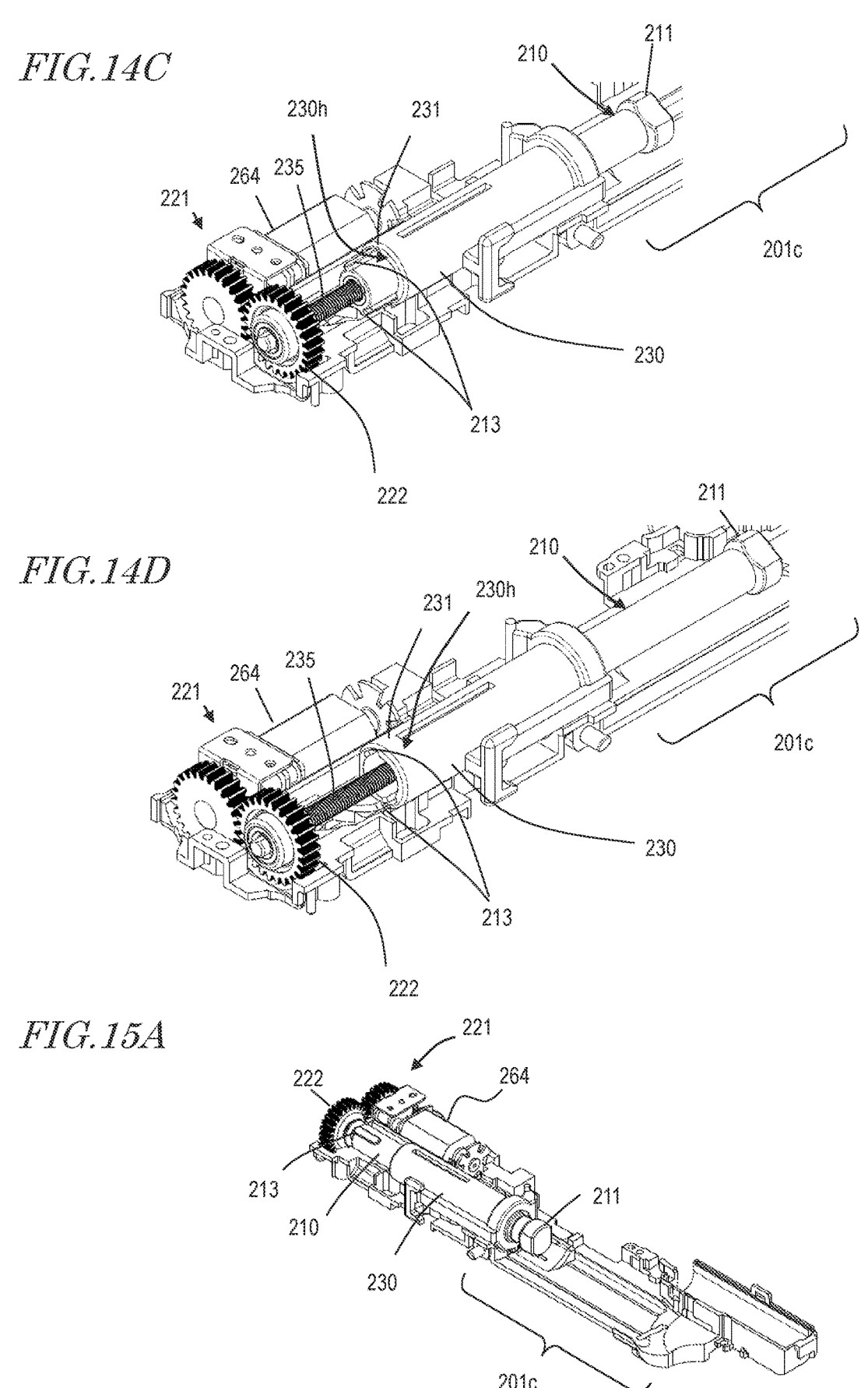
FIG. 14C is a perspective view illustrating forward movement and rotation of the piston.
FIG. 14D is a perspective view illustrating forward movement and rotation of the piston.
FIG. 15A is a perspective view illustrating forward movement and rotation of the piston.

As shown in FIG. 14A and FIG. 15A, in the initial state, the piston 210 is inserted in the hole 230*h* of the piston guide 230, with the drive rod 235 being inserted in the hole 210*h* of the piston 210. The leading end portion 211 of the piston 210 is located in the cassette space 201*c*. Moreover, the driving bumps 213 of the piston 210 are located in the first guide 203, such that the front ends of the ribs which are the driving bumps 213 abut with the rear end of the helical surface 203*f*.

When the injection motor 264 rotates forward with an instruction from the control device 280, the drive gear 222 rotates via the gearbox 221, and the drive rod 235 rotates. When the drive rod 235 rotates, the internal thread 214 of the piston 210 meshing with the external thread 236 of the drive rod 235 receives an axial rotational force. As described above, in the initial state, the driving bumps 213 are located outside the piston guide 230, so that the piston 210 is able to axially rotate. Therefore, the piston 210 is forced to rotate along with the drive rod 235. However, since the front ends of the ribs which are the driving bumps 213 abut with the helical surface 203*f* of the first guide 203, the piston 210 moves forward while axially rotating in accordance with the helix of the helical surface 203*f*. At this time, the rotation lock unit 120 of the cassette 100 begins rotation from the unlock position.

Figure 15B:
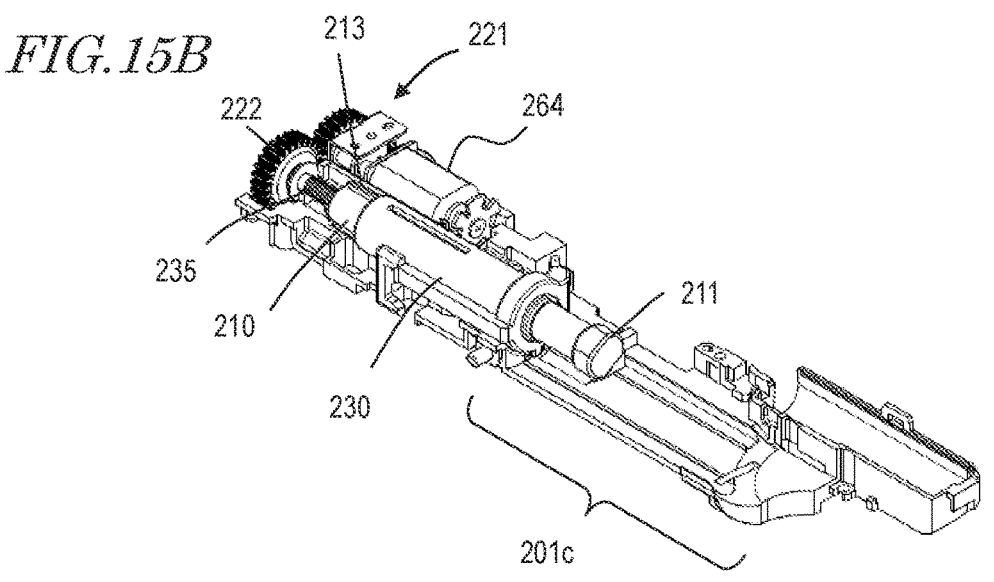
FIG. 15B is a perspective view illustrating forward movement and rotation of the piston.

FIG. 14B and FIG. 15B show a state where the front ends of the ribs which are the driving bumps 213 have reached the front end of the helical surface 203*f* of the first guide 203. From the initial state to this state, the piston 210 axially rotates by the angle α. Consequently, the rotation lock unit 120 of the cassette 100 rotates to the lock position.

Figure 15C:
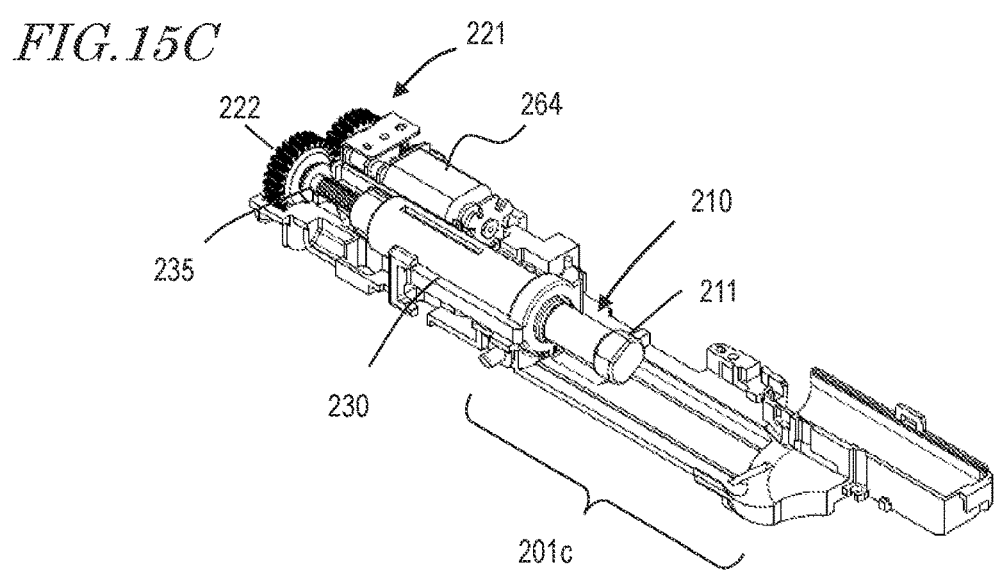
FIG. 15C is a perspective view illustrating forward movement and rotation of the piston.

Once the front ends of the driving bumps 213 have reached the front end of the helical surface 203*f*, the piston 210 moves farther forward, so that the driving bumps 213 are inserted in the grooves of the second guides 231, as shown in FIG. 14C and FIG. 15C. Since the second guides 231 are linear grooves, axial rotation of the piston 210 is thereafter restricted by the second guides 231, so that the piston 210 moves forward while not rotating with the rotation of the drive rod 235.

Figure 15D:
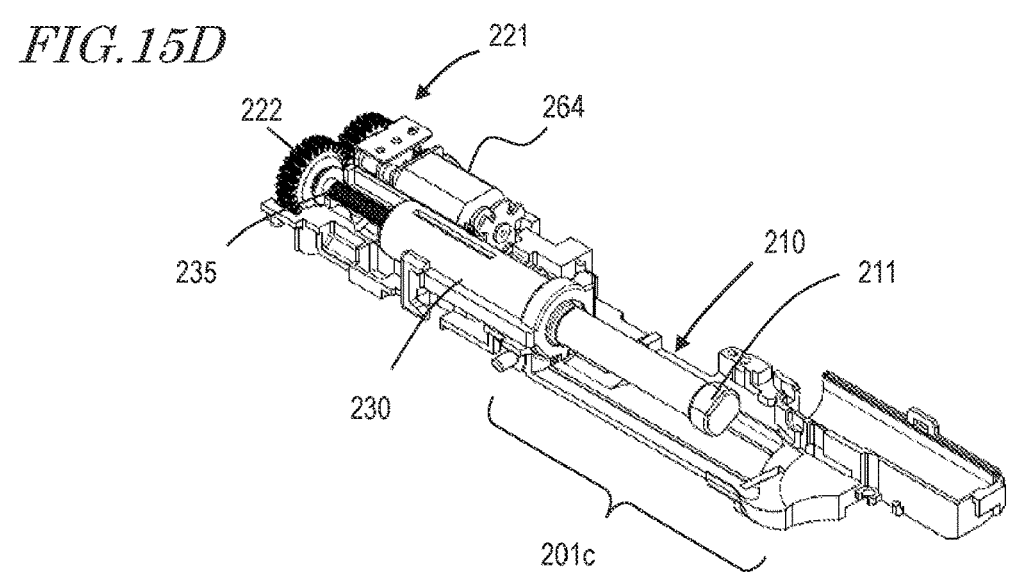
FIG. 15D is a perspective view illustrating forward movement and rotation of the piston.
Figures 15E, 16A, 16B, 16C, 16D:
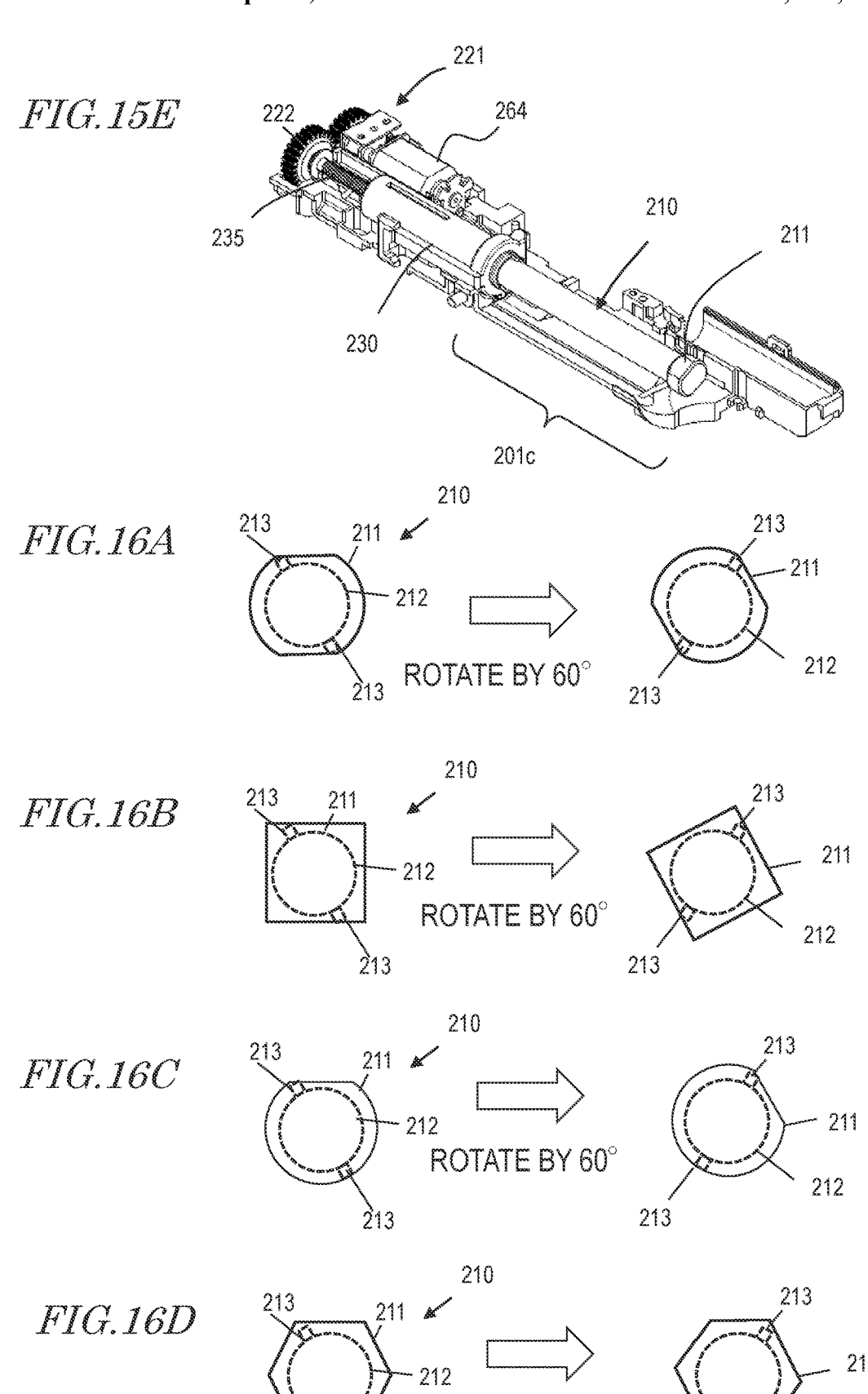
FIG. 15E is a perspective view illustrating forward movement and rotation of the piston.
FIG. 16A is a front view of the piston as viewed from the first end, in which: the left side shows a state where the piston is in the initial position and is insertable in the rotation lock unit (of the cassette loaded in the drug injection device) being in the unlock position; and the right side shows a state where the piston is insertable in the rotation lock unit being in the lock position.
FIG. 16B is a front view of another implementation of the piston as viewed from the first end, in which: the left side shows a state where the piston is in the initial position and is insertable in the rotation lock unit (of the cassette loaded in the drug injection device) being in the unlock position; and the right side shows a state where the piston is insertable in the rotation lock unit being in the lock position.
FIG. 16C is a front view of another implementation of the piston as viewed from the first end, in which: the left side shows a state where the piston is in the initial position and is insertable in the rotation lock unit (of the cassette loaded in the drug injection device) being in the unlock position; and the right side shows a state where the piston is insertable in the rotation lock unit being in the lock position.
FIG. 16D is a front view of an implementation of the piston according to a comparative example as viewed from the first end, in which: the left side shows a state where the piston is in the initial position and is insertable in the rotation lock unit (of the cassette loaded in the drug injection device)

FIG. 14D, FIG. 15D, and FIG. 15E show states where the piston 210 has moved farther forward. In these states, the piston 210 does not axially rotate. FIG. 15E shows a state where the piston 210 has moved farthest forward.

Through an opposite operation of the aforementioned operation, the piston 210 moves backward. Specifically, when the injection motor 264 rotates backward with an instruction from the control device 280, the rotation of the drive rod 235 causes the external thread 236 of the drive rod 235 and the internal thread 214 of the piston 210 to mesh with each other, thereby restricting axial rotation. As a result, from the state where the piston 210 has moved farthest forward as shown in FIG. 15E, the piston 210 moves backward without axially rotating.

As shown in FIG. 14B and FIG. 15B, when the piston 210 has moved backward until the entire ribs which are the driving bumps 213 have disengaged from the second guides 231 of the piston guide 230, the piston 210 becomes able to axially rotate. At this time, the rear ends of the ribs which are the driving bumps 213 abut with the helical surface 203*r* of the first guide 203, and therefore the piston 210 moves backward while axially rotating in accordance with the helix of the helical surface 203*r*. At this time, the rotation lock unit 120 of the cassette 100 begins rotation from the lock position. As shown in FIG. 14A and FIG. 15A, the piston 210 axially rotates by the angle α until the rear ends of the ribs which are the driving bumps 213 reach the rear end of the helical surface 203*r* of the first guide 203, whereby the piston 210 returns to the initial position. As a result, the rotation lock unit 120 of the cassette 100 rotates to the unlock position.

[Locking of the Cassette 100]

The drug injection device 200 may include a locking mechanism, so that the loaded cassette 100 cannot be easily removed through erroneous manipulations. FIG. 17A and FIG. 17B are perspective views describing a locking operation when inserting the cassette 100. FIG. 18A and FIG. 18B are perspective views describing a unlocking operation when ejecting the cassette 100.

The locking mechanism includes a pair of cassette retention arms 241, an arm spring 242, a piston guide spring 243, a slide base 215, and a clamp section 232 that is connected to the piston guide 230, for example.

Each of the cassette retention arms 241 includes a tab 241*g* located near the leading end, a first abutting portion 241*c* located at the rear end, a pivot 241*e* located between the tab 241*g* and the first abutting portion 241*c*, and a bump 241*f* being located between the pivot 241*e* and the first abutting portion 241*c* and including a second abutting portion 241*d*. The tabs 241*g* are capable of engaging with the lock recesses 110*g* in the cartridge holder 110 of the cassette 100. The pivot 241*e* is a pivoting axis of the cassette retention arm 241, e.g., a bump or an aperture. At the pivot 241*e*, the cassette retention arm 241 is supported by the inner housing 202 so as to capable of pivoting.

The arm spring 242 is disposed between the bumps 241*f* of the pair of cassette retention arms 241, and urges the two bumps 241*f* so as to become spaced apart. For example, the arm spring 242 may be a torsion spring.

The slide base 215 includes: a base portion 215*c*; a ring portion 215*d* being connected to the base portion 215*c* and having an aperture into which the piston guide 230 is inserted; and a pair of base abutting portions 215*e*, which may be opposed to the first abutting portions 241*c* of the pair of cassette retention arms 241. The ejection lever 209 is connected to the base portion 215*c* of the slide base 215, such that the slide base 215 is supported by the inner housing 202 so as to be capable of moving along the axial direction.

The piston guide spring 243, which is placed on the outer side surface of the piston guide 230, is located between a flange 230*c* that is located near the leading end of the piston guide 230 and the ring portion 215*d* of the slide base 215. The piston guide spring 243 is a compression coil spring, for example.

The clamp section 232 includes a pair of clamp abutting portions 232c, which may be opposed to the second abutting portions 241d of the pair of cassette retention arms 241.

When the cassette 100 is not inserted in the cassette space 201c of the drug injection device, as the piston guide spring 243 urges the flange 230c of the piston guide 230, the clamp section 232 of the piston guide 230 is also urged toward the cassette space 201c, whereby the clamp abutting portions 232c come to abut with the second abutting portions 241d so as to sandwich the second abutting portions 241d of the pair of cassette retention arms 241. As a result, in the pair of cassette retention arms 241, the portions that are on the rear end side of the pivots 241e are urged so as to come closer, whereas the portions on the leading end side of the pivots 241e become farther apart.

When the cassette 100 is inserted in the cassette space 201c in this state, the second end 130b of the cassette cap 130 abuts with the piston guide 230. If the operator further inserts the cassette 100 against the urging by the piston guide spring 243, the piston guide 230 moves backward, with which the clamp section 232 also moves backward. Consequently, as shown in FIG. 17B, the clamp abutting portions 232c of the clamp section 232 of the piston guide 230 become spaced apart from the second abutting portions 241d of the pair of cassette retention arms 241, and the urging by the arm spring 242 causes the portions of the cassette retention arms 241 that are on the rear end side of the pivots 241e to become farther apart. As a result, the portions of the cassette retention arms 241 on the leading end side of the pivots 241e come closer, so that the tabs 241g engage with the lock recesses 110g in the cartridge holder 110 of the cassette 100. Thus, loading of the cassette 100 is completed.

In this state, because the tabs 241g of the cassette retention arms 241 are engaged with the lock recesses 110g of the cassette 100, the cassette 100 cannot be pulled out by drawing it. Moreover, when the operator inserts the cassette 100, the resistive force due to urging by the piston guide spring 243 once increases, but thereafter the resistive force disappears upon locking, and this allows the operator to recognize that the cassette 100 has been loaded to the proper position based on a manipulation feel.

When ejecting the cassette 100, as the operator slides the ejection lever 209 toward the leading end with a finger, as shown in FIG. 18A, the base abutting portions 215e of the slide base 215 come to abut so as to sandwich the first abutting portions 241c of the pair of cassette retention arms 241. As a result, in the pair of cassette retention arms 241, the portions that are on the rear end side of the pivots 241e are urged so as to come closer, whereas the portions on the leading end side of the pivots 241e become farther apart. Consequently, as shown in FIG. 18B, the tabs 241g of the cassette retention arms 241 become spaced apart from the lock recesses 110g of the cassette 100.

Because the cassette 100 is retained against the urging by the piston guide spring 243, when locking by the cassette retention arms 241 is canceled, the urging force of the piston guide spring 243 causes the cassette 100 to move forward as a whole. In this state, the operator is able to pinch the cassette 100 with fingers and remove it. Moreover, the urging force of the piston guide spring 243 causes the ejection lever 209 to move backward.

Thus, in a state where the cassette 100 is loaded to the drug injection device 200, the cassette 100 cannot be removed, and the operator is kept from inadvertently pulling out the cassette 100. Note that the ejection lever 209 may include a lock button 209c. The lock button 209c is configured so as to allow sliding of the ejection lever 209 only while the lock button 209c is pressed. With such a configuration, sliding of the ejection lever 209 will also require a press manipulation, so that the operator needs to manipulate the ejection lever 209 more consciously. Thus, the lock button 209c betters suppresses malfunctioning.

[Placement of Various Detectors]

Various detectors of the drug injection device 200 as shown in FIG. 2 will be described altogether. FIG. 19 is a cross-sectional view of the drug injection device 200.

As described above, the encoder 265 is mounted on the shaft of the injection motor 264, and measures the number of revolutions of the injection motor 264. The piston origin detector 271 detects that the piston 210 has moved backward to the initial position, for example. The origin may be set at a position other than the initial position. For example, the piston origin detector 271 may be a microswitch, etc., that is placed so as to be pressed by the rear end of the piston 210 when the piston 210 has moved backward to the initial position.

The cassette loading detector 272 detects loading or ejection of the cassette 100 to or from the cassette space 201c. For example, a door 205 may be provided on the case opening 201d, and the cassette loading detector 272 may be a microswitch, etc., that is pressed when the door opens.

The cassette retention detector 273 detects that the cassette 100 is or is not load to the cassette space 201c. The cassette retention detector 273 may be a microswitch, etc., that is placed closed to the cassette space 201c and is pressed by the loaded cassette 100, for example.

The ejection lever detector 274 detects that the ejection lever 209 has been manipulated. The ejection lever detector 274 may be a microswitch, etc., that is placed closed to the ejection lever 209 and is pressed when the ejection lever 209 has slid, for example.

The skin abutment detection sensor 275 detects that the skin abutment surface 201b has abutted with skin. The skin abutment detection sensor 275 may be a touch sensor, pressure sensor, etc., that is placed on the skin abutment surface 201b, for example.

(Operations of the Drug Injection System)

With reference to cross-sectional views shown in FIG. 19A to FIG. 19K and flowcharts shown in FIG. 20A and FIG. 20B, operations and procedures for use of the drug injection system will be described.

[1. Operation of Using an Unused Drug Cartridge 10 for the First Time]

(1) State Before Cassette Loading, and Activation of Drug Injection Device (FIG. 19A, S1)

The drug injection device 200 is compatible with a drug cartridge that contains an amount of drug to be separately injected over a plurality of times. Therefore, the control device 280 stores an administration history of each drug cartridge, i.e., the used amount or the number of administered doses of the drug, in the memory 254. The used amount is an amount of drug that has been used since the drug cartridge was still unused. The number of administered doses is a number of times that the drug cartridge has been used since it was still unused. Hereinafter, an operation of the drug injection system 300 will be described, from the state where the used amount or the number of administered doses stored in the memory 254 of the control device 280 is zero.

As will be described below, when the used amount is zero, the piston 210 of the drug injection device 200 is in an initial position, where it has moved backward to the rear end. In this state, the drive rod 235 is almost completely inserted in the hole 210h of the piston 210. Moreover, the piston 210 is at a rotation angle that allows it to be inserted into the unit throughhole 120c in the unlock position.

As the operator presses the power button 255 (FIG. 1), the drug injection device is activated (S1).

(2) Loading of Cassette (FIG. 19B, S2)

The cassette 100 having the unused drug cartridge 10 placed therein is pressed against the door 205, the door 205 is opened, and the cassette 100 is inserted in the cassette space 201c within the drug injection device 200. The cassette loading detector 272 and the cassette retention detector 273 detect the loading and retention of the cassette 100. Because the rotation lock unit 120 of the cassette 100 is in the unlock position, the leading end portion 211 of the piston 210 is inserted in the unit throughhole 120c of the rotation lock unit 120.

(3) Locking of Cassette (FIG. 19C, FIG. 19D, S3, S4)

The control device 280 determines whether the used amount of the drug as stored in the memory 254 is zero or not (S3). Because the used amount of the drug as stored in the memory 254 is zero (following "YES" from S3), the drug injection device 200 performs a locking operation of the cassette 100. When the cassette loading detector 272 and the cassette retention detector 273 detect loading of the cassette 100, the control device 280 causes the injection motor 264 to rotate forward, whereby the drive rod 235 rotates. As a result, the piston 210 is guided by the first guide 203, so as to rotate by the angle α while moving forward. While moving forward in the unit throughhole 120c of the rotation lock unit 120, the leading end portion 211 of the piston 210 rotates the rotation lock unit 120 to the lock position. As a result, the cassette cap 130 is locked (S4). The piston 210 further moves forward and abuts with the gasket 13 of the drug cartridge 10, whereby rotation of the injection motor 264 stops.

As will be described below, when a cassette 100 including a drug cartridge 10 with a non-zero used amount is loaded, the used amount of the drug as stored in the memory 254 is not zero, and thus this step is skipped (following "NO" from S3).

(4) Setting of Dosage (S5)

As necessary, the operator determines a single dosage of the drug in the drug cartridge 10 and inputs it by using the selection button 256 and the OK button 257 of the drug injection device 200 (FIG. 1). At this time, the set dosage that has been input is stored to the memory 254.

(5) Mounting of Injection Needle (FIG. 19E, S6)

The operator mounts the injection needle 21 to the first end 100a of the cassette 100 (S6).

(6) Needle Insertion and Injection (FIG. 19F, 19G, 19H, S7, S8)

The operator places the skin abutment surface 201b of the outer housing 201 on skin 400, and inserts the injection needle 21 into the skin 400 (FIG. 19F, S7). As a result, the skin abutment detection sensor 275 detects abutment of the skin 400. When the operator presses the injection button 258 (FIG. 1), in response to detection by the skin abutment detection sensor 275 and pressing of the injection button 258, the control device 280 causes the injection motor 264 to rotate forward and rotates the drive rod 235, whereby piston 210 moves forward. As the gasket 13 moves forward together with the piston 210, the drug is injected (FIG. 19G). The control device 280 causes the injection motor 264 to rotate forward so that the piston 210 moves by an amount of movement that is calculated based on the set dosage, and thereafter stops it (FIG. 19H, S8).

(7) Needle Extraction and Removal of Injection Needle (FIG. 19I, FIG. 19J, S9, S10)

The operator extracts the injection needle 21 from the skin 400 (FIG. 19I, S9), and removes the injection needle 21 from the cassette 100 (FIG. 19J, S10).

(8) Determination of Need to Retract the Piston (S11)

Based on the injected amount of drug, the control device 280 updates the used amount of the drug, and stores it to the memory 254. Moreover, it determines a remaining amount of drug in the drug cartridge 10 from the amount of drug contained in the unused drug cartridge 10 and the used amount. If the remaining amount of drug is zero or equal to or less than a predetermined amount, as will be described below, a retraction operation of the piston 210 is performed. If the remaining amount of drug is not zero, removal of the cassette is performed.

(9) Removal of Cassette 100 (FIG. 19K, S13, S14)

The operator slides the ejection lever 209, and removes the cassette 100. As a result, the ejection lever detector 274 detects manipulation of the ejection lever 209, and the cassette loading detector 272 and the cassette retention detector 273 detect ejection of the cassette 100 (S14).

Before ejection of the cassette 100, a shutdown process of causing the piston 210 to slightly move backward may be performed (S13). In the shutdown process, the control device 280 causes the injection motor 264 to rotate backward so that the piston 210 moves backward by a predetermined amount, and stops it. As a result, when the cassette 100 is loaded the next time, the gasket 13 placed at the rear end of the drug cartridge 10 is kept from abutting with the piston 210 and allowing the drug to be discharged unintentionally. Since only the abutment at the time of loading may be suppressed, the piston 210 only needs to move backward by a small distance, e.g., about 1 mm.

The cassette 100 that has been removed in this state is in a state of being locked by the rotation lock unit 120. Moreover, some drug is still left in the drug cartridge 10. Thus, the operator is kept from inadvertently opening the cassette cap 130 to remove the drug cartridge 10 with drug left therein, and throwing it away.

(10) Stopping of Drug Injection Device (S15)

As the operator presses the power button 255, the drug injection device 200 stops (S15).

(11) As the Operator Presses the Power Button 255, the Drug Injection Device 200 Stops.

[2. Operation of Using an Unfinished Drug Cartridge 10]

When conducting an injection by using a cassette 100 accommodating an unfinished drug cartridge 10, the aforementioned procedures from (1) to (11) are performed in similar manners. However, the used amount of the drug based on information concerning the used amount of the drug that is stored in the memory 254 is not zero; the piston 210 is at a position where it has moved forward from the initial position; and the cassette 100 is locked. Therefore, the locking operation (S4) of the cassette is not performed.

Moreover, because the piston 210 is at an angular position that is suitable for a locked cassette 100, the cassette 100 accommodating an unfinished drug cartridge 10 can be properly loaded to the drug injection device 200. On the other hand, when one tries to load a cassette 100 accommodating an unused drug cartridge 10, the orientation of the unit throughhole 120c and the orientation of the piston 210 do not match, and therefore the cassette 100 cannot be properly loaded.

Moreover, the piston 210 has not retracted, or if at all, retracted by a small amount. Therefore, when the cassette 100 is loaded to the drug injection device 200, the piston 210 can abut with the gasket 13 without taking time. That is, not much time is needed until injection becomes possible.

After drug injection, in determining the need to retract the piston (S11), if the remaining amount of drug is zero or equal to or less than a predetermined amount (FIG. 19L), cancellation of locking of the cassette 100 and retraction of the piston 210 to the initial position are performed (FIG. 19M, S12). Specifically, the control device 280 causes the injection motor 264 to rotate backward, and rotates the drive rod 235. As a result, the piston 210 moves backward while being guided by the second guides 231. Upon reaching the first guide 203, it further moves backward while rotating backward by the angle α. At this time, because the leading end portion 211 of the piston 210 is located in the unit through-hole 120c of the rotation lock unit 120, the rotation lock unit 120 rotates, and returns to the unlock position. As a result, the cassette cap 130 enters an unlocked state. Furthermore, the piston 210 moves backward, and the piston origin detector 271 detects that the piston 210 has moved backward to the initial position, upon which rotation of the injection motor 264 is stopped.

Thereafter, (9) removal of the cassette 100 (S14) and (10) stopping of the drug injection device 200 (S15) are performed. At this time, in a shutdown process (S14), the used amount of the drug is updated to zero, and stored to the memory 254. As a result, at the next time of use, a cassette 100 accommodating an unused drug cartridge 10 is usable. (Other Implementations)

The drug injection device according to the above embodiment is a semi-automatic type; however, the drug injection device according to the present disclosure may be a full-automatic type. FIG. 21A is a perspective view showing the appearance of a full-automatic type drug injection device 200', and FIG. 21B is a perspective view showing the configuration of main portions, from which the case has been removed. FIG. 21B is a cross-sectional view of the drug injection device 200'. FIG. 22 is a block diagram showing an example configuration of the electric circuitry of the drug injection device 200'. Since the drug injection device 200' is a full-automatic type, it differs from the drug injection device 200 according to the above-described embodiment, in that the drug injection device 200' includes a needle insertion/extraction motor 278 to perform needle insertion and needle extraction, a needle insertion/extraction motor driver 279, a needle insertion position detector 276, and a needle extraction position detector 277.

In the drug injection device 200', the needle insertion/extraction motor 278 drives the cassette 100 so that the entire cassette 100 moves forward or backward. The needle insertion position detector 276 and the needle extraction position detector 277 detect the position of the cassette 100 at the times of needle insertion and needle extraction.

FIG. 23A and FIG. 23B are flowcharts showing procedures for manipulating the drug injection device 200'. The manipulation of drug injection device 200' is identical to the manipulation of the drug injection device 200 except that, through the control device 280, the needle insertion/extraction motor 278 performs needle insertion and needle extraction manipulation.

Specifically, instead of the operator placing the skin abutment surface 201b of the outer housing 201 against the skin 400 and inserting the injection needle 21 into the skin 400 (FIG. 19F, S7), the operator causes the leading end of the drug injection device 200' to abut with the skin (S7-1); the skin abutment detection sensor 275 detects abutment of the skin, which enables needle insertion based on the detection result; and the control device 280 causes the needle insertion/extraction motor 278 to rotate forward, whereby the cassette 100 moves forward. Thus, a needle insertion operation is carried out (S7-2). When the needle insertion position detector 276 detects that the cassette has moved by a predetermined amount, the control device 280 performs a drug injecting operation (S8).

Also, instead of the manipulation where the operator extracts the injection needle 21 from the skin (FIG. 19I, S9), the control device 280 causes the needle insertion/extraction motor 278 to rotate backward after the drug injecting operation, whereby the cassette 100 moves backward. Thus, a needle extraction operation (S9-1) is carried out. When the needle extraction position detector 277 detects that the cassette has moved by a predetermined amount, the control device 280 stops the needle insertion/extraction motor 278. Thereafter, the operator removes the drug injection device 200' from the skin (S9-2). The other procedures are performed similarly to the manners they are performed by the drug injection device 200.

With such a full-automatic type drug injection device, similar effects to those attained by the aforementioned semi-automatic type drug injection device can be obtained.

The above-described embodiments are only examples, and various modifications can be made to the cassette 100, the drug injection device 200, the drug injection device 200', and the drug injection system 300. For example, the cross-sectional shape of the leading end portion 211 of the piston 210 and the cross-sectional shape of the unit throughhole 120c may be shapes other than those described with respect to the above embodiments. Moreover, the rotation lock mechanism as well as the first guide for causing the piston 210 to rotate, the second guide, the driving bumps, and the like may implemented by combining other mechanical elements.

INDUSTRIAL APPLICABILITY

A cassette, a drug injection device, and a drug injection system according to the present disclosure are suitably used for devices for injecting various drugs.

REFERENCE SIGNS LIST 10 drug cartridge
10b second end
11 cylinder
11a first end
11b second end
11c cylinder columnar space
11d cylinder opening
12 cylinder cap
13 gasket
14 drug
20 needle unit
21 injection needle
22 needle
23 interconnecting section
24 needle cap
25 needle case
100 cassette
100a first end
110 cartridge holder
110a first end
110b second end
110c holder columnar space
110d holder opening
110e aperture 110*f* opening
110*g* lock recess
110*j* holder support
111 cassette button
111*d* connecting portion
111*g* engaging portion
120 rotation lock unit
120*c* unit throughhole
121 ring portion
121*a* first end
121*b* second end
121*c* throughhole
121*ca* axis
121*d* first side surface subportion
121*e* second side surface subportion
121*ee* space
121*f* abutting surface
121*g* groove
121*g*1 end
121*g*2 end
121*gt* stopper bump
121*h* groove
121*h*1 end
121*h*2 end
121*ht* stopper bump
121*i* sloped surface
122 cylindrical portion
122*c* internal space
122*d* cutout
122*e* cutout
122*s* side surface
123 cartridge stopper
124 spring
125 cassette lock-ring
126 ring portion
126*a* first end
126*b* second end
126*c* throughhole
126*f* surface
126*g*1 first ring engaging portion
126*g*2 second ring engaging portion
126*h*1 groove
126*h*2 groove
126*r* colored region
126*s* side surface
127*d* protrusion
127*e* protrusion
130 cassette cap
130*a* first end
130*b* second end
130*c* cap columnar space
130*d* cap opening
130*e* piston insertion opening
130*f* button space
130*g* engaging portion
130*h* alarming aperture
130*i* aperture
130*j* cap support
130*k* cap engaging portion
130*m* inner surface
130*t*1 cap bump
130*t*2 cap bump
131 shaft
200 drug injection device
200' drug injection device
201 outer housing
201*r* recess 201*b* skin abutment surface
201*c* cassette space
201*d* case opening
202 inner housing
202*d* gear region
202*f* piston guide region
202*g* bump
202*h* cassette region
203 first guide
203*f* helical surface
203*r* helical surface
205 door
209 ejection lever
209*c* lock button
210 piston
210*a* first end
210*b* second end
210*h* hole
211 leading end portion
212 main body
213 driving bump
214 internal thread
215 slide base
215*c* base portion
215*d* ring portion
215*e* base abutting portion
220 piston driving mechanism
221 gearbox
222 drive gear
223 bearing
230 piston guide
230*c* flange
230*g* groove
230*h* hole
231 second guide
232 clamp section
232*c* clamp abutting portion
235 drive rod
236 external thread
241 cassette retention arm
241*c* first abutting portion
241*d* second abutting portion
241*e* pivot
241*f* bump
241*g* tab
242 arm spring
243 piston guide spring
251 control section
252 recharging section
253 rechargeable battery
254 memory
255 power button
256 selection button
257 OK button
258 injection button
259 display section
260 buzzer
261 clock
262 communication section
263 injection motor driver
264 injection motor
265 encoder
271 piston origin detector
272 cassette loading detector
273 cassette retention detector
274 ejection lever detector
275 skin abutment detection sensor 276 needle insertion position detector
277 needle extraction position detector
278 needle insertion/extraction motor
279 needle insertion/extraction motor driver
280 control device
300 drug injection system
400 skin

The invention claimed is:

1. A cassette to be loaded to a drug injection device, the cassette comprising:

a cartridge holder including a first end at which an injection needle is attachable and detachable, a second end having a holder opening, and a holder columnar space being located between the first end and the second end and capable of accommodating a drug cartridge, wherein the drug cartridge includes: a cylinder including a first end at which the injection needle is insertable and extractable, a second end at which a cylinder opening is located, and a cylinder columnar space located between the first end and the second end; a drug placed in the cylinder columnar space; and a gasket being placed in the cylinder columnar space and capable of moving along a longitudinal direction of the cylinder columnar space;

a cassette cap being supported in the neighborhood of the second end of the cartridge holder so as to be capable of opening and closing the holder opening, the cassette cap including a first end having a cap opening that is opposed to the holder opening, a second end having a piston insertion opening, and a cap columnar space located between the first end and the second end, wherein, in an open state, the cassette cap allows the drug cartridge to be movable into and out of the holder columnar space of the cartridge holder, and, in a closed state, the cassette cap closes the holder opening to disallow the drug cartridge to be removed while allowing the gasket of the drug cartridge inserted into the holder columnar space to be exposed in the piston insertion opening; and a locking mechanism being located in the cap columnar space of the cassette cap and at least including a rotation lock unit that is supported so as to be capable of pivoting around an axis of the cap columnar space, wherein, the rotation lock unit has a shape that engages with a piston of the drug injection device for moving the gasket of the drug cartridge, while the drug cartridge is inserted in the cartridge holder and the cassette cap is in a closed state, the rotation lock unit pivots between a lock position for disallowing the cassette cap to open and an unlock position for allowing the cassette cap to open, the rotation lock unit includes a unit throughhole having a cross-sectional shape that corresponds to a cross-sectional shape of a leading end portion of the piston perpendicular to an axis of the piston, as the leading end portion of the piston is inserted from outside into the unit throughhole of the rotation lock unit and the piston rotates around the axis of the piston, the rotation lock unit pivots within the cassette cap, the locking mechanism further includes:

a cassette button provided on the cartridge holder so as to be capable of being pressed; and a pair of engaging portions respectively provided on the cassette button and on the cassette cap, the engaging portions being capable of engaging with each other, when the rotation lock unit is in the unlock position, the cassette button is pressable so that the pair of engaging portions are disengaged from each other while the cassette button is pressed, and when the rotation lock unit is in the lock position, the cassette button is unpressable and the pair of engaging portions are engaged with each other.

2. The cassette of claim 1, wherein a projected image of the unit throughhole of the rotation lock unit as projected on a plane perpendicular to an axis thereof differs between when the rotation lock unit is in the lock position and when the rotation lock unit is in the unlock position.

3. The cassette of claim 2, wherein the rotation lock unit is unpivotable when the drug cartridge is not inserted in the cartridge holder and the cassette cap is in the closed state.

4. The cassette of claim 1, further comprising an alarming section to inform that the rotation lock unit is in the lock position and/or the unlock position.

5. The cassette of claim 4, wherein, the alarming section includes an alarming hole located on a side surface of the cassette cap and a colored region provided on a side surface of the rotation lock unit;

when the rotation lock unit is in the unlock position, the colored region is located outside the alarming hole; and, when the rotation lock unit is in the lock position, the colored region is located in the alarming hole.

6. The cassette of claim 1, wherein, the rotation lock unit includes a cassette lock-ring, a cartridge stopper, and a spring disposed between the cassette lock-ring and the cartridge stopper;

the cassette lock-ring and the cartridge stopper compose the unit throughhole in a unitary manner, and are capable of rotating in the cap columnar space in a unitary manner, and, in the cap columnar space of the cassette cap, the cartridge stopper is urged toward the first end of the cassette cap and the cassette lock-ring is urged toward the second end of the cassette cap by the spring.

7. The cassette of claim 6, wherein, the cassette cap includes a cap bump protruding into the cap opening;

the cartridge stopper includes an abutting surface to abut with the second end of the drug cartridge inserted in the cartridge holder while the cassette cap is closed, and a stopper bump located outside of the abutting surface; and, when the drug cartridge is not loaded in the cartridge holder and the cassette cap is closed, the stopper bump abuts with the cap bump to restrict pivoting of the rotation lock unit, and, when the drug cartridge is loaded in the cartridge holder and the cassette cap is closed, abutment between the second end of the drug cartridge and the abutting surface of the cartridge stopper causes the cartridge stopper to move backward toward the second end of the cassette cap, causes the stopper bump to become spaced apart from the cap bump, and enables the rotation lock unit to pivot.

8. The cassette of claim 7, wherein, the cartridge stopper includes a first side surface subportion and a second side surface subportion;

in a plane perpendicular to the axis of the piston, a shortest distance between the second side surface subportion and the axis of the piston is shorter than a shortest distance between the first side surface subportion and the axis of the piston;

when the rotation lock unit is in the lock position, abutment between the first side surface subportion and the cassette button keeps the cassette button unpressable; and, when the rotation lock unit is in the unlock position, the cassette button is pressable until the cassette button abuts with the second side surface subportion.

9. The cassette of claim 7, wherein, the cassette lock-ring and the cartridge stopper each have a ring portion;

the abutting surface and the stopper bump of the cartridge stopper are located on the ring portion;

one of the cassette lock-ring and the cartridge stopper includes at least one cutout extending in parallel to an axis of the rotation lock unit and a side surface of a barrel shape that is connected to the ring portion, and the other includes at least one protrusion connected to the ring portion, the at least one protrusion having a shape extending in parallel to the axis of the rotation lock unit and matching the at least one cutout; and, when the at least one protrusion is inserted in the at least one cutout, the cassette lock-ring and the cartridge stopper are capable of moving with respect to each other along the axial direction so that the respective ring portions thereof come closer or become farther apart.

10. The cassette of claim 9, wherein, the ring portion of the cassette lock-ring includes a first ring engaging portion and a second ring engaging portion that are located on a surface opposed to an inner surface of the second end of the cassette cap;

on the inner surface of the second end of the cassette cap, the cassette cap includes a cap engaging portion that is capable of selectively engaging with the first ring engaging portion or the second ring engaging portion;

when the rotation lock unit is in the unlock position, the cap engaging portion engages with the first ring engaging portion; and when the rotation lock unit is in the lock position, the cap engaging portion engages with the second ring engaging portion.

11. The cassette of claim 1, wherein a cross section of the unit throughhole has an I shape.

12. The cassette of claim 1, wherein, the lock position and the unlock position of the rotation lock unit make an angle $\alpha$ around the axis of the cap columnar space in a plane perpendicular to the axis of the cap columnar space, and a cross section of the unit throughhole has a rotation symmetry other than $(360/\alpha)$-fold symmetric.

13. A drug injection device comprising: a case including a case opening and a cassette space to accommodate at least a portion of the cassette of claim 1;

a piston driving mechanism to drive the piston in a direction of moving forward or backward and to rotate the piston around the axis of the piston; and a control device to control the piston driving mechanism, wherein, the piston is capable of moving forward or backward along a direction parallel to the axis of the piston and rotating around the axis of the piston, wherein, when moving forward, the piston is capable of abutting with the gasket of the drug cartridge accommodated in the cassette that is placed in the cassette space and pushing in the gasket, and as the piston driving mechanism rotates the piston around the axis thereof, the piston causes the rotation lock unit of the cassette to pivot between the lock position and the unlock position.

14. The drug injection device of claim 13, wherein the piston includes a main body connected to the leading end portion, an outer edge of a projected shape of the main body as projected on a plane perpendicular to the axis of the piston is located inward of an outer edge of a projected shape of the leading end portion.

15. The drug injection device of claim 13, wherein, the piston driving mechanism includes:

a driving bump; and a first guide including a helical groove into which the driving bump is inserted, and a second guide including a linear groove into which the driving bump is inserted; and the driving bump or the first guide and second guide is/are located on a side surface of the piston.

16. The drug injection device of claim 15, wherein, the driving bump is located on the side surface of the piston; and the second guide is located between the first guide and the cassette space.

17. The drug injection device of claim 16, further comprising a piston guide having a hole into which at least a portion of the piston is insertable, wherein, the second guide is located on an inner side surface of the hole of the piston guide; and the first guide is located on the case.

18. The drug injection device of claim 15, wherein, the piston driving mechanism further includes:

an injection motor to be driven under the control of the control device;

a drive rod having an external thread formed on a side surface, the drive rod being axially rotated by the injection motor; and an internal thread meshing with the external thread of the drive rod and being provided on the axis of the piston, wherein, as the drive rod rotates while the internal thread of the piston is meshed with the external thread of the drive rod, the piston is driven in the direction of moving forward or backward.

19. The drug injection device of claim 18, wherein, as the drive rod rotates while the driving bump is inserted in the helical groove of the first guide, the piston causes the rotation lock unit of the cassette to pivot between the lock position and the unlock position.

20. The drug injection device of claim 19, wherein, while the driving bump is inserted in the linear groove of the second guide, the piston does not rotate, and the rotation lock unit of the drug cartridge is maintained in the lock position.

21. The drug injection device of claim 13, wherein the leading end portion of the piston has an I-cut shape.

22. The drug injection device of claim 13, wherein, the control device stores a used amount or a number of administered doses of the drug, and, when the used amount or the number of administered doses of the drug is zero:

before a drug injecting operation, the control device controls the piston driving mechanism to move the piston in the direction of moving forward, and to rotate the piston so that the rotation lock unit of the cassette pivots from the unlock position to the lock position;

based on an instruction from an operator, the control device controls the piston driving mechanism to move the piston in the direction of moving forward but without rotating, to cause the gasket of the drug cartridge to move and allow the drug to be discharged from the injection needle; and, after discharging of the drug, the control device updates and stores the used amount or the number of administered doses of the drug, and ends the drug injection operation without moving the piston in the direction of moving backward.

23. The drug injection device claim 13, wherein, the control device stores a used amount or a number of administered doses of the drug, and, when the used amount or the number of administered doses of the drug is not zero:

based on an instruction from an operator, the control device controls the piston driving mechanism to move the piston in the direction of moving forward but without rotating, to cause the gasket to move and allow the drug to be discharged from the injection needle;

after discharging of the drug, the control device updates and stores the used amount or the number of administered doses of the drug, and, when a remaining amount of the drug as calculated based on an updated used amount or an updated number of administered doses of the drug is equal to or greater than a predetermined value, the control device ends operation without moving the piston in the direction of moving backward; and, when the remaining amount of the drug as calculated based on the updated used amount or the updated number of administered doses of the drug is less than the predetermined value, the control device controls the piston driving mechanism to move the piston in the direction of moving backward, and to rotate the piston so that the rotation lock unit of the cassette pivots from the lock position to the unlock position, and to move the piston to an initial position, and ends the operation.

*    *    *    *    *